(12) United States Patent
Takami et al.

(10) Patent No.: US 6,246,432 B1
(45) Date of Patent: Jun. 12, 2001

(54) VIDEO SIGNAL SWITCHING DEVICE FOR ENDOSCOPE SYSTEM

(75) Inventors: Satoshi Takami, Saitama; Noriaki Takahashi, deceased, late of Saitama, by Akemi Takahashi, heir; Kohei Iketani, Saitama, all of (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/085,754

(22) Filed: May 27, 1998

(30) Foreign Application Priority Data

| May 27, 1997 | (JP) | 9-137159 |
| Jun. 11, 1997 | (JP) | 9-153589 |
| Jun. 11, 1997 | (JP) | 9-153590 |
| Mar. 24, 1998 | (JP) | 10-076227 |
| Mar. 24, 1998 | (JP) | 10-076228 |

(51) Int. Cl.$^7$ ................................................ H04N 5/268
(52) U.S. Cl. ................................................ 348/65; 348/705
(58) Field of Search ................................. 348/65, 72, 75, 348/71, 705, 706; H04N 5/268, 7/18

(56) References Cited

U.S. PATENT DOCUMENTS

| 4,853,773 | 8/1989 | Hibino et al. . |
| 5,412,478 | 5/1995 | Ishihara et al. . |
| 5,583,566 | 12/1996 | Kanno et al. . |

FOREIGN PATENT DOCUMENTS

| 63-200735 | 8/1988 | (JP) . |
| 3-159490 | 7/1991 | (JP) . |
| 4-1123382 | 4/1992 | (JP) . |
| 8-107878 | 4/1996 | (JP) . |

OTHER PUBLICATIONS

English language abstract of JP 8–107878.
English language abstract of JP 7–112382.

*Primary Examiner*—David E. Harvey
(74) *Attorney, Agent, or Firm*—Greenblum & Bernstein, P.L.C.

(57) ABSTRACT

An endoscope system comprises plural video processor devices for an endoscope prepared for every video endoscope, a video signal switching device connected to each of the video processor devices for an endoscope, and a monitor connected to the video signal switching device. The video signal switching device comprises two video signal input terminals respectively connected to the video processor devices, a flip flop for generating an alternative switching signal in accordance with the rotational position of a switching dial, two switches of which one ends respectively connected to the video signal input terminals and which opens and closes in accordance with the switching signal generated from this flip flop, and a video signal output terminal connected to the other ends of these two switches.

20 Claims, 33 Drawing Sheets

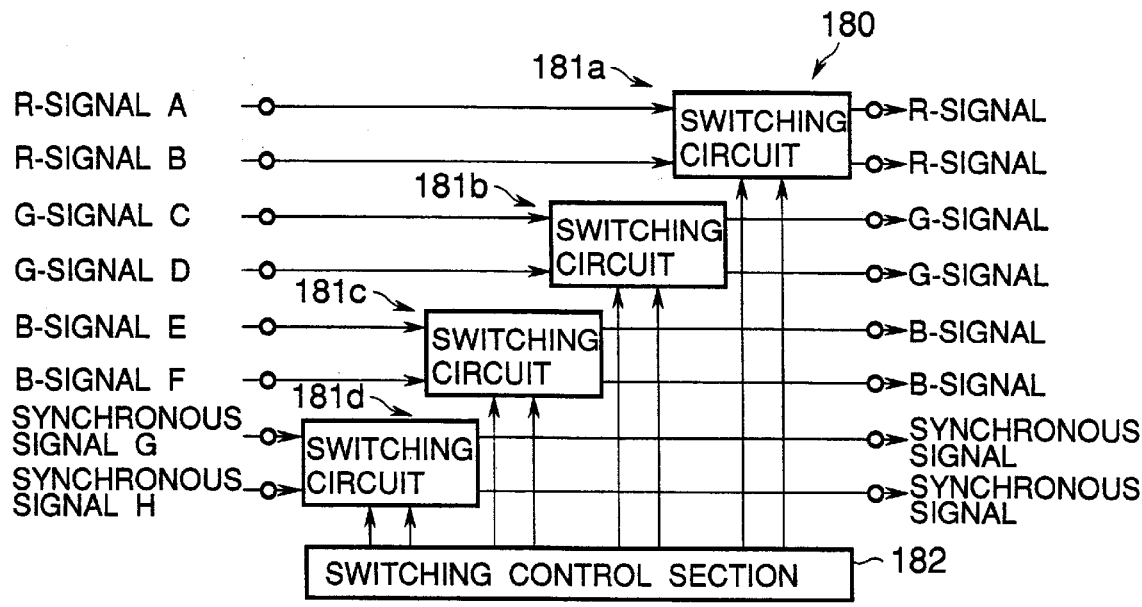

FIG.27

| SWITCHING SECTION ASSOCIATING PATTERN | | | | | | | | | VIDEO INPUT PATTERN |
|---|---|---|---|---|---|---|---|---|---|
| | 111a | 111b | 111c | 111d | 111e | 111f | 111g | 111h | |
| SETTING 1 | ○ | ○—○ | ○—○ | ○ | ○—○ | ○—○ | ○—○ | ○ | 4 SYSTEMS OF RGB |
| SETTING 2 | ○ | ○—○ | ○—○ | ○ | ○—○ | ○—○ | ○ | ○ | 2 SYSTEMS OF RGB & 4 SYSTEMS OF Y/C |
| SETTING 3 | ○ | ○—○ | ○—○ | ○ | ○ | ○ | ○—○ | ○ | 2 SYSTEMS OF RGB & 2 SYSTEMS OF Y/C & 4 SYSTEMS OF NTSC |
| SETTING 4 | ○ | ○—○ | ○—○ | ○ | ○ | ○ | ○ | ○ | 2 SYSTEMS OF RGB & 4 SYSTEMS OF NTSC |
| SETTING 5 | ○ | ○ | ○ | ○ | ○—○ | ○—○ | ○—○ | ○ | 4 SYSTEMS OF Y/C |
| SETTING 6 | ○ | ○—○ | ○—○ | ○ | ○ | ○ | ○ | ○ | 6 SYSTEMS OF Y/C & 2 SYSTEMS OF NTSC |
| SETTING 7 | ○ | ○—○ | ○—○ | ○ | ○ | ○ | ○—○ | ○ | 6 SYSTEMS OF Y/C & 2 SYSTEMS OF NTSC |
| SETTING 8 | ○ | ○—○ | ○—○ | ○ | ○ | ○ | ○ | ○ | 4 SYSTEMS OF Y/C & 8 SYSTEMS OF NTSC |
| SETTING 10 | ○ | ○ | ○ | ○ | ○ | ○ | ○ | ○ | 16 SYSTEMS OF NTSC |

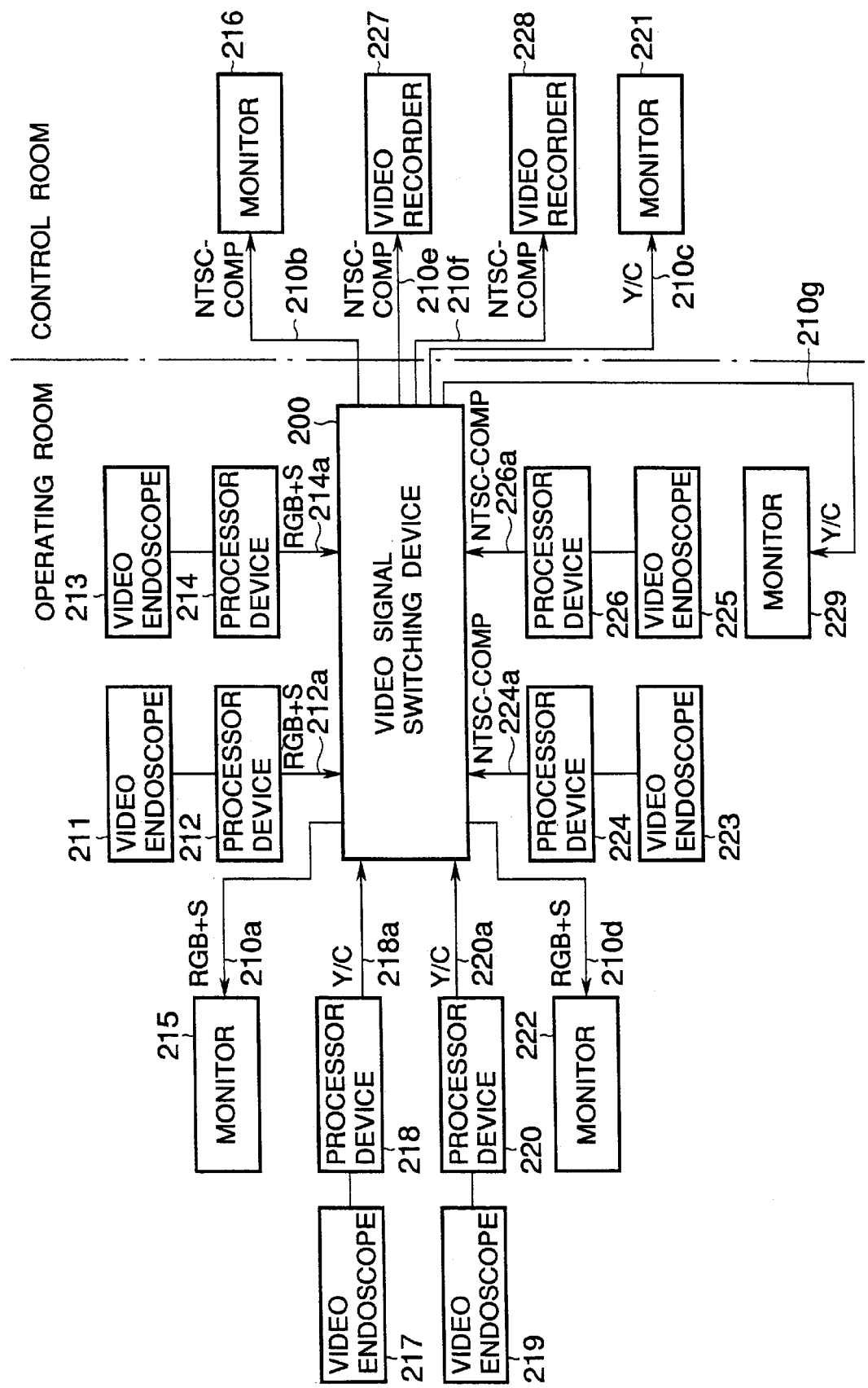

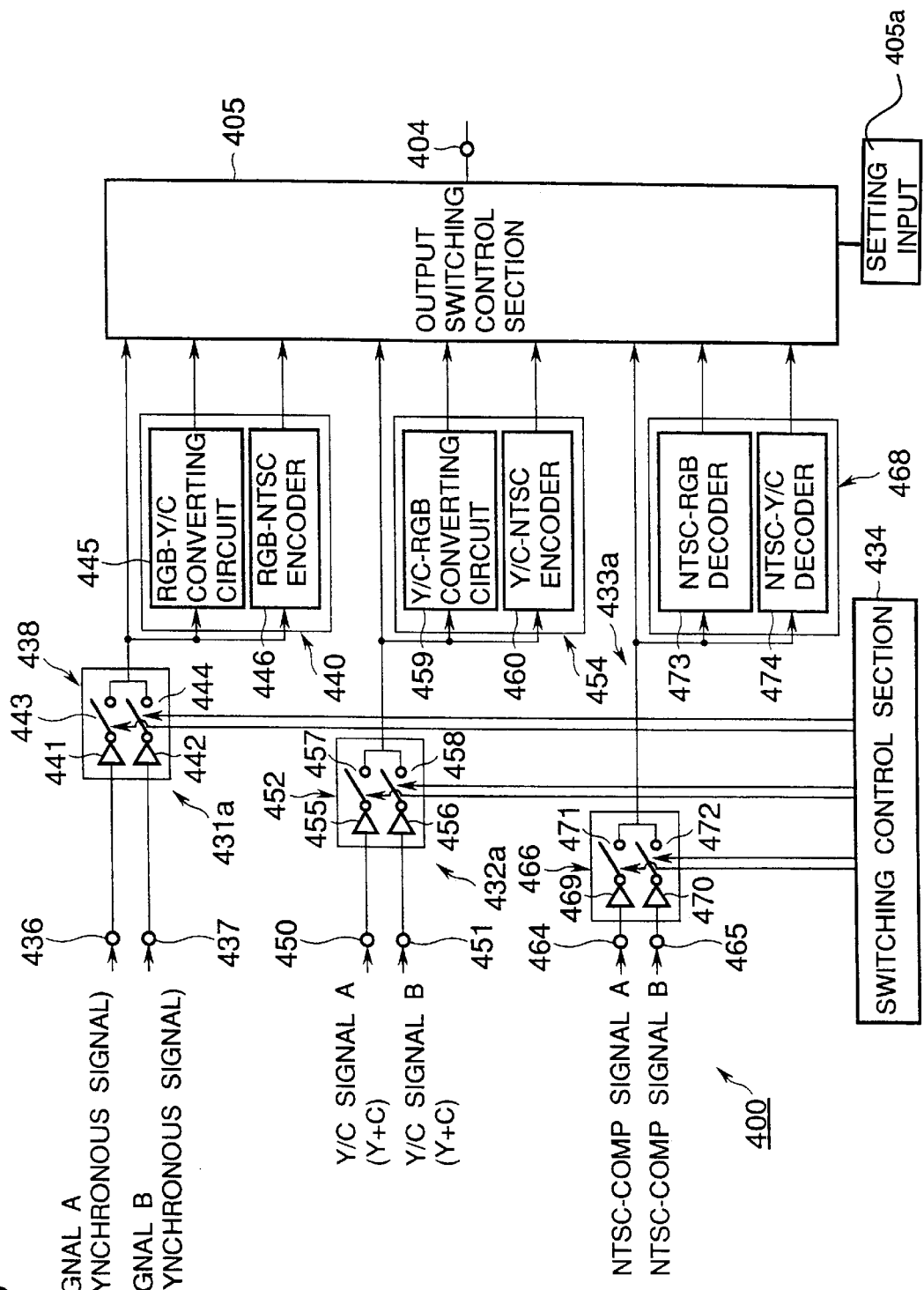

VIDEO SIGNAL SWITCHING DEVICE FOR ENDOSCOPE SYSTEM

BACKGROUND OF THE INVENTION

1. Field of the Invention

The present invention relates to a video signal switching device for an endoscope system connected to plural video processor devices for an endoscope and capable of selectively outputting a video signal inputted from each of these video processors. The present disclosure related to subject matter contained in Japanese Patent Application No. 9-137159 (filed on May 27, 1997), No. 9-153590 (filed on Jun. 11, 1997), No. 9-153589 (filed on Jun. 11, 1997), No. 10-76227 (filed on March 24) and No. 10-76228 (filed on March 24), which are expressly incorporated herein by reference in its entirety.

2. Description of the Related Art

An image processing circuit is built in a video processor device used in an endoscope system. The image processing circuit converts a CCD output signal outputted from a video endoscope of a RGB field sequential system or a color mosaic filter system to a video signal such as an RGB component signal, Y/C signals, an NTSC composite signal, etc. Conventionally, for example, as disclosed in Japanese Patent Application Laid-Open (JP-A) No. 63-200735, there is a known video processor device which has two connector sockets respectively connectable to the video endoscope of the RGB field sequential system and the video endoscope of the color mosaic filter system, a signal processing circuit to process the CCD output signal in the RGB field sequential system, a signal processing circuit to process the CCD output signal in the color mosaic filter system, a video signal switching device to select one of video signals respectively outputted from these signal processing circuits and to output the selected video signal to an external monitor device, etc.

Such a video processor device installed with the video signal switching device is excellent in that the video endoscopes of two kinds can be simultaneously connected to the video processor device and images photographed by these two video endoscopes can be selectively displayed on one monitor. However, such a video processor device installed with the video signal switching device forces an overladen cost if an user already has a video processor device dedicated for the RGB field sequential system and installed with only an image processing circuit for processing the CCD output in the RGB field sequential system and also has a video processor device dedicated for the color mosaic filter system and installed with only an image processing circuit for processing the CCD output in the color mosaic filter system, which makes these existing video processor devices useless. Further, for example, when a video endoscope of a new system such as a 3CCD system is developed, no conventional video processor device can cope with this new system. In such a case, user must use both the conventional video processor device installed with the video signal switching device and a video processor device dedicated for the new system in parallel, and connect monitor devices to these video processor devices respectively.

SUMMARY OF THE INVENTION

An object of the present invention is to provide a video signal switching device of an endoscope system which can receive video signals respectively outputted from plural video processor devices irrespective of the system of a CCD output signal processed by the processor devices, and select any one of these inputted video signals to output through the same output terminal.

To achieve this object, a video signal switching device of the present invention selectively outputs video signals received from plural video processor devices for endoscopes. The video signal switching device is separated from said video processor devices. This video signal switching device comprises plural video signal input terminals to be connected to respective video signal output terminals of the video processors, a video signal output terminal through which a video signal is outputted, and a connecting changeover switch to select any one of the plural video signal input terminals to connect the selected input terminal to said video signal output terminal in accordance with a control signal.

The invention will be described below in detail with reference to the accompanying drawings, in which:

FIG. 23 is a circuit diagram showing a main portion of an application example of the video signal switching device shown in FIG. 19.

FIG. 24 is a table showing a variation of video signals inputted into the respective switching circuits in the video signal switching device in the seventh embodiment of the present invention.

FIG. 27 is a table showing a variation of video signals inputted into the respective switching circuits in the video signal switching device in the eighth embodiment of the present invention.

FIG. 28 is a schematic view of an endoscope system in a ninth embodiment of the present invention.

FIG. 36 is a circuit diagram of a main portion of a video signal switching device in an eleventh embodiment of the present invention.

DESCRIPTION OF THE PREFERRED EMBODIMENT

The embodiments of the present invention will next be described on the basis of the drawings.

FIRST EMBODIMENT

A video signal switching device in a first embodiment of the present invention is characterized in that selection and switch for inputted video signals can be executed only by a manual operation.

Figure 1:
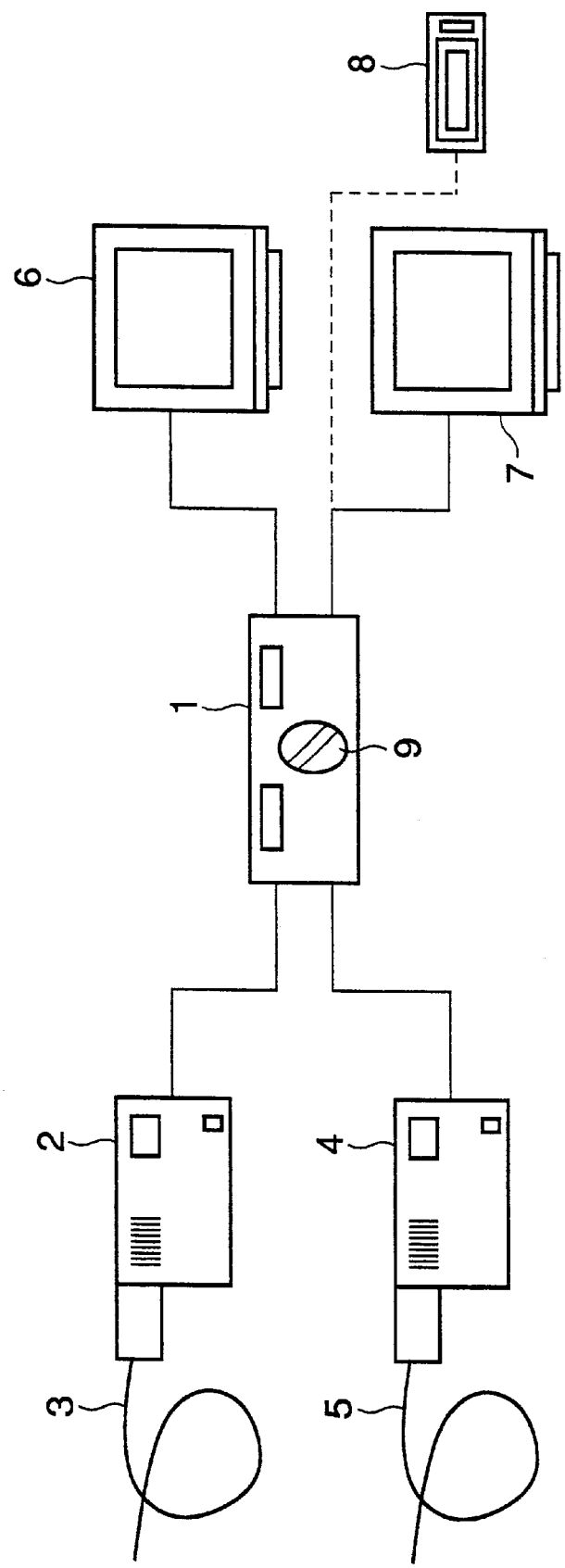
FIG. 1 is a schematic view of an endoscope system in a first embodiment of the present invention.

FIG. 1 shows the schematic construction of an endoscope system using the video signal switching device in the first embodiment. In FIG. 1, a video endoscope 3 performs a photographing operation in a field sequential system and inputs a CCD output in the field sequential system to the video processor device 2. This video processor device 2 is provided with a light source device in which respective color filters are inserted into an emitting light pass in order of red, green and blue, a light connector socket into which a light connecter of the video endoscope 3 is inserted and connected, a signal connector socket into which a signal conector of the video endoscope 3 is inserted and connected, a signal processing circuit which converts a CCD output signal in field sequential system inputted through the signal connector socket into a video signal (NTSC composite signal) with reference to a color of a filter inserted in the emitting light pass, and an output terminal connected to an output terminal of the signal processing circuit. The color filters can be escaped from the emiting light path in the light source device. When the color filters are escaped from the emitting light path, a fiber scope can be connected to the light connector socket of the video processor device 2, so that this video processor device 2 can be also used as a light source device for the fiber scope. In this case, no video signal is outputted from the video processor device 2.

In FIG. 1, a video endoscope 5 is provided with a color CCD of color mosaic system therein and inputs a CCD output signal in color mosaic system obtained by the color CCD picking-up a image into the video processor device 4. This video processor device 4 is provided with a light source device emitting white light, a light connector socket into which a light connecter of the video endoscope 5 is inserted and connected, a signal connector socket into which a signal conector of the video endoscope 5 is inserted and connected, a signal processing circuit which converts a CCD output signal in color mosaic system system inputted through the signal connector socket into a NTSC composite signal, and an output terminal connected to an output terminal of the signal processing sircuit. A fiber scope can be connected to the light connector socket of the video processor device 4, so that the video processor device 4 can be also used as a light source device for the fiber scope. In this case, no video signal is outputted from the video processor device 4.

The output terminal of the video processor device 2 and the output terminal of the video processor device 4 are respectively connected to two video input terminals of the video signal switching device 1. The video signal switching device 1 selects any one video signal among video signals inputted through the respective video input terminals in accordance with a rotational position of a switching dial 9 arranged on a front face of the video signal switching device and outputs the selected video signal through two video output terminals. A concrete construction of this video signal switching device 1 will be explained later in detail. Television monitors 6, 7 can be respectively connected to the two video output terminals of this video signal switching device 1. Each of these television monitors 6, 7 has a video input terminal for an NTSC composite signal and displays a moving image based on the video signal (NTSC composite signal) inputted through this video input terminal. Only one of the television monitors 6, 7 may be connected to the video signal switching device 1. Further, a video recorder 8 may be connected to the video signal switching device 1 instead of one of the monitor devices 6, 7.

Figure 2:
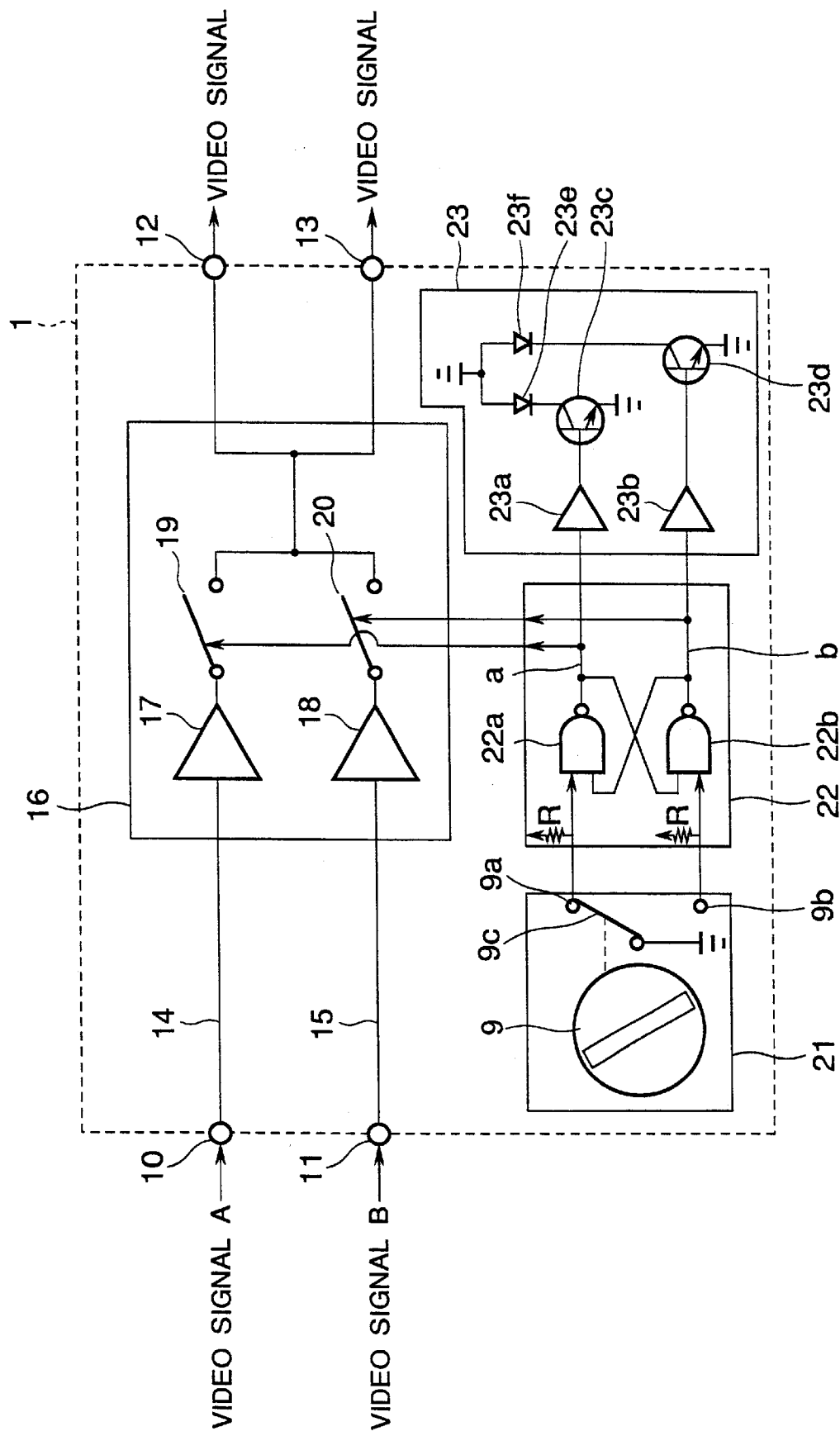
FIG. 2 is a circuit diagram of a main portion of a video signal switching device of FIG. 1.

FIG. 2 is a circuit diagram showing the circuit construction of a main portion of the video signal switching device 1. As shown in this FIG. 2, a video input terminal 10 connectable to the output terminal of one of the video processor devices 2, 4 and a video input terminal 11 connectable to the output terminal of the other of the video processor devices 2, 4 are selectively connected to two video output terminals 12, 13 by a connecting switching device 16.

The connecting switching device 16 comprises buffer amplifiers 17, 18 each having functions of a buffer and an amplifier, and video change-over switches 19, 20 respectively connected to these buffer amplifiers 17, 18. More specifically, the video input terminal 10 is connected to an input terminal of the buffer amplifier 17 through a signal line 14. One end of the video change-over switch 19 is connected to an output terminal of the buffer amplifier 17. Similarly, the video input terminal 11 is connected to an input terminal of the buffer amplifier 18 through a signal line 15. One end of the video change-over switch 20 is connected to an output terminal of the buffer amplifier 18. Each of these video change-over switches 19, 20 comprises an analog transistor switch such as a FET, etc. or a relay. In accordance with switching signals a, b applied to their control terminals (that is, gate terminals in case that the video change-over switches comprises an FET), the video change-over switches 19, 20 are closed when the switching signals a, b have high potential. In contrast to this, the video change-over switches 19, 20 are opened when the switching signals a, b have low potential. The other ends of these video change-over switches 19, 20 are connected to each other and are connected to both the video output terminals 12, 13. The video change-over switches 19, 20 may be respectively constructed as one function of buffer amplifiers 17, 18 of which enable terminals are inputted with the switching signals a, b.

Further, a manual change-over switch 21, a flip flop 22 and an indicator 23 are built in the video signal switching device 1. This manual change-over switch 21 is comprises the above-mentioned switching dial 9 and a switching brush 9c selectively comes in contact with the contacts 9a and 9b in accordance with the rotational position of the switching dial 9. This switching brush 9c is connected to the ground. Each of the contacts 9a, 9b is pulled up through a resistor R and is connected to one input terminal of NAND circuit 22a, 22b constituting the flip flop 22. Output terminal of each NAND circuits 22a, 22b is connected to the other input terminal of the other NAND circuit 22a, 22b. The output terminal of the NAND circuit 22a is also connected to the control terminal of the video change-over switch 19, so that the output signal of the NAND circuit 22a is applied to this control terminal as the switching signal a. Similarly, the output terminal of the NAND circuit 22b is also connected to the control terminal of the video change-over switch 20, so that the output signal of the NAND circuit 22b is applied to this control terminal as the switching signal b.

By virtue of such a construction of the manual change-over switch 21, the flip flop 22 and the connecting switching circuit 16, when the switching brush 9c is contacted to the contact 9a, low potential is inputted to one input terminal of the NAND circuit 22a, so that the potential of the switching signal a becomes high and the video change-over switch 19 is closed. IN this time, high potentials are respectively inputted to both the input terminals of the NAND circuit 22b, so that the potential of the switching signal b becomes low and the video change-over switch 20 is opened. As a result, a video signal A inputted through the video input terminal 10 is outputted through both the output terminals 12 and 13. In contrast to this, when the switching brush 9c is contacted to the contact 9b, a low potential is inputted to the one input terminal of the NAND circuit 22b, so that the potential of the switching signal b becomes high and the video change-over switch 20 is closed. In this time, high potential is respectively inputted to both the input terminals of the NAND circuit 22a, so that the potential of the switching signal a becomes low and the video change-over switch 19 is opened. As a result, a video signal B inputted through the video input terminal 11 is outputted through both the output terminals 12 and 13. States of the respective portions and the respective signals explained above are summarized in the following table 1.

TABLE 1

| Switching brush 9c | Switching signal a | Switching signal b | Video change-over switch 19 | Video change-over switch 20 |
|---|---|---|---|---|
| Terminal 9a | H | L | ON | OFF |
| Terminal 9b | L | H | OFF | ON |

The indicator 23 comprises a buffer 23a, a switching transistor 23c, an LED 23e, a buffer 23b, a switching transistor 23d and an LED 23f. The buffer 23a is connected to the output terminal of the NAND circuit 22a. The switching transistor 23c has a base connected to an output terminal of the buffer 23a and an emitter connected to the ground. The LED 23e is connected between a collector of the switching transistor 23c and a power source. The buffer 23b is connected to the output terminal of the NAND circuit 22b. The switching transistor 23d has a base connected to an output terminal of the buffer 23b and an emitter connected to the ground. The LED 23f is connected between a collector of this switching transistor 23d and the power source. Accordingly, when the switching signal a has high potential, the switching transistor 23c is turned on, so that the LED 23e irradiates. When the switching signal b has high potential, the switching transistor 23d is turned on, so that the LED 23f irradiates.

An operation of the video signal switching device 1 in the first embodiment constructed as above will next be explained. Since the switching brush 9c is connected to the ground, the potential inputted to the NAND circuit 22a of the flip flop 22 is low and the potential inputted to the NAND circuit 22b the flip flop 22 is high when the switching brush 9c is switched over to contact to the contact 9a by operation of the switching dial 9. As a result, the switching signal a has high potential and the switching signal b has low potential on an output side of the flip flop 22. Thus, as shown in the table 1, the video change-over switch 19 is closed and the video change-over switch 20 is opened. Accordingly, a video signal A inputted through the input terminal 10 is outputted to the television monitor 6 connected to the output terminal 12 and is also outputted to the television monitor 7 connected to the output terminal 13. When the switching brush 9c is switched over to come in contact the contact 9b, in contrast to the above case, the switching signal a has low potential and the switching signal b has high potential, so that the video change-over switch 19 is opened and the video change-over switch 20 is closed. Accordingly, a video signal B inputted through the input terminal 11 is outputted to the television monitor 6 connected to the output terminal 12 and is also outputted to the television monitor 7 connected to the output terminal 13. Thus, when the video signals are transmitted through both the signal lines 14 and 15, only one of the video signals is selected by operation of the switching dial 9 and is outputted to the television monitors 6, 7. When the video signal is transmitted through only one of the signal lines 14 and 15, this video signal is outputted to the television monitors 6, 7 by the switching dial 9 switched over to the corresponding signal line transmitting the video signal.

Besides, when the switching signal a has a high potential by operation of the switching dial 9, an output signal of the buffer 23a also has high potential, so that the switching transistor 23c is turned on and the LED 23e irradiates. In contrast to this, when the switching signal b has high potential by operation of the switching dial 9, an output signal of the buffer 23b also has high potential, so that the switching transistor 23d is turned on and the LED 23f irradiates. Thus, since only one of the LEDs 23e, 23f of the indicator 23 irradiates in accordance with operation of the switching dial 9, it is possible to easily confirm which one of the video signals transmitted through the respective signal lines 14, 15 is outputted to the television monitors 6, 7.

In FIG. 2, it is a premise that each of the video signals is a NTSC composite signal. Accordingly, one signal line 14 and one signal line 15 are arranged and only one connecting switching device 16 is arranged. However, each of the video signals may be a YCC separating signal. In such a case, the input terminals 10, 11, the signal lines 14, 15, the connecting switching device 16 and the output terminals 12, 13 are arranged for every brightness signal and each color difference signal. Similarly, each of the video signals may be an RGB component signal. In such a case, the input terminals 10, 11, the signal lines 14, 15, the connecting switching device 16 and the output terminals 12, 13 are arranged for each of red (R), green (G) and blue (B) color signals and a synchronous signal, respectively. In these cases plural connecting switching devices 16 are thus arranged in parallel with each other, the same switching signal a is applied to video change-over switches 19 of all the connecting switching devices 16 and the same switching signal b is also applied to video change-over switches 20 of all the connecting switching devices 16.

SECOND EMBODIMENT

Figure 3:
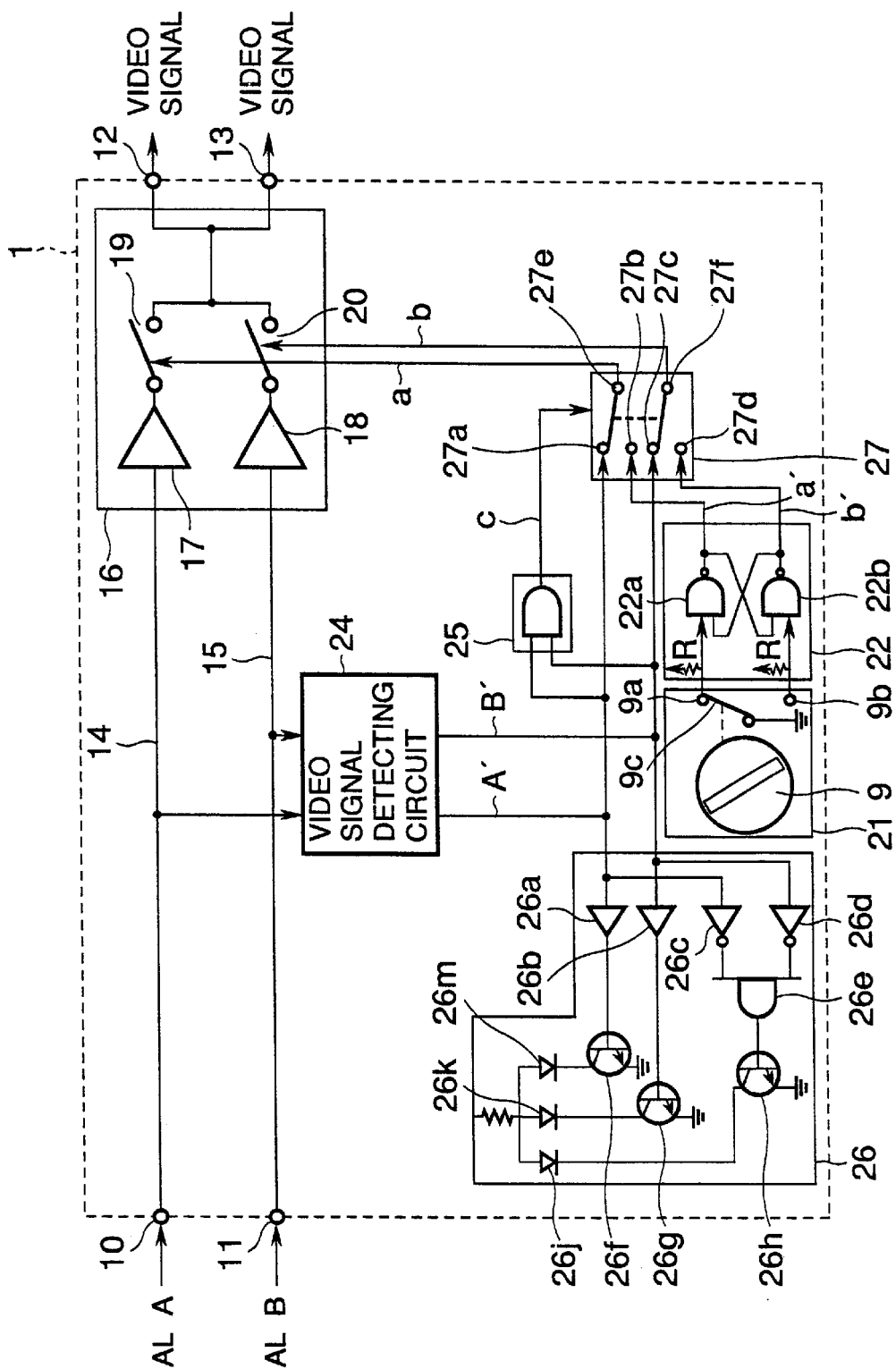
FIG. 3 is a circuit diagram of a main portion of a video signal switching device in a second embodiment of the present invention.

The video signal switching device in a second embodiment of the present invention is characterized in the the following construction. Namely, a signal line not transmitting a video signal therethrough is automatically discriminated from a signal line transmitting the video signal therethrough, and only video change-over switches 19, 20 connected to the signal line transmitting the video signal therethrough are automatically closed, when no video processor device is connected to one of the video input terminals 10, 11, when a video processor device connected to one of the video input terminals 10, 11 is not operated, or when a fiber scope is connected to the video processor device connected to one of the video input terminals 10, 11. Therefore, as shown in FIG. 3, the video signal switching device 1 in the second embodiment 1 differs from the video signal switching device 1 in the above first embodiment in the points that there is no indicator 23 of the construction as shown in FIG. 2, that the flip flop 22 is connected to the connecting switching device 16 through an automatic-manual change-over switch 27, and that a video signal detecting circuit 24, an AND circuit 25 and an indicator 26 of the construction as shown in FIG. 3 are arranged. The remaining constructions (namely, the respective video input terminals 10, 11, the respective signal lines 14, 15, the connecting switching device 16, the respective video output terminals 12, 13, the manual change-over switch 21 and the flip flop 22) are common in the first and second embodiments. Accordingly, an explanation of these constructions is omitted in the following description.

FIG. 3 is a circuit diagram showing the circuit construction of a main portion of the video signal switching device 1 in the second embodiment. As shown in this FIG. 3, the signal line 14 connected to the video input terminal 10 is branched in its intermediate portion and is connected to the video signal detecting circuit 24. The signal line 15 connected to the video signal input terminal 11 is also branched in its intermediate portion and is connected to the video signal detecting circuit 24. This video signal detecting circuit 24 has a function for detecting existence or nonexistence of a video signal transmitted through each of the signal lines 14, 15.

Figure 4:
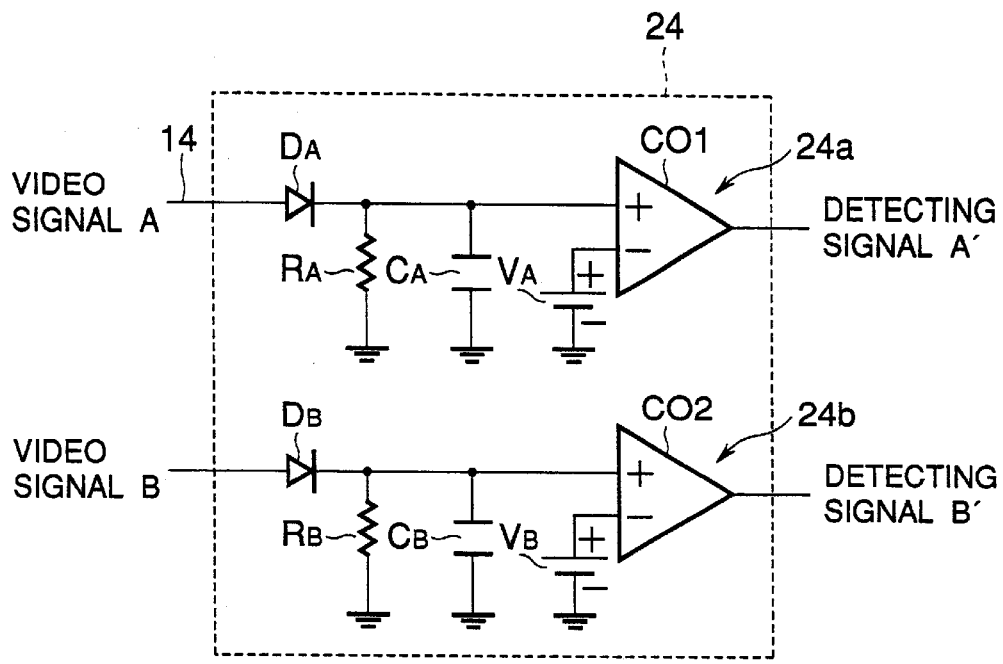
FIG. 4 is a circuit diagram showing the construction of a video signal detecting circuit.

As shown in FIG. 4, the video signal detecting circuit 24 comprises a first detecting circuit 24a for detecting existence or nonexistence of a video signal A transmitted through the signal line 14 and a second detecting circuit 24b for detecting existence or nonexistence of a video signal B transmitted through the signal line 15. The detecting circuit 24a comprises a diode DA, an integral circuit and a comparator CO1. The diode DA has an anode connected to the signal line 14. The integral circuit comprises a discharging resistor RA connecting a cathode of this diode DA to the ground and a capacitor CA arranged in parallel with the discharging resistor RA. An output signal of the integral circuit (namely, a voltage of the capacitor CA) is inputted to a plus (+) input terminal of the comparator CO1 and a constant voltage VA is inputted to a minus (−) input terminal of the comparator CO1. Similarly, the detecting circuit 24b comprises a diode DB, an integral circuit and a comparator CO2. The diode DB has an anode connected to the signal line 15. The integral circuit comprises a discharging resistor RB connecting a cathode of this diode DB to the ground and a capacitor CB arranged in parallel with this discharging resistor RB. An output signal of the integral circuit (namely, a voltage of the capacitor CB) is inputted to a plus (+) input terminal of the comparator CO2 and a constant voltage VB is inputted to a minus (−) input terminal of the comparator CO2.

Figure 5:
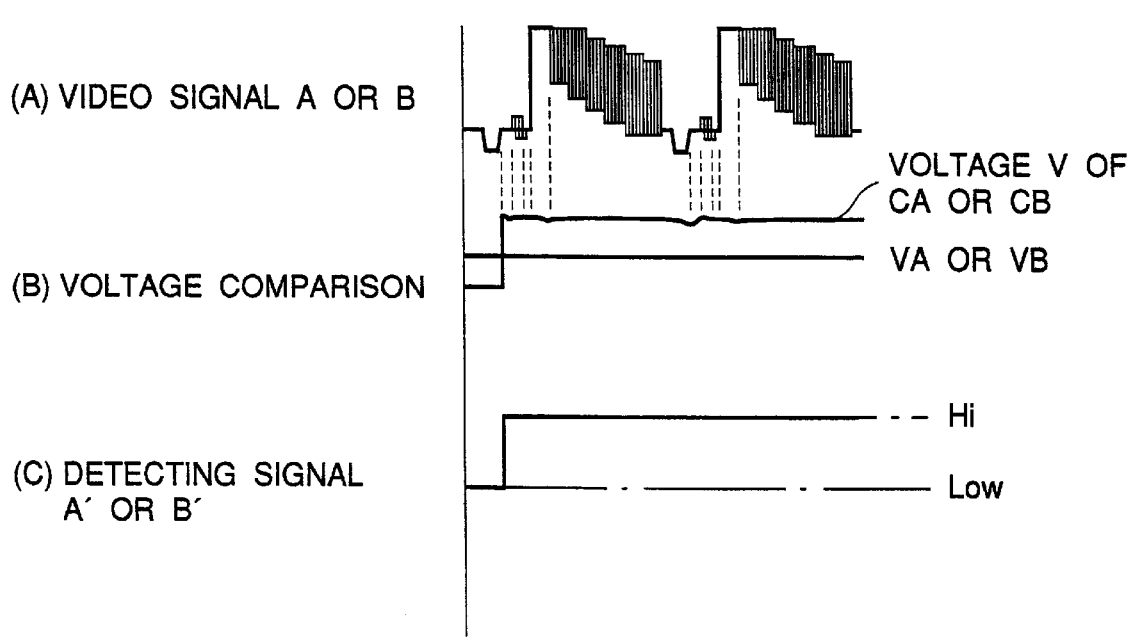
FIG. 5 is a graphical representation showing a video signal in the video signal detecting circuit.

A time constant determined by a resistance value of the discharging resistor RA and a capacity of the capacitor CA is set to be sufficiently longer than one vertical synchronous period of the video signals A, B shown in FIG. 5(a). As shown in FIG. 5(b), the comparators CO1, CO2 respectively compare voltages V of the capacitors CA, CB with reference voltages VA, VB. As shown in FIG. 5(c), when the voltages V of the capacitors CA, CB are respectively higher than the reference voltages VA, VB, high potential is outputted as detecting signals A', B'. In contrast to this, when the voltages V of the capacitors CA, CB are respectively lower than the reference voltages VA, VB, low potentials are outputted as detecting signals A', B'. The relation of the respective signals explained above is summarized in the following table 2.

TABLE 2

| Video signal A | Video signal B | Detecting signal A' | Detecting signal B' |
| --- | --- | --- | --- |
| Nonexistence | Nonexistence | Low | Low |
| Nonexistence | Existence | Low | High |
| Existence | Nonexistence | High | Low |
| Existence | Existence | High | High |

The detecting signals A', B' outputted from the comparators CO1, CO2 of the video signal detecting circuit 24 are respectively inputted to the AND circuit 25, the automatic-manual change-over switch 27 and the indicator 26.

The AND circuit 25 outputs an AND output signal C showing logical AND of the detecting signals A', B' to control a switching operation of the automatic-manual change-over switch 27.

The automatic-manual change-over switch 27 comprises a first switch and a second switch. The first switch comprises contacts 27a, 27b and a switching piece 27e selectively electrically contacted to the contacts 27a, 27b. The second switch comprises contacts 27c, 27d and a switching piece 27f selectively electrically contacted to the contacts 27c, 27d. Each of these first and second switches is constructed as a relay or a multiplexer controlled by an AND output signal C of the AND circuit 25. Concretely, when the AND output C of the AND circuit 25 has high potential, the switching piece 27e is electrically contacted to the contact 27b and the switching piece 27f is electrically contacted to the contact 27d. In contrast to this, when the AND output signal C of the AND circuit 25 has low potential, the switching piece 27e is electrically contacted to the contact 27a and the switching piece 27f is electrically contacted to the contact 27c. The detecting signal A' outputted from the video signal detecting circuit 24 is also applied to the contact 27a and the detecting signal B' is also applied to the contact 27c. Output signals a', b' of the flip flop 22 having the same construction as that of the first embodiment are also inputted to the automatic-manual change-over switch 27. More specifically, the output signal a' of the NAND circuit 22a is applied to the contact 27b and the output signal b' of the NAND circuit 22b is applied to the contact 27d. One of the detecting signal A' and the output signal a' of the NAND circuit 22a which is selected by the switching piece 27e is applied to the control terminal of the video change-over switch 19 as a switching signal a. One of the detecting signal B' and the output signal b' of the NAND circuit 22b which is selected by the switching piece 27f is applied to the control terminal of the video change-over switch 20 as the switching signal b. The relation of states of the respective detecting signals A', B' and state of the respective video change-over switches 19, 20 explained above is summarized in the following table 3.

TABLE 3

| Detecting signal A' | Detecting signal B' | Video change-over switch 19 | Video change-over switch 20 |
|---|---|---|---|
| Low | Low | OFF | OFF |
| Low | High | OFF | ON |
| High | Low | ON | OFF |

When both the detecting signals A', B' have high potential, the output signals a', b' of the respective NAND circuits 22a, 22b controlled by the change-over switch 9 (switching piece 9c) are applied to the control terminals of the respective video change-over switches 19, 20 as switching signals a, b as they are. The following table 4 summarizes the relation of a position of the switching piece 9c, the output signals a', b' of the respective NAND circuits 22a, 22b and states of the respective video change-over switches 19, 20 when both the detecting signals A', B' have high potential.

TABLE 4

| Switching piece 9c | NAND 22a | NAND 22b | Video change-over switch 19 | Video change-over switch 20 |
|---|---|---|---|---|
| Contact 9a | H | L | ON | OFF |
| Contact 9b | L | H | OFF | ON |

The indicator 26 comprises two buffers 26a, 26b, two inverters 26c, 26d, three switching transistors 26f, 26g, 26h, three LEDs 26j, 26k, 26m and an AND circuit 26e. The detecting signal A' is inputted to the buffer 26a and the inverter 26c. The detecting signal B' is inputted to the buffer 26b and the inverter 26d. The switching transistor 26f has a base connected to an output terminal of the buffer 26a and an emitter connected to the ground. The LED 26m is connected between a collector of the switching transistor 26f and a power source. The switching transistor 26g has a base connected to an output terminal of the buffer 26b and an emitter connected to the ground. The LED 26k is connected between a collector of the switching transistor 26g and the power source. The AND circuit 26e outputs an AND of output signals of both the inverters. The switching transistor 26h has a base connected to an output terminal of the AND circuit 26e and an emitter connected to the ground. The LED 26j is connected between a collector of the switching transistor 26h and the power source. Accordingly, when only the detecting signal A' has high potential, the switching transistor 26f is turned on, so that the LED 23m irradiates. When only the detecting signal B' has a high potential, the switching transistor 26g is turned on so that the LED 26k irradiates. When both the detecting signals A', B' have low potential, an output signal of the AND circuit 26e has high potential, so that the switching transistor 26h is turned on and the LED 26j is thereby irradiates. In contrast to this, both the LEDs 26m and 26k irradiates, when both the detecting signals A', B' have high potential, namely, when operations of the respective video change-over switches 19, 20 are controlled in accordance with the rotational position of the switching dial 9.

An operation of the video signal switching device 1 in the second embodiment constructed as above will next be explained. When a video signal is transmitted through only one of the signal lines 14, 15, or when no video signal is transmitted through both the signal lines 14, 15, at least one of the detecting signals A', B' has low potential as can be seen from the table 2. Accordingly, the AND output signal C from the AND circuit 25 has a low potential. When this AND output signal C has low potential, the switching piece 27e of the automatic-manual change-over switch 27 is electrically contacted to the contact 27a and the switching piece 27f is electrically contacted to the contact 27c. For example, when only the detecting signal A' has high potential, the video change-over switch 19 is turned on and the video change-over switch 20 is turned off as shown in the table 3, so that the signal line 14 is connected to the video output terminals 12, 13. Conversely, when only the detecting signal B' has high potential, the video change-over switch 19 is turned off and the video change-over switch 20 is turned on, so that the signal line 15 is connected to the video output terminals 12, 13. More specifically, when the video signal is transmitted to one of the signal lines 14, 15, the one signal line transmitting this video signal therethrough is automatically selected and is connected to each of the video output terminals 12, 13 and the video signal is outputted to the television monitors 6, 7 through the respective video output terminals 12, 13.

In contrast to this, when video signals are transmitted to both the signal lines 14, 15, the AND output signal C from the AND circuit 25 has high potential. When the AND output signal C has high potential, the switching piece 27e of the automatic-manual change-over switch 27 is contacted to the contact 27b and the switching piece 27f is contacted to the contact 27d. More specifically, the flip flop 22 and the respective video change-over switches 19, 20 are connected to each other. In this state, for example, when the switching brush 9c is switched over to contact to the contact 9a in accordance with the rotational position of the switching dial 9, the potential inputted to the flip flop 22 is low on a side connected to the contact 9a and is high on a side connected to the contact 9b, since the switching brush 9c is connected to the ground. As a result, the output signal a' of the NAND circuit 22a of the flip flop 22 has high potential and the output signal b' of the NAND circuit 22b has low potential. Thus, as shown in the table 4, the video change-over switch 19 is turned on and the video change-over switch 20 is turned off, so that the signal line 14 is connected to the video output terminals 12, 13. When the switching brush 9c is switched over to contact to the contact 9b, the output signal a' of the NAND circuit 22a conversely has low potential and the output signal b' of the NAND circuit 22b has high potential. Thus, the video change-over switch 19 is turned off and the video change-over switch 20 is turned on, so that the signal line 15 is connected to the video output terminals 12, 13. Thus, when the video signals are transmitted to both the signal lines 14 and 15, one of the video signals is selected in accordance with the rotational position of the switching dial 9 and is outputted to the television monitors 6, 7 through the video output terminals 12, 13.

When the video signal is transmitted to the signal line 14, the detecting signal A' has high potential and an output signal of the buffer 26a has high potential, so that the switching transistor 26f is turned on and the LED 26m irradiates. When the video signal is transmitted to the signal line 15, the detecting signal B' has high potential and an output signal of the buffer 26b has high potential so that the switching transistor 26g is turned on and the LED 26k irradiates. When the video signals are transmitted to both the signal lines 14 and 15, the LEDs 26m and 26k irradiate. When no video signal is transmitted to each of the signal lines 14, 15, output signals of both the inverters 26c and 26d have high potential and the output signal of the AND circuit 26e has high potential, so that only the LED 26j irradiates. Therefore, an operator can easily know the signal lines 14, 15 to which a video signal is transmitted, by confirming irradiating states of the LEDs 26j, 26k, 26m of the indicator 26.

Figure 6:
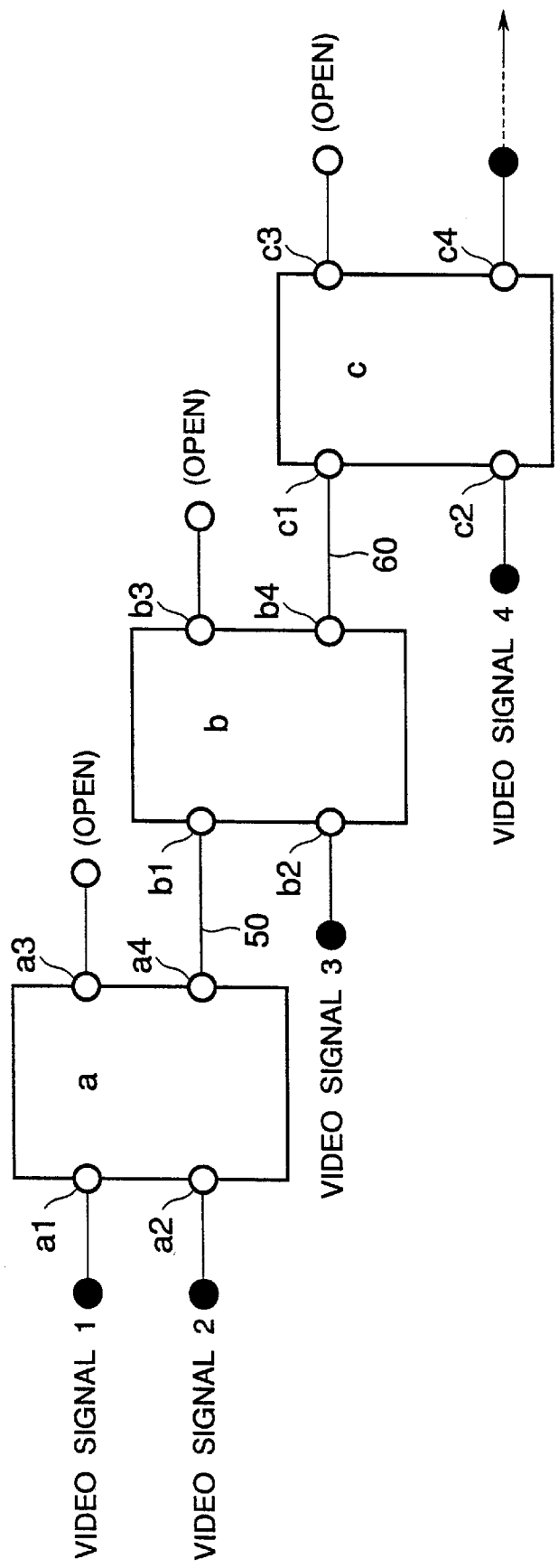
FIG. 6 is a block diagram showing a multistage connection of the video signal switching device in the second embodiment.

Two video input terminals 10, 11 and two video output terminals 12, 13 are arranged in the video signal switching device 1 shown in FIG. 3. Three or more video input terminals and three or more video output terminals may be arranged. However, in this case, there is a defect of an increase in size of a device body. Therefore, in the video signal switching device 1 in the second embodiment of the present invention, the number of video input terminals is set to two and the number of video output terminals is also set to two. However, it is necessary to connect two or more video signal switching devices 1 to each other at multiple stages when there are video signals from three or more video processor device. For example, when four video processor devices are to be arranged, three video signal switching devices are connected to each other at three stages as shown in FIG. 6. Namely, a video output terminal a4 of a video signal switching device a at first stage is connected to a video input terminal b1 of a video signal switching device b at second stage through a cable 50. Further, a video output terminal b4 of the video signal switching device b at the second stage is connected to a video input terminal c1 of a video signal switching device c at third stage through a cable 60. Video output terminals a3, b3, c3 at the respective stages are set to be opened. In such an endoscope system, impedance is changed by lengths of the cables 50, 60. However, as long as impedance matching is made in every stage, no unnecessary reflecting signal (a high frequency signal, etc.) is caused and a video signal can be stably transmitted. Further, as shown in FIG. 6, the number of monitors can be simply increased with respect to one video signal by arranging the video signal switching devices 1 at multiple stages. With respect to signal lags (delay times) caused by arranging the video signal switching devices 1 at the multiple stages, all signals relating to a picture image are delayed by the same time and are synchronized with each other. Accordingly, no picture image is disturbed.

THIRD EMBODIMENT

The video signal switching device in a third embodiment of the present invention is characterized in that a video signal is manually switched over by pushing-down of a specific key of a keyboard 31 instead of the switching dial 9 on a front face of the video signal switching device, in comparison with the second embodiment.

Figure 7:
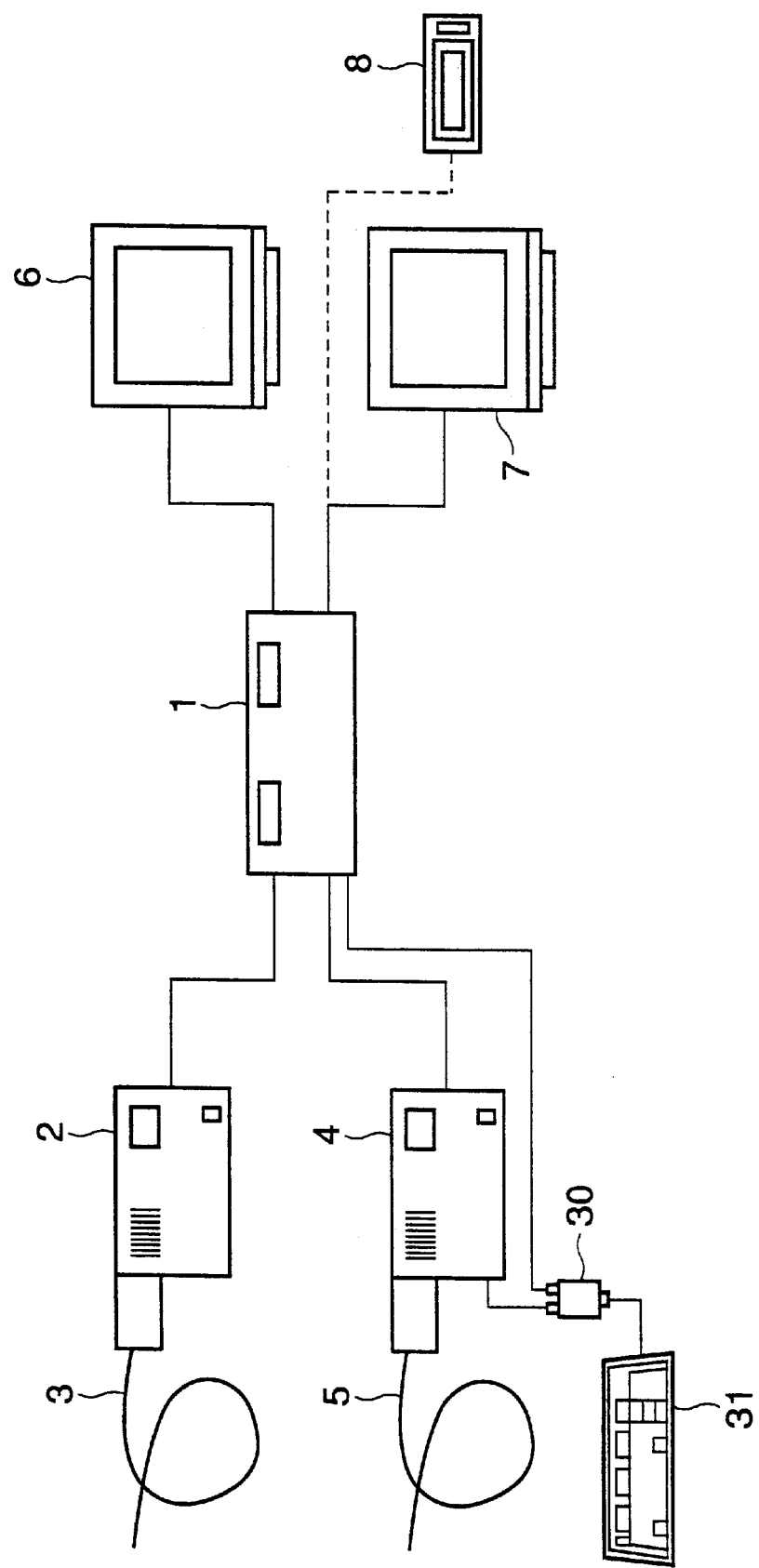
FIG. 7 is a schematic view of an endoscope system in a third embodiment of the present invention.

FIG. 7 shows the schematic construction of an endoscope system using the video signal switching device 1 in the third embodiment of the present invention. The construction of the endoscope system in the third embodiment shown in FIG. 7 differs from that of the endoscope system shown in FIG. 1 in the points that the keyboard 31 is connected to a video processor device 4 for an endoscope through a keyboard signal distributor 30 and that no switching dial is arranged on the front face of the video signal switching device 1. The keyboard 31 may be connected to a video processor device 2 for an endoscope through the keyboard signal distributor 30, or may be connected to both the video processor devices 2 and 4.

Figure 8:
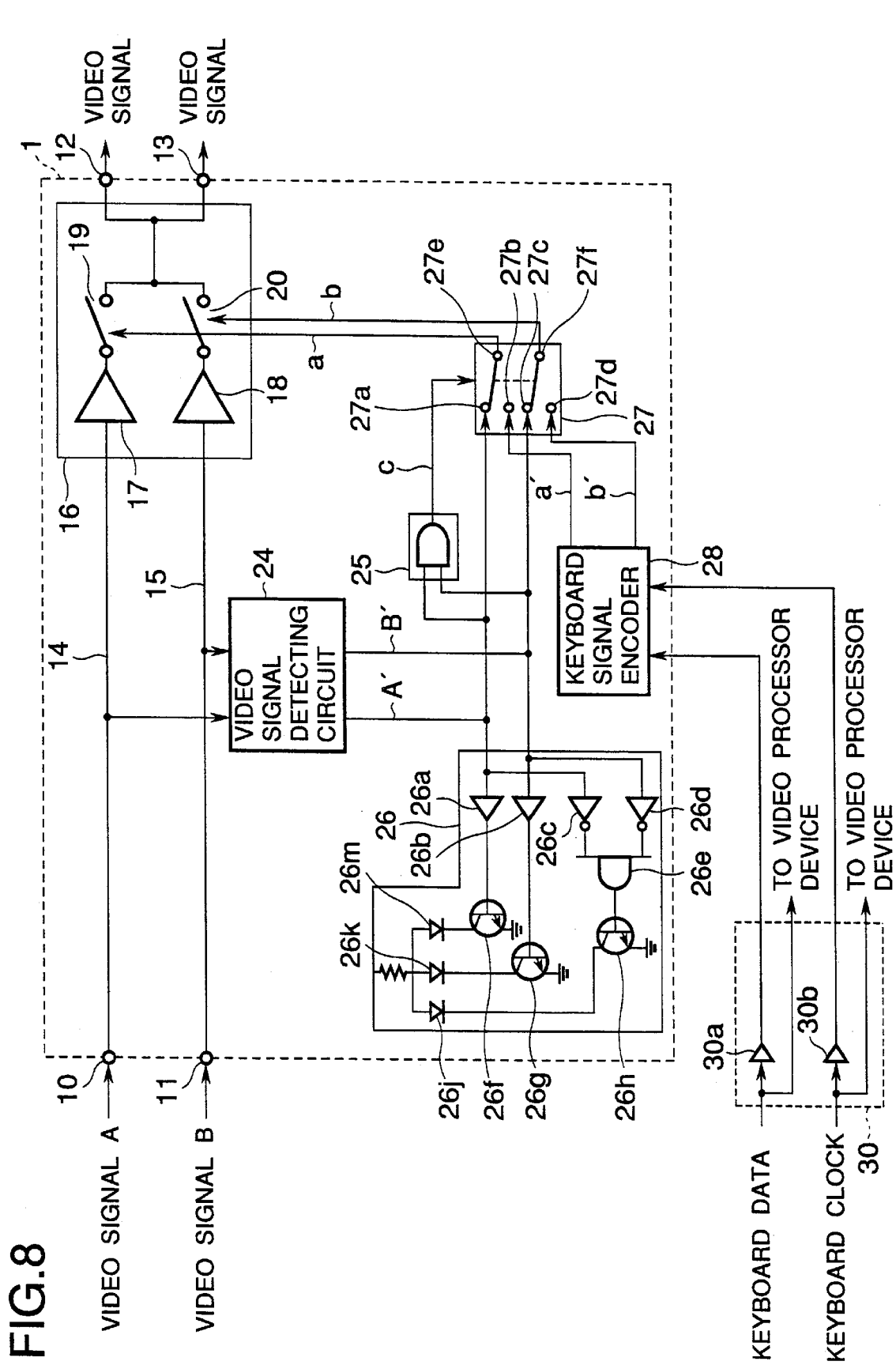
FIG. 8 is a circuit diagram of a main portion of a video signal switching device shown in FIG. 7.

FIG. 8 is a circuit diagram showing the circuit construction of a main portion of the video signal switching device 1 in the third embodiment. As shown in FIG. 8, the video signal switching device 1 in the third embodiment differs from the video signal switching device 1 in the second embodiment shown in FIG. 3 in tha point that a keyboard signal encoder 28 is arranged instead of the manual change-over switch 21 and the flip flop 22. The remaining constructions (namely, the respective video input terminals 10, 11, the respective signal lines 14, 15, the connecting switching device 16, the respective video output terminals 12, 13, the video signal detecting circuit 24, the AND circuit 25, the indicator 26 and the automatic-manual change-over switch 27) are common in the second and third embodiments. Accordingly, an explanation of these constructions is omitted in the following description.

The keyboard signal distributor 30 has buffers 30a, 30b. Keyboard data are inputted from the keyboard 31 to the buffer 30a. A keyboard clock is inputted to the buffer 30b. The keyboard signal distributor 30 has a function for distributively outputting the inputted keyboard data and the inputted keyboard clock to the keyboard signal encoder 28 and the video processor device 4.

The keyboard signal encoder 28 comprises logic circuites or a CPU. The keyboad signal encorder 28 has two output terminals and outputs high potential through one of these output terminals and low potential through from the other output terminal.

Figure 9:
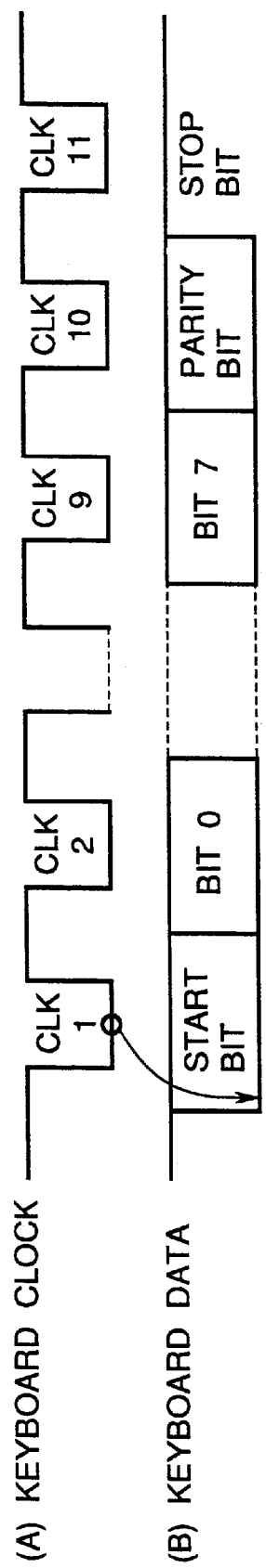
FIG. 9 is a signal chart showing a keyboard signal.
Figure 10:
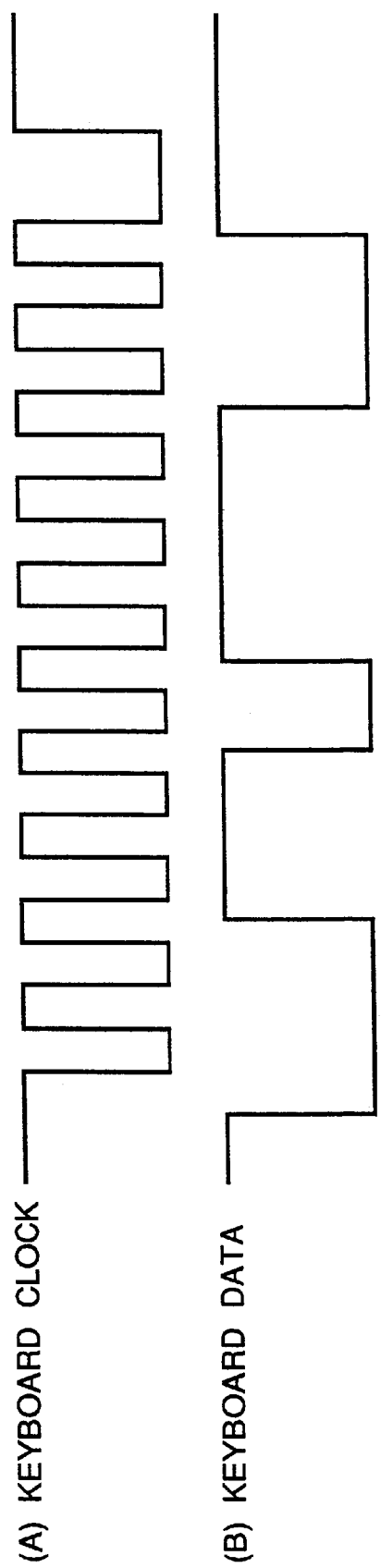
FIG. 10 is a signal chart showing the keyboard signal at a point when a key is pushed.
Figure 11:
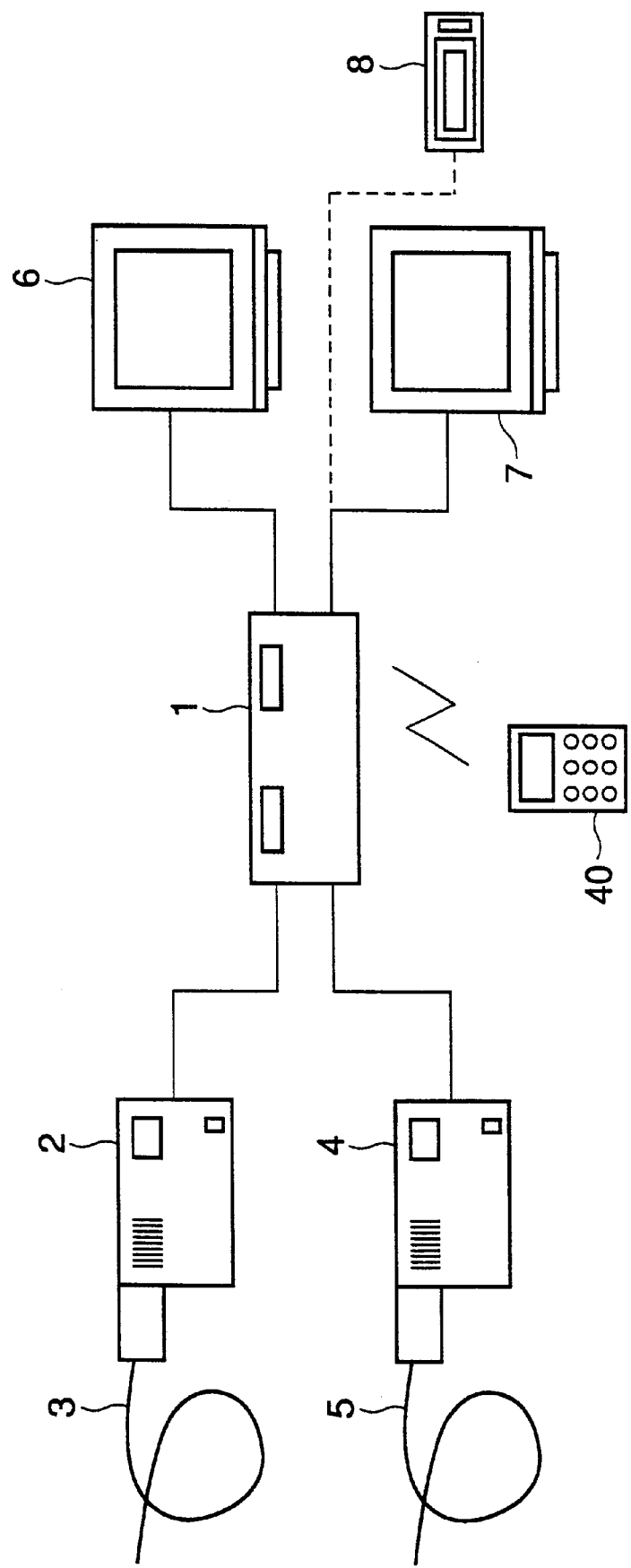
FIG. 11 is a schematic view of an endoscope system in a fourth embodiment of the present invention.

The keyboard data and the keyboard clock are inputted from the keyboard signal distributor 30 to the keyboard signal encoder 28. A keyboard signal is generally forms itself as shown in FIG. 9 and is sent with a start bit (a low potential at any time) located at its leading portion. The keyboard signal encoder 28 reads the keyboard data at a timing when the keyboard clock is changed from low potential to high potential. For example, the keyboard data outputted when an ESC key is pushed down forms itself as shown in FIG. 10. Accordingly, the keyboard signal encoder 28 reads the keyboard data of 01101110 and detects that the ESC key is pushed down.

The keyboard signal encoder 28 alternately changes over the potential of the output signal a' to be outputted through one output terminal between low and high, and alternately changes over the potential of the output signal b' to be outputted through the the other output terminal between high and low, every time the keyboard signal encoder 28 detects the keyboard data corresponding to a certain specific key. The output signal a' outputted through the one output terminal of the keyboard signal encoder 28 is inputted to the contact 27b of the automatic-manual change-over switch 27 and the output signal b' outputted through the other output terminal is inputted to the contact 27d.

An operation of the video signal switching device 1 in the third embodiment will next be explained. When a video signal is transmitted to only one of the signal lines 14, 15, or when no video signal is transmitted to both the signal lines 14, 15, one of detecting signals A', B' from the video signal detecting circuit 24 has high potential, the AND output signal C from the AND circuit 25 has low potential, so that the switching piece 27e of the automatic-manual change-over switch 27 is contacted to the contact 27a and the switching piece 27f of the automatic-manual change-over switch 27 is contacted to the contact 27c. Therefore, the detecting signals A', B' are inputted to the video change-over switch 19, 20 through the switching piece 27e, 27f, respectively. Accordingly, the signal lines 14, 15 transmitting the video signal therethrough are automatically connected to the respective video output terminals 12, 13.

On the other hand, when video signals are transmitted to both the signal lines 14 and 15, the AND output signal C from the AND circuit 25 has high potential so that the switching pieces 27e and 27f of the automatic-manual change-over switch 27 are respectively. contacted to the contacts 27b and 27d. Consequently, the keyboard signal encoder 28 and the video change-over switches 19, 20 are connected to each other. In this connecting state, the potential of the output signal a' outputted through one output terminal of the keyboard signal encoder 28 is alternately switched over between low and high and the potential of the output signal b' outputted through the other output terminal is alternately switched over between high and low, every time a certain specific key of the keyboard 31 is pushed down. Thus, one of the video change-over switches 19, 20 is turned on and the other is turned off exclusively. Accordingly, when the video signals are transmitted to both the signal lines 14 and 15, only one of the video signals is selected and is outputted to the television monitors 6, 7 in accordance with the pushing-down of the specific key of the keyboard 31.

When the video signal is transmitted through the signal line 14, the detecting signal A' has high potential, so that the output signal of the buffer 26a has high potential. Accordingly, only the switching transistor 26f is turned on and the LED 26m irradiates. When the video signal is transmitted through the signal line 15, the detecting signal B' has high potential, so that the output signal of the buffer 26b has high potential. Accordingly, only the switching transistor 26g is turned on and only the LED 26k irradiates. In contrast to this, when no video signal is transmitted through each of the signal lines 14, 15, the output signals of inverters 26c, 26d have high potential, so that the output signal of the AND circuit 26e has high potential. Accordingly, only the LED 26j irradiates.

FOURTH EMBODIMENT

The video signal switching device in a fourth embodiment of the present invention is characterized in that the video signal is manually switched over by a remote controller 40 instead of the switching dial 9 on a front face of the video signal switching device, in comparison with the second embodiment.

Figure 12:
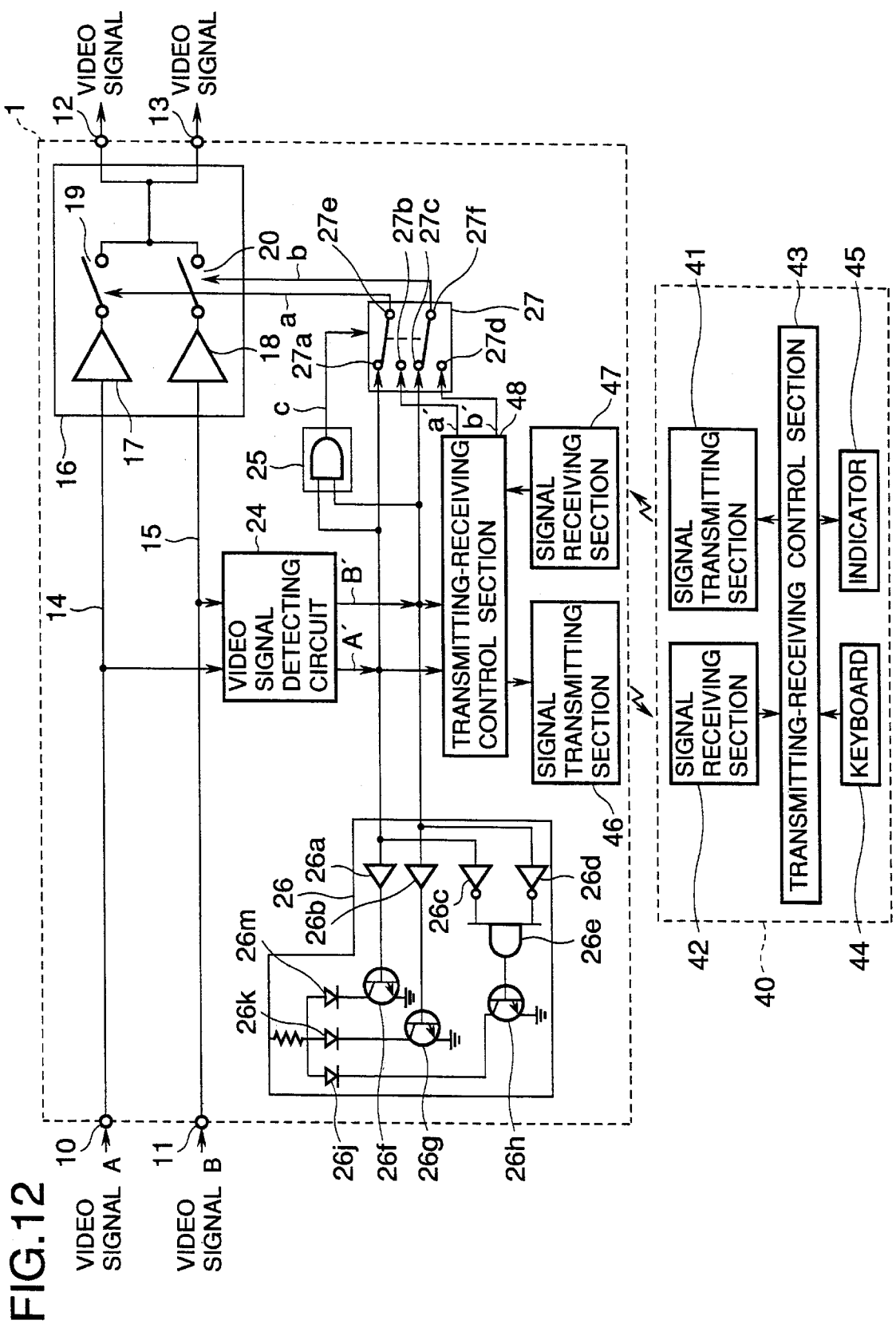
FIG. 12 is a circuit diagram of a main portion of a video signal switching device of FIG. 11.

FIG. 12 shows the schematic construction of an endoscope system using the video signal switching device 1 in the fourth embodiment of the present invention. The construction of the endoscope system in the fourth embodiment shown in FIG. 12 differs from that of the endoscope system shown in FIG. 1 in the point that the remote controller 40 wirelessly communicating with the video signal switching device 1 is arranged and that no switching dial is arranged on the front face of the video signal switching device 1.

FIG. 12 is a circuit diagram showing the circuit construction of a main portion of the video signal switching device 1 in the fourth embodiment. As shown in FIG. 12, the video signal switching device 1 in the fourth embodiment differs from the video signal switching device 1 in the second embodiment shown in FIG. 3 in the point that a signal transmitting-receiving control section 48, a signal transmitting section 46 and a signal receiving section 47 are arranged instead of the manual change-over switch 21 and the flip flop 22. The remaining constructions (namely, the respective video input terminals 10, 11, the respective signal lines 14, 15, the connecting switching device 16, the respective video output terminals 12, 13, the video signal detecting circuit 24, the AND circuit 25., the indicator 26 and the automatic-manual change-over switch 27) are common in the second and fourth embodiments. Accordingly, an explanation of these constructions is omitted in the following description.

The signal transmitting-receiving control section 48 comprises a CPU, etc. and receives the detecting signals A', B' from the video signal detecting section 24. The signal transmitting-receiving control section 48 transmits information as to whether each of these detecting signals A', B' has high or low potential to the remote controller 40 through the signal transmitting section 46. The signal transmitting-receiving control section 48 has two output terminals and outputs high potential through any one of these output terminals and low potential through the other output terminal.

The remote controller 40 comprises a signal transmitting section 41, a signal receiving section 42, a signal transmitting-receiving control section 43 connected to the signal transmitting section 41 and the signal receiving section 42, and a keyboard 44 and a display unit 45 connected to the signal transmitting-receiving control section 43. The signal transmitting-receiving control section 43 of the remote controller 40 receives information transmitted from the signal transmitting section 46 of the video signal switching device 1 through the signal receiving section 42 and the information is displayed in the display unit 45. More specifically, the display unit 45 displays information as to whether video signals are transmitted through both the signal lines 14, 15 or a video signal is transmitted through only one of these signal lines. Signals (information) are transmitted and received through radio waves or infrared rays, etc. between the signal transmitting section 41 and the signal receiving section 47, and between the signal transmitting section 46 and the signal receiving section 42.

In accordance with the fourth embodiment, when the video signals are transmitted through both the signal lines 14 and 15, similar to the case of the second embodiment, switching pieces 27e, 27f of the automatic-manual change-over switch 27 are respectively contacted to the contacts 27b, 27d, so that the signal transmitting-receiving control section 48 and the video change-over switches 19, 20 are connected to each other. At this time, if an operator selects one of the video signals transmitted through the signal lines 14, 15 and pushes a key corresponding to this selected video signal on the keyboard 44, a selecting signal corresponding to the selected video signal is sent from the signal transmitting section 41 to the signal transmitting-receiving control section 48 through the signal receiving section 47. In the signal transmitting-receiving control section 48, the potential of the output signal a' outputted through one terminal becomes high and the potential of the output signal b' outputted through the other output terminal becomes low in accordance with the selecting signal, when the signal line 14 is selected. In contrast to this, when the signal line 15 is selected, the potential of the output signal a' outputted through the output terminal becoms low and the potential of the output signal b' outputted through the other output terminal becomes high. Thus, one of the video change-over switches 19, 20 is turned on and the other is turned off exclusively.

FIFTH EMBODIMENT

Figure 13:
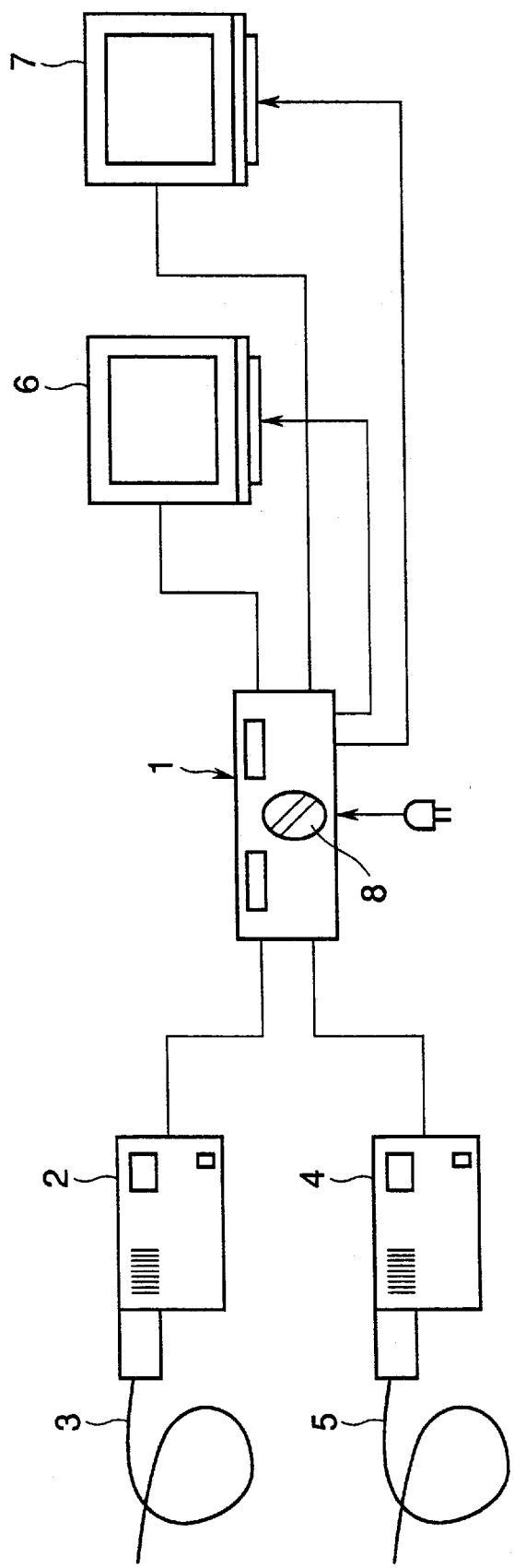
FIG. 13 is a schematic view of an endoscope system in a fifth embodiment of the present invention.
Figure 14:
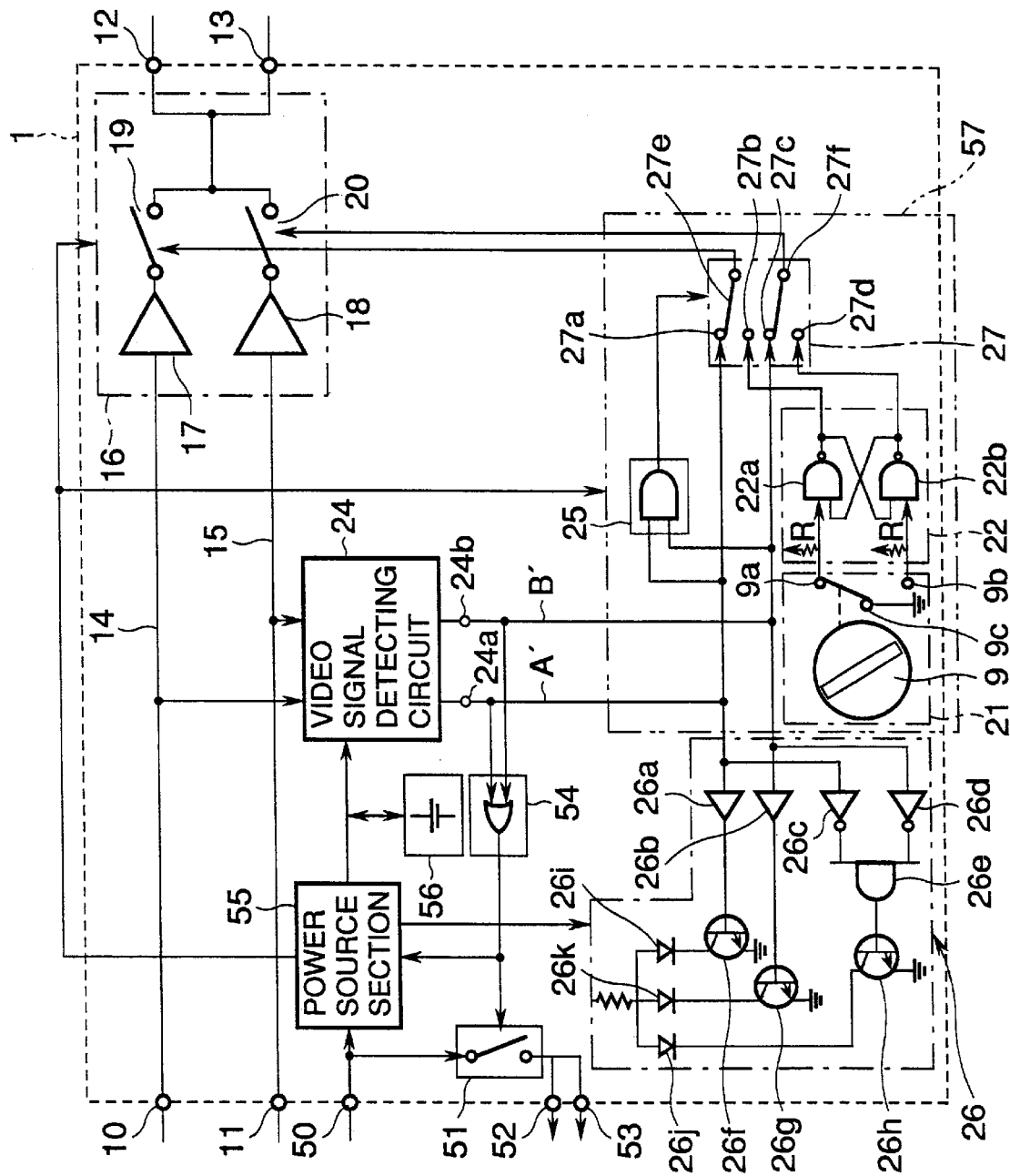
FIG. 14 is a circuit diagram of a main portion of a video signal switching device of FIG. 13.

In the system for an endoscope shown in each of the above first to fourth embodiments, the power source of each device to be used must be turned on at a starting time of operation and must be turned off after this operation is terminated. As a result, errors such as forgetting of turning-on or turning-off of the power sources, etc. tend to be caused, which makes the operation inconvenient. These turning-on and turning-off of the power sources become complicated as the number of connected television monitors is increased. The fifth embodiment of the present invention is provided to solve the complication of the turning-on and turning-off of the power sources. Accordingly, the fifth embodiment provides a video signal switching device 1 in which a power source of this video signal switching device 1 itself and the power source of a device connected to a video output terminal of this video signal switching device 1 can be automatically turned on when a video signal is inputted to one of video input terminals of the video signal switching device 1. Therefore, as shown in FIGS. 13 and 14, the construction of the video signal switching device 1 in the fifth embodiment differs from that of the video signal switching device 1 in the above second embodiment in tha point that a power input plug 50 and two power output plug sockets 52, 53 are arranged on an outer face of the video signal switching device 1, and that an OR circuit 54, a power supplying switch 51, a power source section 55 and a battery 56 are arranged. The other constructions (namely, the respective video input terminals 10, 11, the respective signal lines 14, 15, the connecting switching device 16, the respective video output terminals 12, 13, the manual change-over switch 21, the flip flop 22, the video signal detecting section 24, the AND circuit 25, the indicator 26 and the automatic-manual change-over switch 27) are common in the second and fifth embodiments. Accordingly, an explanation of these constructions is omitted in the following description.

In the video signal switching device 1 in the fifth embodiment, power is supplied to the power source section 55 shown in FIG. 14 through the power input plug 50 which is connected to an unshown plug socket for commercial power. This power source section 55 converts the comertial power of A.C. into the power of D.C. and supplies the power of D.C. to the connecting switching circuit 16, the video signal detecting section 24, a switching control section 57 (including the flip flop 22, the AND circuit 25 and the automatic-manual change-over switch 27), the indicator 26, and other unillustrated circuit requiring the power of D.C. while receiving an enable signal (high potential) from the OR circuit. The power input plug 50 is connected to power output plug sockets 52, 53 for supplying the conercial power of A.C. to television monitors 6, 7 through the power supplying switch section 51.

The video signal detecting section 24 outputs the detecting signal A' (having high potential when a video signal is transmitted through the signal line 14) through an output terminal 24a corresponding to the signal line 14 and the detecting signal B' (having high potential when the video signal is transmitted through the signal line 15) through an output terminal 24b corresponding to the signal line 15 by detecting whether or not a video signal is transmitted through each of the signal lines 14, 15. Each of these detecting signals A', B' is inputted to the AND circuit 25, the automatic-manual change-over switch 27, the indicator 26 and the OR circuit 54. This OR circuit 54 outputs an OR output signal showing logical OR of both the detecting signals A' and B'. This OR output signal is inputted to the power source section 55 as the enable signal and is also inputted to the power supplying switch section 51 as a control signal. This power supplying switch section 51 is constructed of a relay and can close a circuit between the power output plug sockets 52, 53 and the power input plug 50 to supply the power of A.C. to the television monitors 6, 7 connected to these power output plug sockets 52, 53 only when the control signal has high potential.

A primary battery or a secondary battery may be used as the battery 56. When the secondary battery is used, the battery 56 is charged with power supplied by the power source section 55 during the video signal switching device 1 in motion.

In the fifth embodiment constructed as above, respective devices are connected to each other as shown in FIG. 13 and a power switch of each of the television monitors 6, 7 is turned on in advance. At this time, however, power source section 55 of the video signal switching device 1 does not yet work. Accordingly, no power is supplied to the respective television monitors 6, 7 and the respective circuits within the video signal switching device 1 except for the video signal detecting section 24. In contrast to this, power is being supplied to the video signal detecting section 24 by the battery 56. Accordingly, the video signal detecting section 24 can detect whether the video signal is transmitted through each of the signal lines 14, 15 or not.

When the video signal detecting section 24 detects that the video signal is transmitted through at least one of the signal lines 14, 15, the video signal detecting section 24 sets potential of the detecting signals A', B' outputted through corresponding terminals to high. Consequently, since the OR output signal of the OR circuit 54 has high potential, the power supplying switch section 51 is closed and power is supplied to each of the television monitors 6, 7 through each power output plug socket, so that these television monitors 6, 7 are started. Further, the power source section 55 starts to work and power is supplied to all the other circuits within the video signal switching device 1, so that all these circuits start to work and performs a control operation according to each of the detecting signals A', B'.

When the video signal transmitted through each of the signal lines 14, 15 finishes, potential of each of the detecting signals A', B' outputted through respective terminals 24a, 24b of the video signal detecting section 24 is set to low. Consequently, potential of the OR output signal of the OR circuit 54 is set to low, so that the power supplying switch section 51 is opened and the power supplied to each of the television monitors 6, 7 is shut down. As a result, the operations of these television monitors 6, 7 are stopped. Besides, the operation of the power source section 55 is also stopped and power supplied to all the circuits within the video signal switching device 1 except for the video signal detecting section 24 is shut down, so that operations of these circuits are stopped.

SIXTH EMBODIMENT

The video signal switching device in each of the above first to fifth embodiments selectively switches over only a video signal of the same kind (an NTSC composite signal, an RGB component signal or a Y/C signals). Therefore, if an RGB monitor is used to monitor the operation with high image quality and a video image is simultaneously recorded, the user must prepare a video signal switching device which switches over the RGB component signals and outputs any one RGB component signal to the RGB monitor and another video signal switching device which switches over the NTSC composite signals and outputs any one NTSC composite signal to a video recorder (VTR), respectively. In other words, if there are plural formats of video signals respectively outputted from plural video processor devices, the video signal switching device must be prepared for every format of the video signal so as to reduce the number of output device, such as monitors, video recorder, etc. In consideration of the above problems in the first to fifth embodiments, the video signal switching device in the sixth embodiment of the present invention is constructed such that the endoscope system can be simply established and that complication of the operation by an operator can be reduced.

<Construction of Endoscope System>

Figure 15:
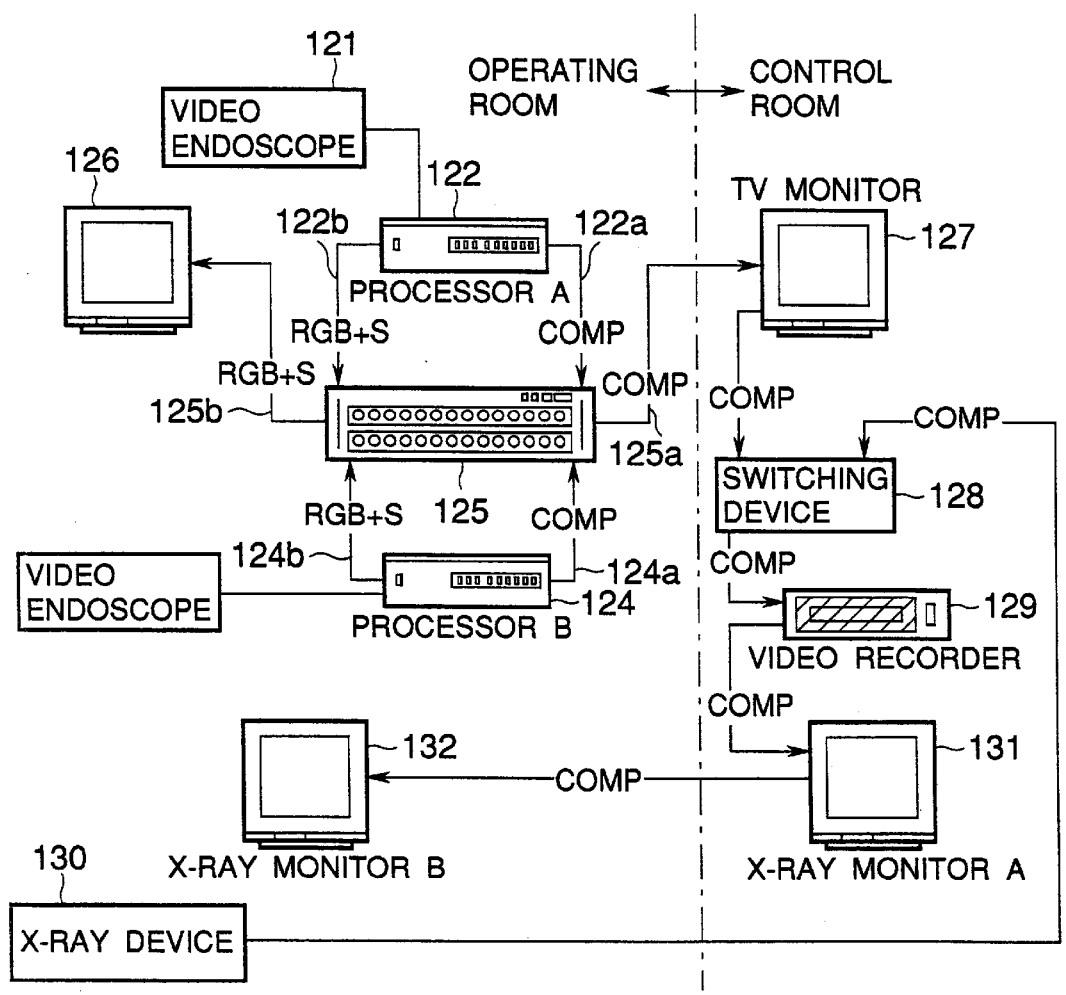
FIG. 15 is a schematic view of an endoscope system in a sixth embodiment of the present invention.

FIG. 15 is a schematic view showing an endoscope system in the sixth embodiment of the present invention. As shown in FIG. 15, a video endoscope 121 and a video processor device for the endoscope (hereinafter, simply called a "processor device") 122 belonging to a first system, and a video endoscope 123 and a processor device 124 belonging to a second system are located within an operating room. The respective processor devices 122, 124 output an NTSC composite signal through signal lines 122a, 124a and output an RGB component signal (with a synchronous signal) through signal lines 122b, 124b. Further, a video signal switching device 125 and an RGB monitor 126 are also located within the operating room. The video signal switching device 125 is connected to the processor device 122 through the signal lines 122a, 122b and is also connected to the processor device 124 through the signal lines 124a, 124b. The RGB monitor 126 is connected to the video signal switching device 125 through a signal line 125b and is commonly used in the first and second systems. The video signal switching device 125 is connected to a TV monitor 127 for video endoscopes located within a control room through a signal line 125a. Hereinafter, a monitordevice which can display a image based on an NTSC signal is demoninated a TV monitor. A switching device 128 conected to the TV monitor 127 and a video recorder (VTR) 129 connected to the switching device 128 are located within the control room.

An X-ray device 130 is also located within the operating room. The X-ray device 130 is constructed of an X-ray photographing device and a video signal generator for generating an NTSC composite signal showing a photographed object picked up by the X-ray photographing device. This X-ray device 130 is connected to the video recorder (VTR) 129 through the above switching device 128. The video recorder (VTR) 129 is connected to a TV monitor 131 for X-ray device located within the control room. The TV monitor 131 is connected to a TV monitor 132 for X-ray device located within the operating room.

<Construction of Video Signal Switching Device>

Figure 16:
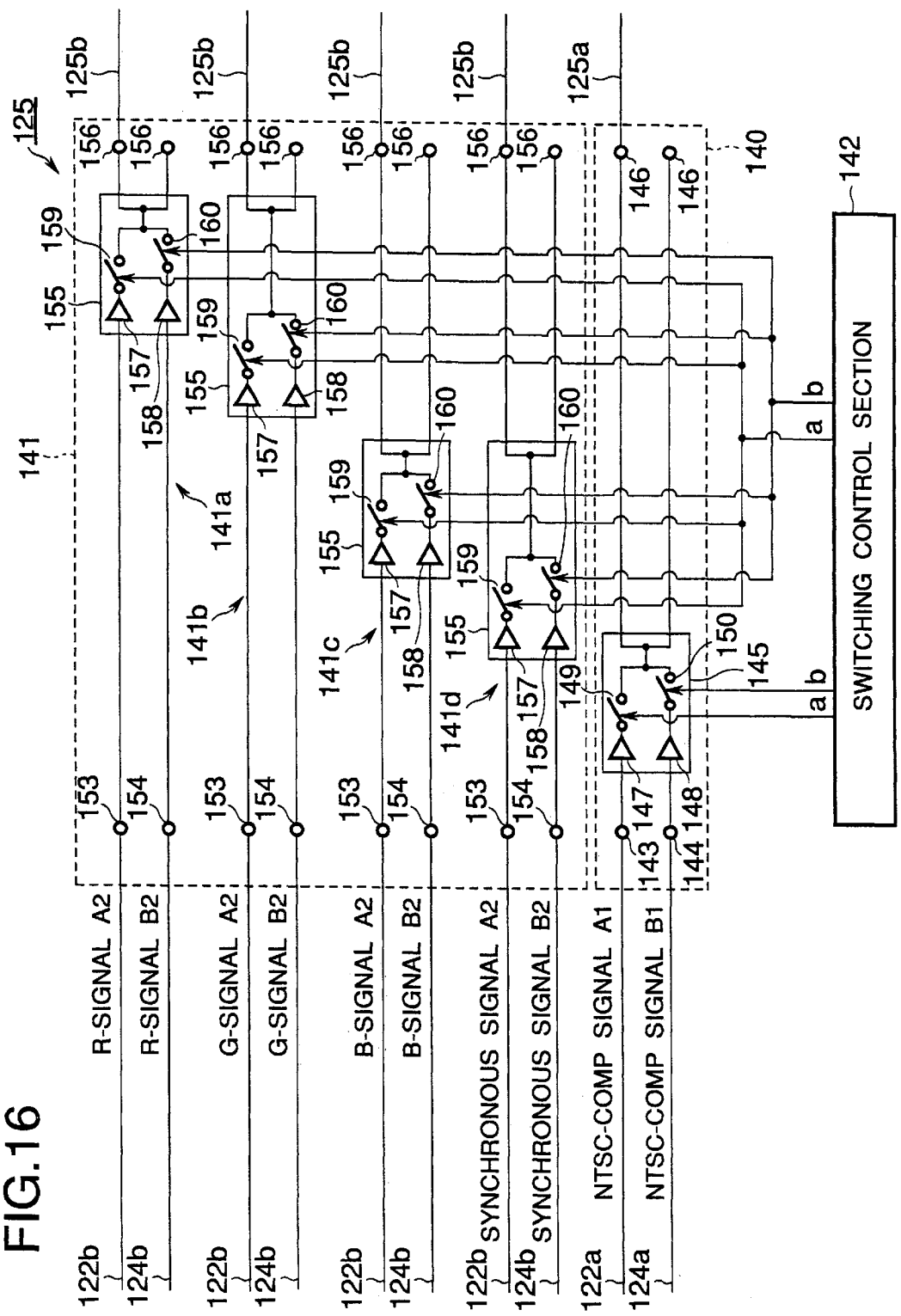
FIG. 16 is a circuit diagram of a main portion of a video signal switching device shown in FIG. 15.

FIG. 16 is a circuit diagram of a main portion of the video signal switching device 125 shown in FIG. 15. In FIG. 16, the video signal switching device 125 is constructed by an NTSC composite signal switching section 140 for switching over between NTSC composite signals of two systems, an RGB component signal switching section 141 for switching over between RGB component signals of two systems, and a switching control section 142 for controlling operations of the respective signal switching sections 140, 141.

The NTSC composite signal switching section 140 has input terminals 143, 144, a connecting switching circuit 145 connected to the input terminals 143, 144 through signal lines, and output terminals 146, 146 each connected to the connecting switching circuit 145. The input terminal 143 is connected to the signal line 122a shown in FIG. 15. An NTSC composite signal of the first system (called a "video signal A1") outputted from the processor device 122 is inputted through this input terminal 143. On the other hand, the input terminal 144 is connected to the signal line 124a. An NTSC composite signal of the second system (called a "video signal B1") outputted from the processor device 124 is inputted to this input terminal 144.

The connecting switching circuit 145 has the same construction as the connecting switching circuit 16 in the first embodiment. More specifically, the connecting switching circuit 145 comprises buffer amplifiers 147, 148 each having functions of both an amplifier and a buffer, and video change-over switches 149, 150. An input terminal of the buffer amplifier 147 is connected to the input terminal 143 and an output terminal of the buffer amplifier 147 is connected to the video change-over switch 149. Similarly, an input terminal of the buffer amplifier 148 is connected to the input terminal 144 and an output terminal of the buffer amplifier 148 is connected to the video change-over switch 150. Output terminals of the video change-over switches 149, 150 are respectively connected to both the output terminals 146, 146 through signal lines. The video change-over switch 149 comprises a relay or a FET. A switching signal a is applied from the switching control section 142 (see FIG. 17) to a control terminal of the video change-over switch 149 (a gate in the case of the FET). Similarly, the video change-over switch 150 also comprises a relay or a FET. A switching signal b is applied from the switching control section 142 to a control terminal of this video change-over switch 150. Each of the switching signals a, b has high or low potential level. The video change-over switches 149, 150 are respectively closed when the switching signals a, b have high potential. The video change-over switches 149, 150 are respectively opened when the switching signals a, b have low potential.

The switching signals a, b are respectively applied to the video change-over switches 149, 150 such that, when one of the switching signals a, b has high potential, the other has a low potential. Therefore, each of the respective video change-over switches 149, 150 is closed when the switching signal a, b applied thereto has high potential. Each of the respective video change-over switches 149, 150 is opened when the switching signal a, b applied thereto has low potential. Therefore, when one of the video change-over switches 149, 150 is closed, the other is opened. Accordingly, the connecting switching device 145 outputs one of the NTSC composite signal A1 of the first system and the NTSC composite signal B1 of the second system to each of the output terminals 146, 146 in accordance with potential levels of the switching signals a, b.

One of the output terminals 146 is connected to the TV monitor 127 through the signal line 125a shown in FIG. 15 and applies the NTSC composite signal outputted from the connecting switching device 145 to the TV monitor 127. Thus, the TV monitor 127 displays a moving image of a photographed object based on the NTSC composite signal and this moving image is recorded to a video tape by the video recorder (VTR) 129. The other output terminal 146 is not used in this sixth embodiment, but may be used to connect onother TV monitor or another video recorder through signal lines.

The RGB component signal switching section 141 is constructed by four signal switching sections 141a to 141d.

Each of the signal switching sections 141a to 141d approximately has the same construction as the above NTSC composite signal switching section 140. Accordingly, only the differences between the signal switching sections 141a to 141d and the NTSC composite signal switching section 140 will next be explained.

The signal line 122b shown in FIG. 15 is connected to each of input terminals 153 of the respective signal switching sections 141a to 141d. An R-signal, a G-signal, a B-signal and a synchronous signal (consisting the RGB component signal of the first system, hereinafter, called a "video signal A2") outputted from a processor device 122 are inputted to these input terminals 153. On the other hand, the signal line 124b shown in FIG. 15 is connected to each of input terminals 154 of the respective signal switching sections 141a to 141d. An R-signal, a G-signal, a B-signal and a synchronous signal (consisting the RGB component signal of the second system, hereinafter, called a "video signal B2") outputted from a processor device 124 are inputted to these input terminals 154.

The connecting switching circuit 155 of each of the signal switching sections 141a to 141d have video change-over switches 159, 160. Similar to the connecting switching section 145, switching signals a, b are applied by the switching control section 142 to control terminals of the video change-over switches 159, 160. Each of the switching signals a, b has high or low potential level. The video change-over switches 159, 160 are respectively closed when the switching signals a, b have high potential. The video change-over switches 159, 160 are respectively opened when the switching signals a, b have low potential. The potential level of the respective switching signals a, b are approximately simultaneously switched over. Further, the connecting switching circuits 155 of all the signal switching sections 141a to 141d approximately simultaneously perform the same operation. Thus, each connecting switching circuit 155 outputs any one of the video signals A2 and B2 at the same time.

One of the output terminals 156, 156 of each of the signal switching sections 141a to 141d is connected to the RGB monitor 126 through the signal line 125b shown in FIG. 15 and applies the RGB component signal outputted from each connecting switching circuit 155 to the RGB monitor 126. The moving image of a photographed object is displayed on the RGB monitor 126 on the basis of these RGB signals. The other of the output terminals 156, 156 is not used in this embodiment, but may be used to connect another output devices such as RGB monitor, another video device, etc. through signal lines.

Figure 17:
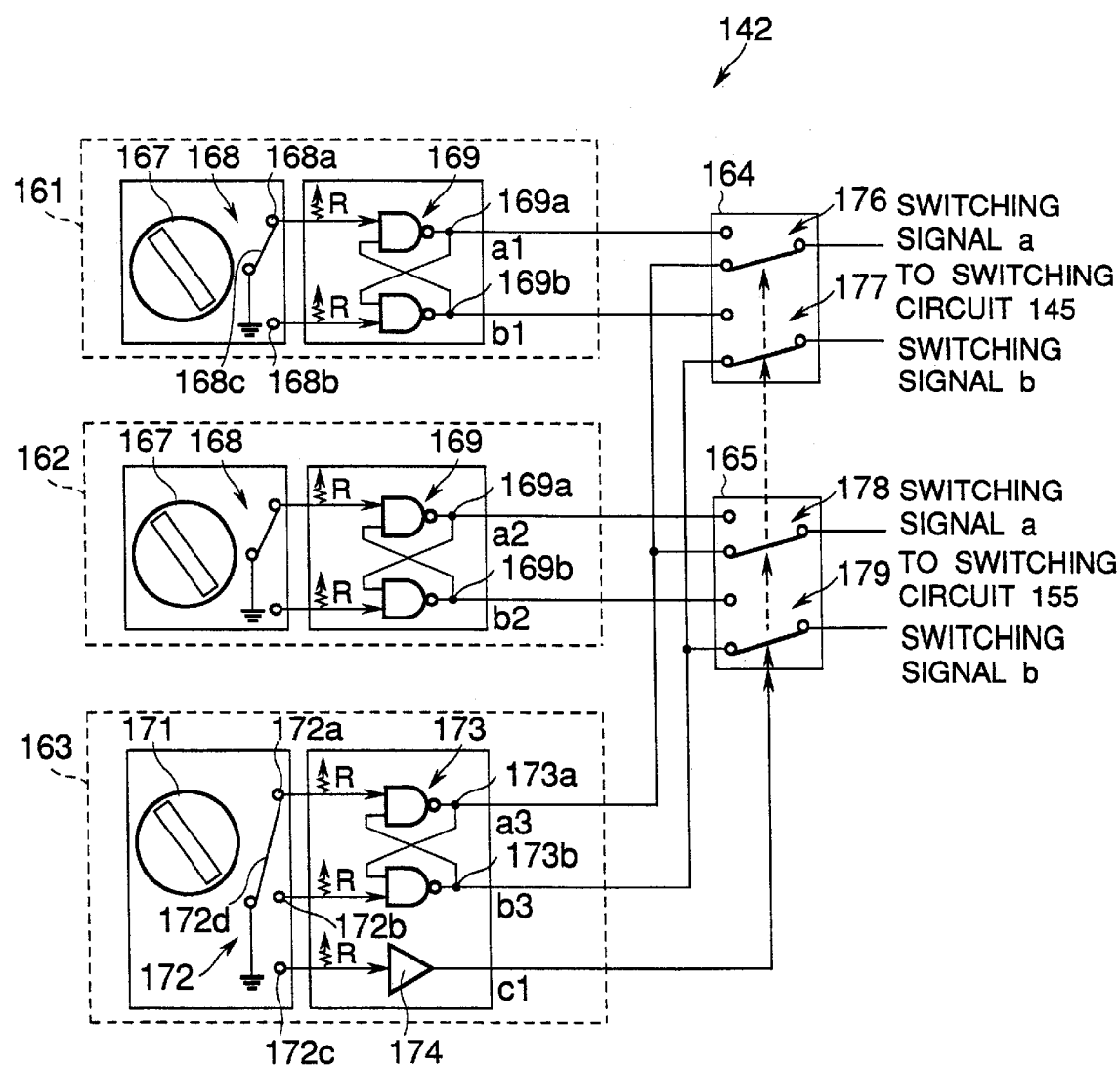
FIG. 17 is a circuit diagram of a switching control section shown in FIG. 16.

The switching control section 142 applies the switching signals a, b according to condition of the video signal switching device 125 set by an operator to each of the connecting switching circuits 145, 155 of the NTSC composite signal switching section 140 and the RGB composite signal switching section 141. FIG. 17 is a circuit diagram of the switching control section 142 shown in FIG. 16. As shown in FIG. 17, the switching control section 142 has switching circuit control sections 161, 162, an synchronous/arbitrariness control section 163 and change-over switches 164, 165.

Here, the switching circuit control section 161 controls an operation of the connecting switching circuit 145 shown in FIG. 16. The switching circuit control section 162 controls an operation of each connecting switching circuit 155 shown in FIG. 16. These switching circuit control sections 161, 162 have the same construction. Accordingly, the switching circuit control section 161 will next be mainly explained in the following description.

The switching circuit control section 161 has a switching dial 167, a manual change-over switch 168 for performing a switching operation according to rotational position of the switching dial 167, and a flip flop 169 connected to each of contacts 168a, 168b of the manual change-over switch 168.

Rotational range of the switching dial 167 is divided into a first range in which the NTSC composite signal (video signal A1) inputted through the input terminal 143 shown in FIG. 16 is selected, and a second range in which the NTSC composite signal (video signal B1) inputted through the input terminal 144 shown in FIG. 16 is selected. The rotational position of the switching dial 167 is set within the first or second ranges by an operator of the video signal switching device 125.

The manual change-over switch 168 has a switching brush 168c connected to the ground and able to selectively come in contact with the contacts 168a and 168b. This switching brush 168c is switched to come in contact with the contact 168a when tha rotational position of the switching dial 167 is set to the above first range. The switching brush 168c is switched to come in contact with the contact 168b when the rotational position of the switching dial 167 is set to the second range.

One input terminal of the flip flop 169 is connected to the contact 168a and pulled up through a resistor R. The other input terminal of the flip flop 169 is connected to the contact 168b and pulled up through a resistor R. On the other hand, each of output terminals 169a, 169b of the flip flop 169 is connected to the above change-over switch 164. Similary, each of the output terminals 169a, 169b of the flip flop 169 of the switching circuit control section 162 is connected to the above change-over switch 165.

The output terminal 169a of the flip flop 169 of the switching circuit control section 161 outputs a signal (called a "switching signal a1") for selecting the video signal Al at an arbitrariness mode, and the output terminal 169b outputs a signal (called a "switching signal b1") for selecting the video signal B1 at the arbitrariness mode. On the other hand, the output terminal 169a of the flip flop 169 of the switching circuit control section 162 outputs a signal (called a "switching signal a2") for selecting the video signal A2 at a arbitrariness mode and the output terminal 169b outputs a signal (called a "switching signal b2") for selecting the video signal B2 at the arbiterariness mode.

Potential levels of the respective switching signals a1, b1, a2, b2 are changed in accordance with rotational position of the respective switching dials 167, 167. More spesifically, when rotational position of each of the switching dials 167, 167 is set to the first range, the switching brush 168c comes in contact with the contact 168a, so that the contact 168a is connected to the ground. Therefore, potential level inputted to the flip flop 169 becomes low on a side of the contact 168a and becomes high on a side of the contact 168b. Accordingly, the potential levels of the switching signals a1, a2 become high and the potential levels of the switching signals b1, b2 become low. In contrast to this, when rotational position of each of the switching dials 167, 167 is set to the second range, the switching brush 168c comes in contact with the contact 168b, so that the contact 168b is connected to the ground. Accordingly, the potential levels of the switching signals a1, a2 becomes low and the potential levels of the switching signals b1, b2 becomes high.

The synchronous/arbitrariness control section 163 has a switching dial 171, a manual change-over switch 172 for performing a switching operation according to rotational position of the switching dial 171, a flip flop 173 connected to each of contacts 172a, 172b of the manual change-over switch 172, and a buffer 174 connected to a contact 172c of the manual change-over switch 172.

Rotational range of the switching dial 171 is divided into a first range in which the video signals A1, A2 are synchronously selected, a second range in which the video signals B1, B2 are synchronously selected, and a third range in which the video signals A1, A2, B1, B2 is arbitrarily selected by each of the switching circuit control sections 161, 162. The rotational position of the switching dial 171 is set within the first, second or third ranges by an operator of the video signal switching device 125.

The manual change-over switch 172 has a switching brush 172d connected to the ground and able to be switched over among the terminals 172a through 172c. The switching brush 172d is switched to contact with the contact 172a when the rotational position of the switching dial 171 is set to the above first range. The switching brush 172d is switched to contact with the contact 172b when the rotational position of the switching dial 171 is set to the second range. The switching brush 172d is switched to contact with the contact 172c when the switching dial 171 is set to the above third range.

One input terminal of the flip flop 173 is connected to the contact 172a and pulled up through a resistor R, and another input terminal of the flip flop 173 is connected to the contact 172b and pulled up through a resistor R. On the other hand, output terminals 173a, 173b of the flip flop 173 are respectively connected to the change-over switches 164, 165. The output terminal 173a of the flip flop 173 outputs a signal (called a "selecting signal a3") for selecting the video signals A1, A2 simultaneously, and the output terminal 173b outputs a signal (called a "selecting signal b3") for selecting the video signals B1, B2 simultaneously.

Potential levels of the respective selecting signals a3, b3 are changed in accordance with the rotational position of the switching dial 171. More spesifically, when the switching dial 171 is set to the first range, the switching brush 172d comes in contact with the contact 172a, so that the contact 172a is connected to the ground. Therefore, a potential level inputted to the flip flop 173 becomes low on a side of the contact 172a and becomes high on a side of the contact 172b. Accordingly, the potential level of the selecting signal a3 becomes high and the potential level of the selecting signal b3 becomes low. On the contrary, when the rotational position of the switching dial 171 is set to the second range, the switching brush 172d comes in contact with the contact 172b, so that the contact 172b is connected to the ground. Accordingly, the potential level of the selecting signal a3 becomes low and the potential level of the selecting signal b3 becomes high.

An input terminal of the buffer 174 is connected to the contact 172c and pulled up through a resistor R. An output terminal of the buffer 174 is connected to control terminals of the respective change-over switches 164, 165. A signal (called a "selecting signal c1") for selecting one of synchronous and arbitrariness of the connecting switching circuits 145, 155 is outputted through an output terminal of the buffer 174.

A potential level of the selecting signal c1 is changed in accordance with the rotational position of the switching dial 171. More spesifically, the rotational position of the switching dial 171 is set to the first or second ranges, potential level of the buffer 174 on its input side becomes high because of pulling up through the resistor R. Therefore, the potential level of the selecting signal c1 becomes high. In contrast to this, when the switching dial 171 is set to the third range, the switching brush 172d comes in contact with the contact 172c, so that the contact 172c is connected to the ground. Accordingly, the potential levels of the buffer 174 on its input side becomes low. Therefore, the selecting signal c1 becomes low.

The change-over switch 164 has a switch 176 for selectively electrically connecting a control terminal of the video change-over switch 149 (see FIG. 16) of the connecting switching circuit 145 to the output terminal 169a of the switching circuit control section 161 and the output terminal 173a of the synchronous/arbitrariness control section 163. The change-over switch 164 also has a switch 177 for selectively electrically connecting a control terminal of the video change-over switch 150 of the connecting switching circuit 145 to the output terminal 169b of the switching circuit control section 161 and the output terminal 173b of the synchronous/arbitrariness control section 163.

Each of the switches 176, 177 performs a switching operation according to the selecting signal c1 from the synchronous/arbitrariness control section 163. More specifically, when the potential level of the switching signal c1 is high, switching pieces of the switches 176, 177 are respectively contacted to the output terminals 173a, 173b of the flip flop 173. In contrast to this, when the potential level of the switching signal c1 is low, the switching pieces of the switches 176, 177 are respectively contacted to the output terminals 169a, 169b of the flip flop 169 of the switching circuit control section 161.

Thus, the change-over switch 164 transmits one set of the output signals of the flip flop 169 of the switching circuit control section 161 or the output signals of the flip flop 173 to the connecting switching circuit 145 as the switching signals a, b.

The change-over switch 165 has a switch 178 for selectively electrically connecting a control terminal of the video change-over switch 159 (see FIG. 16) of each connecting switching circuit 155 to the output terminal 169a of the switching circuit control section 162 and the output terminal 173a of the synchronous/arbitrariness control section 163. The change-over switch 165 also has a switch 179 for selectively electrically connecting a control terminal of the video change-over switch 160 of each connecting switching circuit 155 to the output terminal 169b of the switching circuit control section 162 and the output terminal 173b of the synchronous/arbitrariness control section 163.

Similar to the above switches 176, 177, each of the switches 178, 179 performs a switching operation according to the potential level of the switching signal c1 from the synchronous/arbitrariness control section 163. Thus, the change-over switch 165 transmits one set of the output signals of the flip flop 169 of the switching circuit control section 162 or the output signals of the flip flop 173 to each connecting switching circuit 155 as the switching signals a, b.

The following table 5 shows the relation of potential level of each of the switching signals a1 through a3, b1 through b3 and c1 inputted to the respective change-over switches 164, 165 and each of the video signal outputted from the video signal switching device 125.

TABLE 5

| Switching signal c1 | Switching signal a3 | Switching signal b3 | Switching signal a2 | Switching signal b2 | Switching signal a1 | Switching signal b1 | RGE output signal | NTSC output signal |
| --- | --- | --- | --- | --- | --- | --- | --- | --- |
| HIGH | HIGH | LOW  | —    | —    | —    | —    | A2 | A1 |
| HIGH | LOW  | HIGH | —    | —    | —    | —    | B2 | B1 |
| LOW  | HIGH | HIGH | HIGH | LOW  | HIGH | LOW  | A2 | A1 |
| LOW  | HIGH | HIGH | HIGH | LOW  | LOW  | HIGH | A2 | B1 |
| LOW  | HIGH | HIGH | LOW  | HIGH | HIGH | LOW  | B2 | A1 |
| LOW  | HIGH | HIGH | LOW  | HIGH | LOW  | HIGH | B2 | B1 |

As shown in the table 5, when the potential level of the selecting signal c1 is a high potential (when the switching dial 171 is set to the first and second ranges), the change-over switches 164, 165 respectively output the switching signals a3, b3 as the switching signals a, b irrespective of setting of each of the switching dials 167, 167. Thus, the respective switching circuits 145, 155 approximately simultaneously perform the same operation.

More spesifically, when the switching signal a3 has high potential and the switching signal b3 has low potential, the switching signal a of high potential and the switching signal b of low potential are respectively inputted from the change-over switches 164, 165 to the connecting switching circuits 145, 155. Thus, only the respective video change-over switches 149, 159 are closed. Accordingly, a video signal outputted from the video signal switching device 125 is approximately simultaneously switched over to the video signals A1 and A2 belonging to the first system.

When the switching signal a3 has low potential and the switching signal b3 has high potential, the switching signal a of low potential and the switching signal b of high potential are respectively inputted from the change-over switches 164, 165 to the connecting switching circuits 145, 155. Thus, only the respective video change-over switches 150, 160 are closed. Accordingly, the video signal outputted from the video signal switching device 125 is approximately simultaneously switched over to the video signals B and B2 belonging to the second system.

When the switching dial 171 is set to the third range and therefore the potential level of the switching signal c1 becomes low, output signal levels of the switching circuit control sections 161, 162 are respectively individually set by the switching dials 167, 167. The change-over switches 164, 165 respectively output the switching signals a and b according to the potential levels of the switching signals a1, b1, a2, b2 set by the respective setting thumbscrews 167, 167 and inputted to these change-over switches 164, 165. Accordingly, an output signal from the NTSC composite signal switching section 140 and an output signal from the RGB component signal switching section 141 are separately switched over in accordance with the setting of each switching dial 167.

<Operation of Video Signal Switching Device>

An operation of the video signal switching device 125 in the sixth embodiment having the above construction will next be explained. It is assumed that the video signal (NTSC composite signal) A1 is inputted to the input terminal 143 of the video signal switching device 125, that the video signal (NTSC composite signal) B1 is inputted to the input terminal 144, that the video signal (RGB component signal) A2 is inputted to each input terminal 153 and that the video signal (RGB component signal) B2 is inputted to each input terminal 154.

Here, if an operator (e.g., an engineer) of the video signal switching device 125 rotates the switching dial 171 to set its rotational position to the first range, for example, the switching brush 172d comes in contact with the contact 172a, so that the contact 172a is connected to the ground. Thus, the switching signal a3 of high potential and the switching signal b3 of low potential are respectively inputted to the change-over switches 164, 165. The switching signal a of high potential and the switching signal b of low potential are respectively outputted from the change-over switches 164, 165 and are respectively inputted to the connecting switching circuits 145, 155. In each of the connecting switching circuits 145, 155, only each of the video change-over switches 149, 159 is closed. Therefore, a signal transmitting path connecting the input terminal 143 and the output terminals 146 is formed. At the same time, a signal transmitting path connecting the input terminal 153 and the output terminals 156 is formed. Accordingly, the video signal A1 is outputted from the output terminals 146 of the NTSC composite signal switching section 140 and the video signal A2 is outputted from each output terminals 156 of the RGB component signal switching section 141.

Thereafter, if the operator rotates the switching dial 171 to set its rotational position to the second range, the switching brush 172d comes in contact with the contact 172b, so that the contact 172b is connected to the ground. Thus, the switching signal a3 of low potential and the switching signal b3 of high potential are respectively inputted to the change-over switches 164, 165. Further, the switching signal a of low potential and the switching signal b of high potential are respectively outputted from the change-over switches 164, 165. Thus, only the video change-over switches 150, 160 of the respective connecting switching circuits 145, 155 are closed. Accordingly, the video signal B1 is outputted from the NTSC composite signal switching section 140 and the video signal B2 is outputted from the RGB component signal switching section 141.

Thereafter, if the operator rotates the switching dial 171 to set its rotational position to the third range, the contact 172c is connected to the ground, so that the switching signal c1 of low potential is inputted to each of the change-over switches 164, 165. Thus, each of the change-over switches 164, 165 outputs the switching signals a and b according to potential levels of the switching signals a1, b1, a2, b2 from the respective switching circuit control sections 161, 162. For example, if the operator rotates the switching dial 167 of the switching circuit control section 161 to set its rotational position to the first range and also rotates the setting dial 167 of the switching circuit control section 162 to set its rotational position to the second range, the switching signal a of high potential is outputted from the change-over switch 164 and the switching signal b of high potential is outputted from the change-over switch 165. Accordingly, the video signal A1 is outputted from the NTSC composite signal switching section 140 and the video signal B2 is outputted from the RGB component signal switching section 141.

<Operation in Sixth Embodiment>

An operation of the endoscope system in the sixth embodiment explained above will next be explained. When a photographed object(e.g., a living body organization within an organic body) is photographed by each of the video endoscopes 121, 123, an NTSC composite signal (the video signal A1) and an RGB component signal (the video signal A2) respectively showing an image of the object photographed by the video endoscope 121 are outputted from the processor device 122, and another NTSC composite signal (the video signal B1) and another RGB component signal (the video signal B2) respectively showing the image of the object photographed by the video endoscope 123 are outputted from the processor device 124. The video signals A1, B1 are respectively inputted to the video signal switching device 125 through the signal lines 122a, 124a. The video signals A2, B2 are respectively inputted to the video signal switching device 125 through the signal lines 122b, 124b.

At this time, an operator (the engineer) of the video signal switching device 125 conforms an output signals of the video signal switching device 125 to a system used at present. For example, when the first system (the video endoscope 121) is used, the operator sets the rotational position of the switching dial 171 of the video signal switching device 125 to the first range. Accordingly, the video signal A1 is outputted from the output terminal 146 of the video signal switching device 125 and the video signal A2 is outputted through the output terminals 156.

Thus, the video signal A2 is inputted to the RGB monitor 126 through the signal line 125b and a picture image based on the video signal A2 is displayed on the RGB monitor 126. In contrast to this, the video signal A1 is inputted to the monitor 127 through the signal line 125a and a picture image based on the video signal A1 is displayed on the monitor 127 and is recorded to the video recorder 129.

Thereafter, when the video endoscope in use is changed from the video endoscope 121 to the video endoscope 123, the engineer sets the rotational position of the switching dial 171 of the video signal switching device 125 to the second range. Thus, the video signal outputted from the video signal switching device 125 is changed to the video signals B1 and B2. Accordingly, displayed contents on the monitors 126, 127 are switched over to picture images based on the video signals B1, B2 and the picture image based on the video signal B1 is also recorded to the video recorder 129.

Thus, plural kinds of video signals can be switched over and outputted by the video signal switching device 125 in the sixth embodiment. Accordingly, it is sufficient to prepare one video signal switching device 125 so as to switch over the RGB component signals and the NTSC composite signals outputted from the respective processor devices 122, 124. Therefore, the number of components of the endoscope system can be reduced and a free space within the operating room can be secured and wiring in the endoscope system can be simplified.

Further, in accordance with the video signal switching device 125 in sixth embodiment, the systems of the video signals can be changed only by operation of the switching dial 171, so that a load of the operator in operating the video signal switching device 125 can be reduced. Further, the operator can freely select a combination of output signals from the video signal switching device 125 by operating each switching dials 167, 167, 171. Therefore, a degree of setting freedom of the video signal switching device 125 is high.

Figure 18:
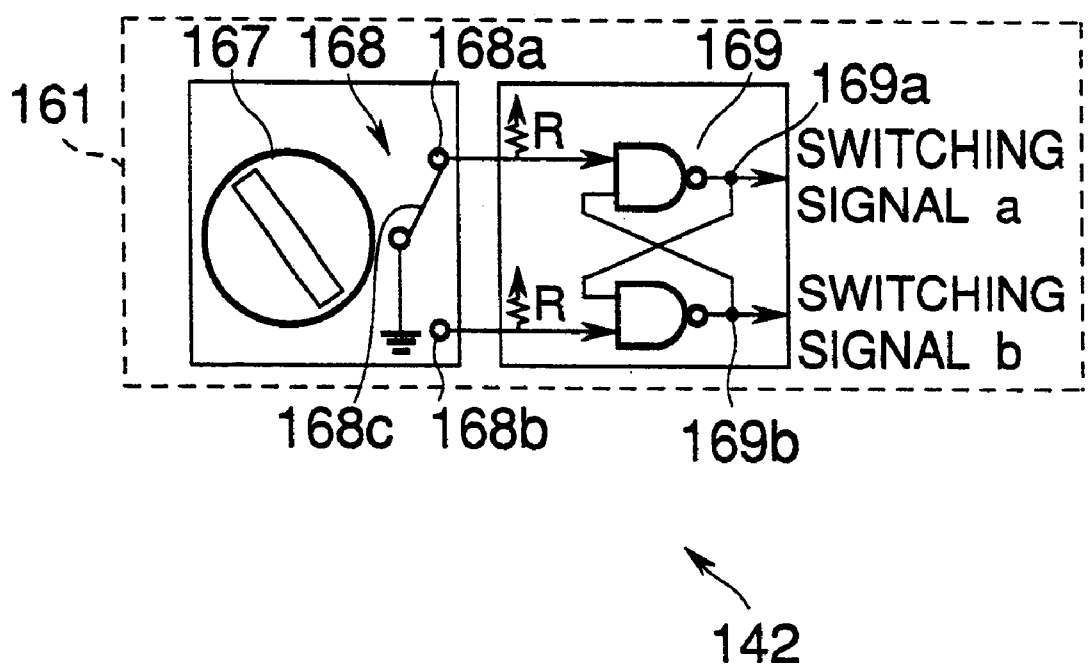
FIG. 18 is a circuit diagram showing another construction of the switching control section shown in FIG. 16.

The switching control circuit 142 of the video signal switching device 125 in the sixth embodiment may be constructed as shown in FIG. 18. FIG. 18 shows the switching control circuit 142 constructed such that only one of the video signals (the video signals A1, A2) of the first system and the video signals (the video signals B1, B2) of the second system can be selected as an output signal of the video signal switching device 125.

In this case, different from FIG. 16, an output terminal 169a of a flip flop 169 is connected to each of video change-over switches 149, 159 and an output terminal 169b of the flip flop 169 is connected to each of video change-over switches 150, 160. The following table 6 shows the relation of switching signals a, b outputted through the respective output terminals 169a, 169b of the flip flop 169 shown in FIG. 18 and an output signal of the video signal switching device 125.

TABLE 6

| Switching signal a | Switching signal b | NTSC composite signal | RGB component signal |
|---|---|---|---|
| High | Low | Video signal A1 | Video signal A2 |
| Low | High | Video signal B1 | Video signal B2 |

When the switching control circuit 142 shown in FIG. 18 is adopted, it is impossible to individually select an output signal of the NTSC composite signal switching section 140 and an output signal of the RGB component signal switching section 141. However, the switching circuit control section 162, the synchronous/arbitrariness control section 163 and the change-over switches 164, 165 shown in FIG. 17. Therefore, the construction of the video signal switching device 125 can be simplified.

SEVENTH EMBODIMENT

Figure 19:
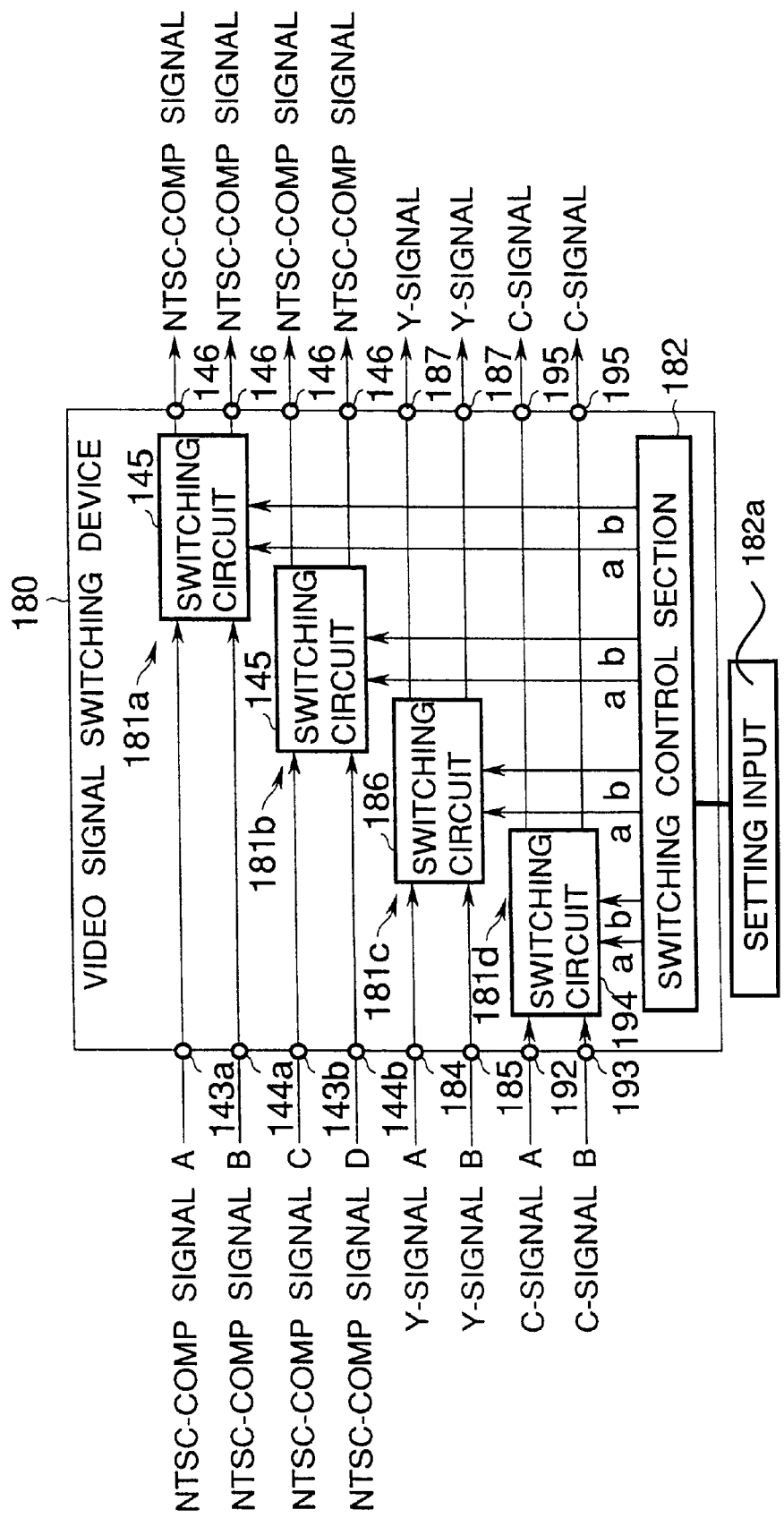
FIG. 19 is a circuit diagram of a main portion of a video signal switching device in a seventh embodiment of the present invention.

FIG. 19 is a block diagram showing a video signal switching device 180 in a seventh embodiment of the present invention. The video signal switching device 180 shown in FIG. 19 can outputs two of four systems of NTSC composite signals inputted from unillustrated plural video processor devices for an endoscope connected to this video signal switching device 180 toward an output device (a monitor or a recorder) connected to this video signal switching device 180. The video signal switching device 180 also outputs one of two systems of Y(luminance signal)/C(color-difference signal, or carrier chrominance signal) signals inputted from unillustrated plural video processor devices for an endoscope connected to this video signal switching device 180 toward an output device connected to this video signal switching device 180.

This video signal switching device 180 has a construction approximately similar to that of the video signal switching device 125 in the sixth embodiment. Accordingly, the difference between these video signal switching devices will next mainly explained.

As shown in FIG. 19, the video signal switching device 180 comprises four signal switching sections 181a through 181d and a switching control section 182. Each of the signal switching sections 181a, 181b corresponds to the NTSC composite signal switching section 140 shown in FIG. 16. More spesifically, the signal switching section 181a selects one of the NTSC composite signal of a first system inputted through an input terminal 143a and the NTSC composite signal of a second system inputted through an input terminal 144a with a connecting switching circuit 145 and outputs the selected signal through output terminals 146, 146. The signal switching section 181b selects one of the NTSC composite signal of a third system inputted through an input terminal 143b and the NTSC composite signal of a fourth system inputted from an input terminal 144b with a switching circuit 145 and outputs this selected signal through output terminals 146, 146.

The signal switching sections 181c, 181d respectively have the same constructions as the signal switching sections 181a, 181b. However, the Y/C signals of two systems are inputted to the signal switching sections 181c, 181d. More spesifically, a Y-signal of a first system is inputted to an input terminal 184 of the signal switching section 181c and a Y-signal of a second system is inputted to an input terminal 185 of the signal switching section 181c.

Figure 20:
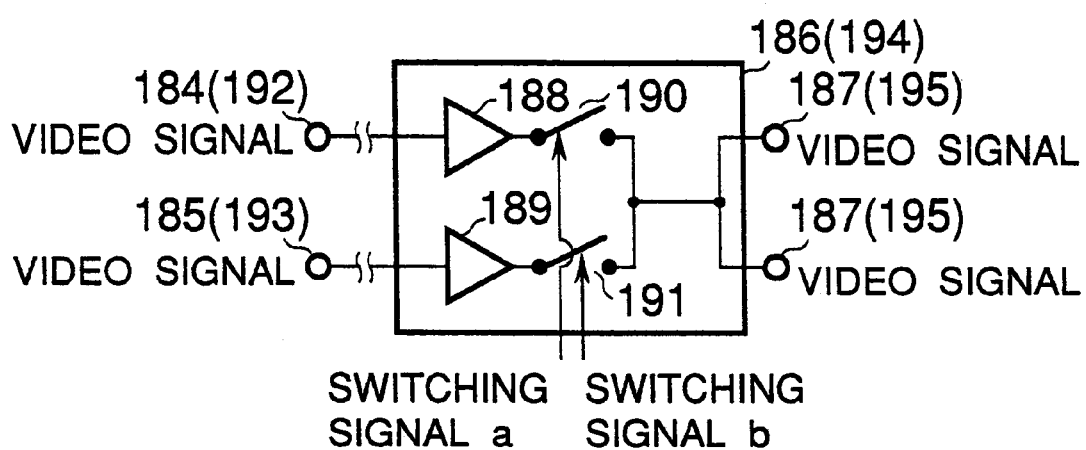
FIG. 20 is a diagram of a connecting switching circuit shown in FIG. 19.

FIG. 20 is a circuit diagram showing the construction of a connecting switching circuit 186 of the signal switching section 181c shown in FIG. 19. As shown in FIG. 20, the connecting switching circuit 186 has buffers 188, 189 connected to the respective input terminals 184, 185 and also has switches 190, 191 connected to output terminals of the respective buffers 188, 189. In short, the connecting switching circuit 186 has the same construction as each of the connecting switching circuit 145 and the connecting switching circuit 155 shown in FIG. 16. The connecting switching circuit 186 outputs a Y-signal inputted through any one of the input terminals 184, 185 to external through output terminals 187, 187 in accordance with switching signals a, b provided from the switching control section 182.

On the other hand, a C-signal of the first system is inputted to an input terminal 192 of the signal switching section 181d and a C-signal of the second system is inputted to an input terminal 193 of the signal switching section 181d. A connecting switching circuit 194 of the signal switching section 181d has the same construction as the connecting switching circuit 186. The connecting switching circuit 194 outputs a C-signal inputted through any one of the input terminals 192, 193 to external through output terminals 195, 195 in accordance with the switching signals a, b.

The switching control section 182 comprises a control section for controlling an operation of the signal switching section 181a, a control section for controlling an operation of the signal switching section 181b, and a control section for controlling each of operations of the signal switching sections 181c, 181d. The control sections for respectively controlling the operations of the signal switching sections 181a, 181b have the constructions shown in FIG. 18 and output the switching signals a, b according to the table 6 to the respective connecting switching circuits 145. The control sections for controlling the operations of the respective signal switching sections 181c, 181d also have the constructions shown in FIG. 18 and approximately simultaneously output the switching signals a, b according to the table 6 to the respective connecting switching circuits 186, 194. Thus, the connecting switching circuits 186 and 194 approximately simultaneously perform switching according to rotational position of the switching dial 167 (see FIG. 18).

In the video signal switching device 180 in the seventh embodiment, one of the NTSC composite signal of the first system and the NTSC composite signal of the second system is selected by and outputted from the signal switching section 181a in accordance with setting of the switching control section 182. One of the NTSC composite signal of the third system and the NTSC composite signal of the fourth system is also selected by and outputted from the signal switching section 181b. Further, one of the Y/C signal of the first system and the Y/C signal of the second system is selected by and outputted from each of the signal switching sections 181c, 181d.

Figure 21:
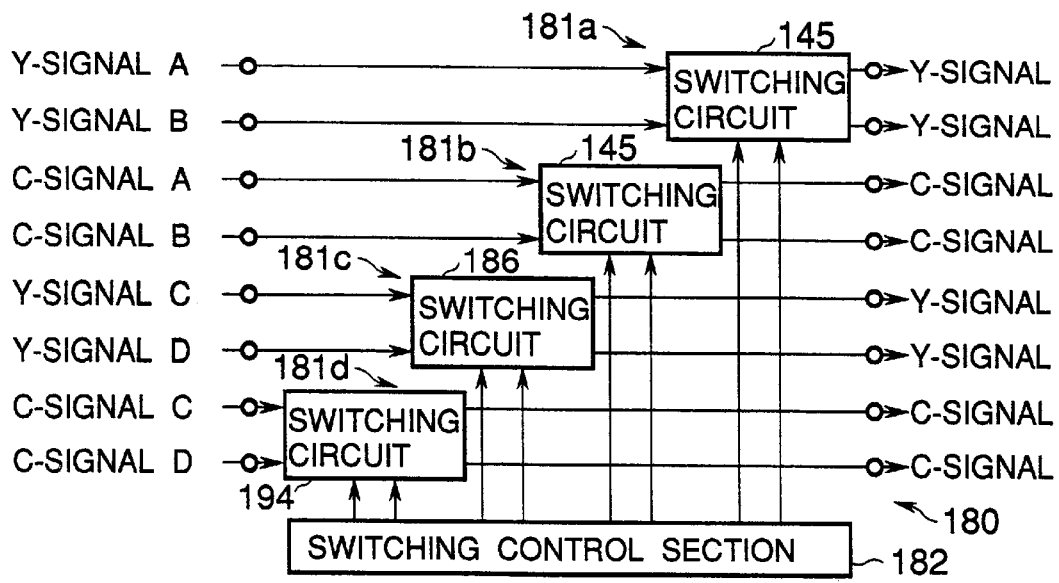
FIG. 21 is a circuit diagram showing a main portion of a modification example of the video signal switching device shown in FIG. 19.
Figure 22:
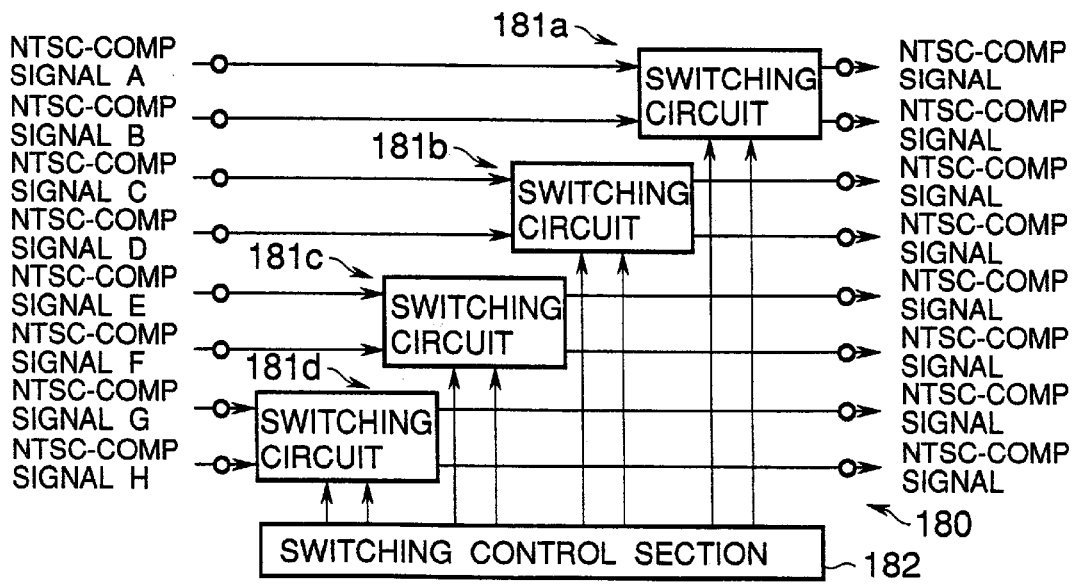
FIG. 22 is a circuit diagram showing a main portion of a modification example of the video signal switching device shown in FIG. 19.

The video signal switching device 180 in the seventh embodiment has effects approximately similar to those of the video signal switching device 125 in the sixth embodiment. The video signal switching device 180 may be used to switch over four systems of the Y/C signals (see FIG. 21), to switch over eight systems of the NTSC composite signals (see FIG. 22) and to switch two systems of the RGB component signals (see FIG. 23). In these cases, the switching control section may control the signal switching sections 181a through 181d according to the input patterns of video signals, as shown in FIG. 24, e.g., via a setting input 182a (shown in FIG. 19) which may include a multi-value switch, or include (or be connected to) a detector responsive to the type of input signal pattern. For example, when a setting links two or more sets of signal inputs according to the systems, patterns, or settings as above, the switching control section 182 controls the signal switching sections 181a through 181d to switch the linked signal inputs in tandem.

EIGHTH EMBODIMENT

Figure 25:
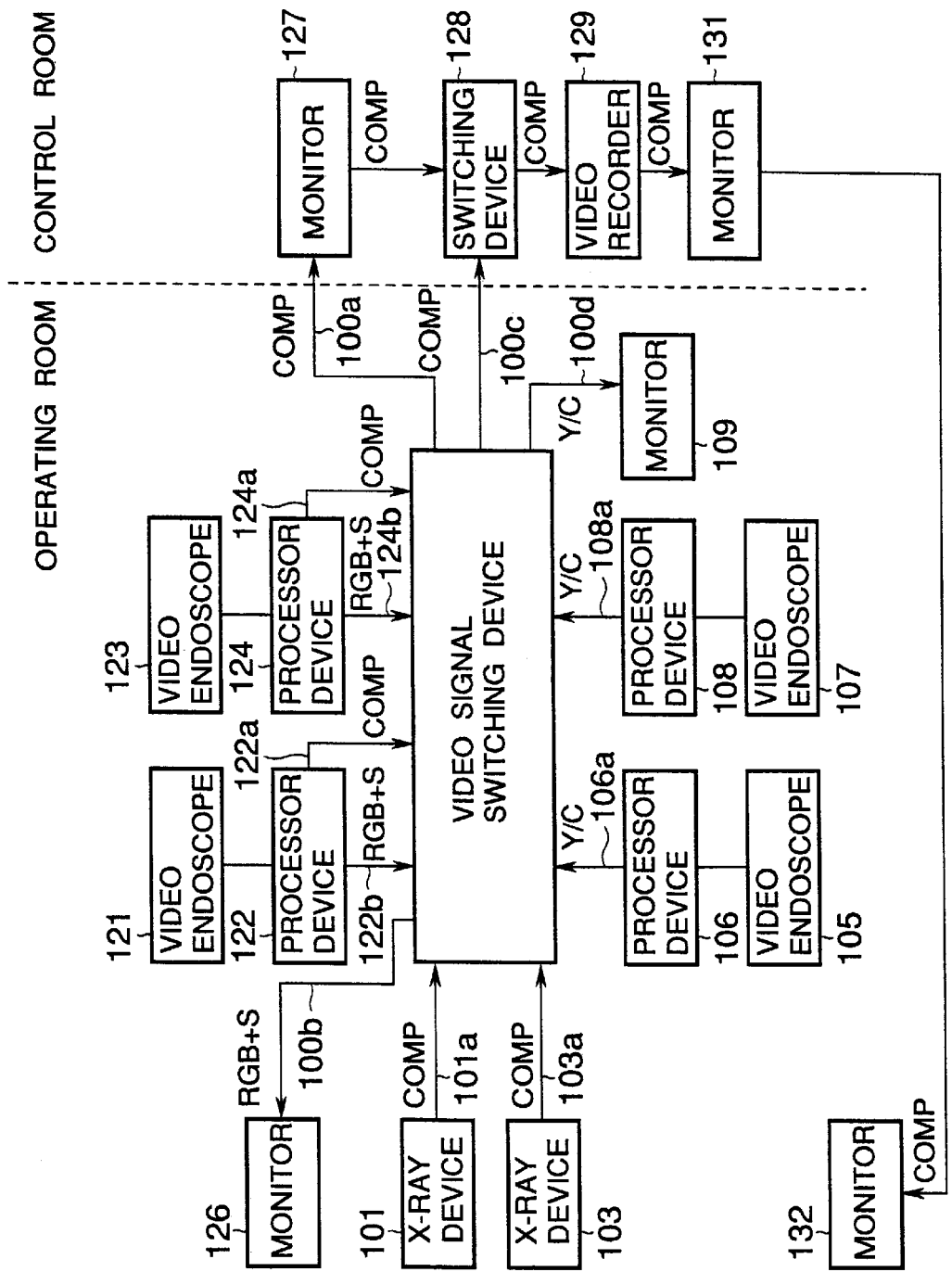
FIG. 25 is a schematic view of an endoscope system in an eighth embodiment of the present invention.

FIG. 25 is a schematic view showing an endoscope system in an eighth embodiment of the present invention. This endoscope system includes a construction common to the endoscope system shown in FIG. 15. Accordingly, a construction different from that of the endoscope system shown in FIG. 15 will next be mainly explained. In FIG. 20, the same components as in FIG. 15 are designated by the same reference numerals.

As shown in FIG. 25, X-ray devices 101 and 103 are respectively connected to the video signal switching device 100 through signal sines 101a, 103a. Two systems of NTSC composite signals are inputted from the respective X-ray devices 101, 103 to the video signal switching device 100. The X-ray devices 101, 103 have the same construction as the X-ray device 130 shown in FIG. 15. A processor device 106 connected to a video endoscope 105 is also connected to the video signal switching device 100 through a signal line 106a. Further, a processor device 108 connected to a video endoscope 107 is connected to the video signal switching device 100 through a signal line 108a. Thus, two systems of Y/C signals are inputted to the video signal switching device 100.

The video signal switching device 100 is connected to a monitor 127 through a signal line 100a for transmitting an NTSC composite signal outputted from the processor device 122 or 124. The video signal switching device 100 is also connected to an RGB monitor 126 through a signal line 100b for transmitting RGB component signals outputted from the processor device 122 or 124. The video signal switching device 100 is also connected to a switching device 128 through a signal line 100c for transmitting the NTSC composite signal outputted from the X-ray device 101 or 103. Further, the video signal switching device 100 is connected to a Y/C monitor 109 through a signal line 100d for transmitting the Y/C signal outputted from the processor device 106 or 108.

Figure 26:
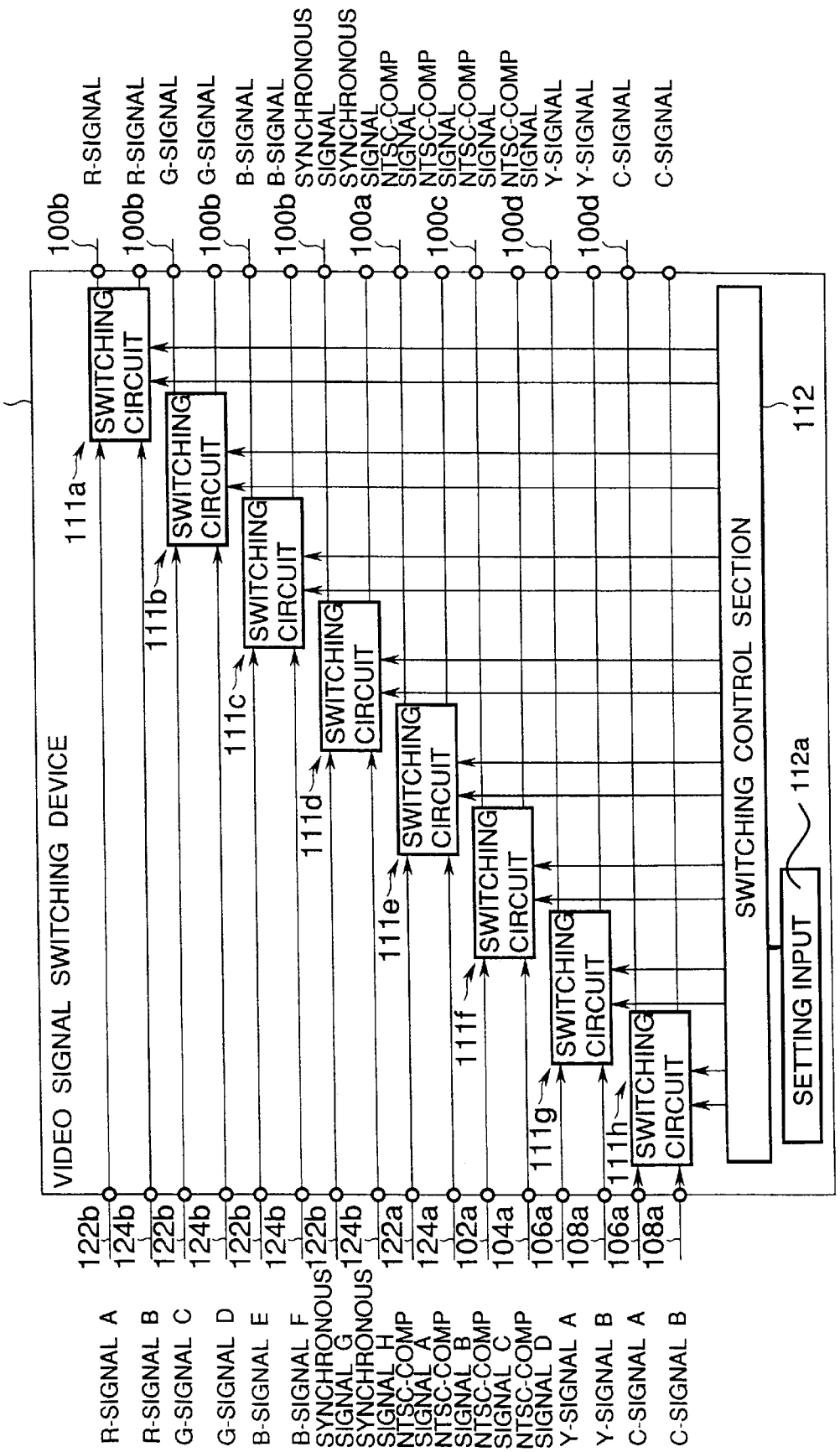
FIG. 26 is a circuit diagram of a main portion of a video signal switching device shown in FIG. 25.

FIG. 26 is a block diagram of the video signal switching device 100 shown in FIG. 25. In FIG. 26, the video signal switching device 100 comprises eight signal switching sections 111a through 111h and a switching control section 112 for controlling operations of these signal switching sections 111a through 111h. Each of the signal switching sections 111*a* through 111*h* has the same construction as the NTSC signal switching section 140 shown in FIG. 16.

The signal switching sections 111*a* through 111*d* supply an RGB component signals inputted from any one of the processor devices 122, 124 to the RGB monitor 126. The signal switching section 111*e* supplies an NTSC composite signal inputted from one of the processor devices 122, 124 to the TV monitor 127. The signal switching section 111*f* supplies an NTSC composite signal inputted from any one of the X-ray devices 101, 103 to the switching device 128. Further, the signal switching sections 111*g*, 111*h* supply a Y/C signal inputted from any one of the processor devices 106, 108 to the Y/C monitor 109.

Each of the signal switching sections 111*a* through 111*h* performs an operation according to switching signal provided from the switching control section 112. The switching control section 112 outputs the switching signals to each of the signal switching sections 111*a* through 111*h* according to the setting by an operator. This switching control section 112 has a construction shown in FIG. 17, a construction shown in FIG. 18, or a combination of these constructions. However, the switching control section 112 must be constructed such that the signal switching sections 111*a* through 111*d* approximately simultaneously perform the same switching and the signal switching sections 111*g*, 111*h* approximately simultaneously perform the same switching.

The video signal switching device in the eighth embodiment has effects similar to those of the video signal switching device 125 in the sixth embodiment. Further, whether the inputted video signals of two systems is the RGB component signals, the NTSC composite signal, or the Y/C signal, the video signal switching device can output the video signal to a monitor (monitors 126, 127, 109) and a video device 129 set by an operator.

As shown in FIG. 27, the video signal switching device 100 can cope with various combinations of signals inputted thereto, e.g., via a setting input 112*a* (shown in FIG. 26) which may include a multi-value switch, or include (or be connected to) a detector responsive to the type of input signal pattern. The switching control section 112 may control the signal switching sections 111*a* through 111*h* in accordance with the input patterns of the respective video signals. For example, when a setting links two or more sets of signal inputs according to the systems, patterns, or settings as above, the switching control section 112 controls the signal switching sections 111*a* through 111*h* to switch the linked signal inputs in tandem.

NINTH EMBODIMENT

The video signal switching device in each of the first through eighth embodiments selects on of inputted video signals and outputs this selected signal, so that formats of the inputted video signals (an NTSC composite signal, a Y/C separating signal, RGB component signals, etc.) and those of the outputted video signal are the same as each other. Accordingly, if only an output device (a monitor device, a video recorder, etc.) which can treat only a specific format of video signal is arranged, it is necessary to conform the format of the video signal outputted from the video processor device for an endoscope to the format that the output device can treat. Further, when the number of formats of video signals able to be outputted from the video processor device is limited to only one, an output device capable of treating this format of the video signal must be prepared. In short, a format of the video signal outputted from the video processor must be conformed to a format of the video signal able to be processed by the output device. In consideration of the above problems in the first through eighth embodiments, a video signal switching device in the ninth embodiment of the present invention is constructed such that a picture image photographed by the endoscope can be displayed on or recorded to the output device even when no output device corresponds to the format of a video signal outputted from the video processor device for an endoscope.

<Construction of Endoscope System>

FIG. 28 is a schematic view showing the endoscope system in the ninth embodiment of the present invention. As shown in FIG. 28, the endoscope system comprises a video signal switching device 200, plural video processor devices for an endoscope (hereinafter, simply called "processor devices") 212, 214, 218, 220, 224, 226 and plural output devices (monitors or video devices) 215, 216, 221, 222, 227, 228, 229 connected to this video signal switching device 200. More specificaly, a processor device 212 connected to a video endoscope 211 is connected to the video signal switching device 200 through a signal line 212*a*. A processor device 214 connected to a video endoscope 213 is also connected to the video signal switching device 200 through a signal line 214*a*. These processor devices 212, 214 respectively input RGB component signals (with a synchronous signal) showing picture images of an object photographed by the video endoscopes 211, 213 to the video signal switching device 200 through the signal lines 212*a*, 214*a*.

A processor device 218 connected to a video endoscope 217 is also connected to the video signal switching device 200 through a signal line 218*a*. A processor device 220 connected to a video endoscope 219 is also connected to the video signal switching device 200 through a signal line 220*a*. These processor devices 219, 220 respectively input Y(luminance signal)/C(color-difference signal or carrier chrominance signal) signals showing the picture images of the object photographed by the video endoscopes 217, 219 to the video signal switching device 200 through the signal lines 218*a*, 220*a*.

Further, a processor device 224 connected to a video endoscope 223 is connected to the video signal switching device 200 through a signal line 224*a*. A processor device 226 connected to a video endoscope 225 is connected to the video signal switching device 200 through a signal line 226*a*. These processor devices 224, 226 respectively input NTSC composite signals (composite video signals) showing picture images of the object photographed by the video endoscopes 223, 225 to the video signal switching device 200 through the signal lines 224*a*, 226*a*.

Monitors 215, 222 are connected to the video signal switching device 200 through signal lines 210*a*, 210*d* for transmitting the RGB component signals. A TV monitor 216 and video recorders 227, 228 are also connected to the video signal switching device 200 through signal lines 210*b*, 210*e*, 210*f* for transmitting the NTSC composite signals. Further, monitors 221, 229 are connected to the video signal switching device 200 through signal lines 210*c*, 210*g* for transmitting the Y/C signals. The monitors 215, 222 can display only moving images based on the RGB component signals. The TV monitor 216 can display only moving images based on the NTSC composite signals and the video recorders 227, 228 can record only the NTSC composite signals.

<Construction of Video Signal Switching Device>

Figure 29:
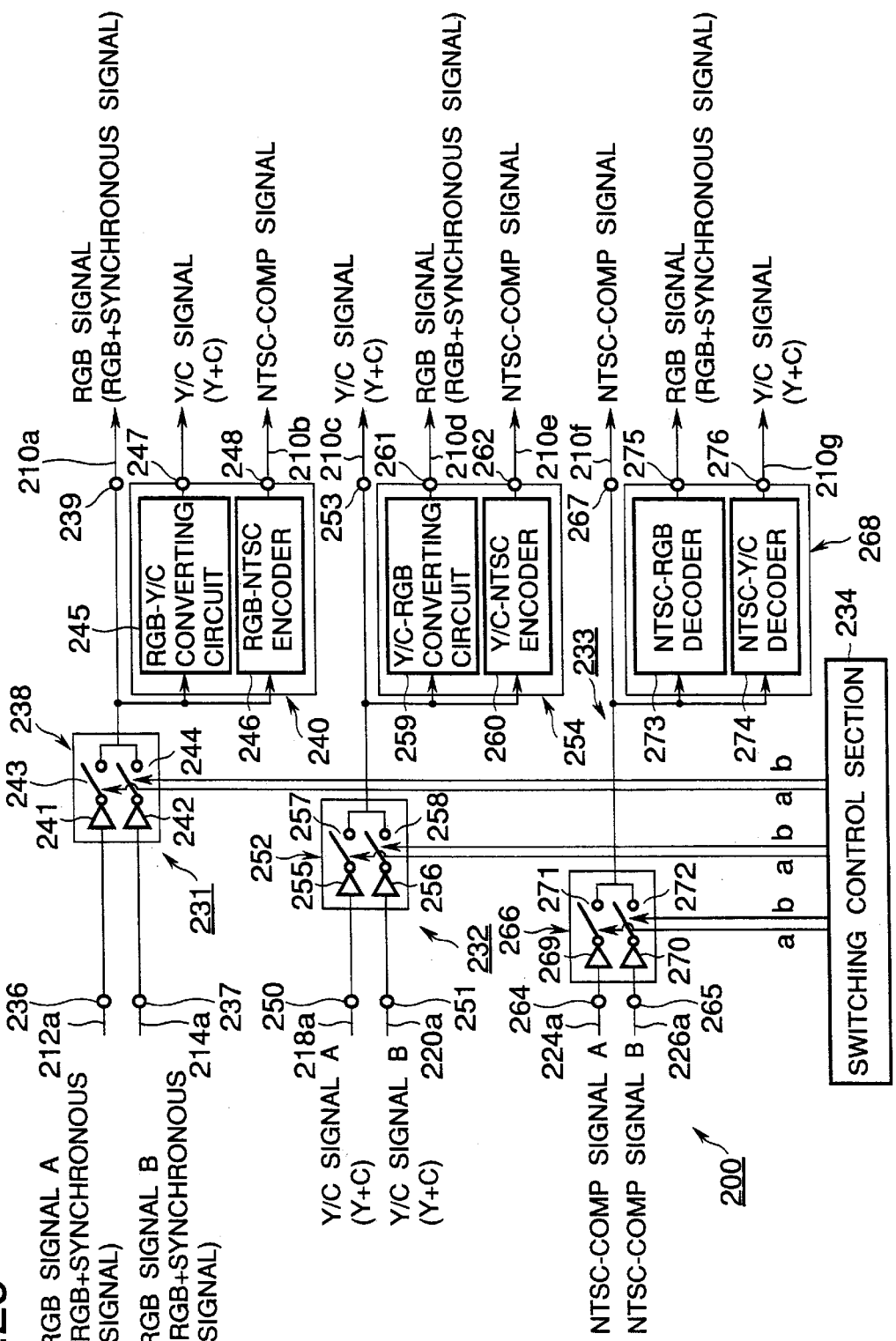
FIG. 29 is a circuit diagram of a main portion of a video signal switching device shown in FIG. 28.

FIG. 29 is a circuit diagram showing the construction of the video signal switching device 200 shown in FIG. 28. As shown in FIG. 29, the video signal switching device 200 comprises an RGB component signal processing section 231, a Y/C signal processing section 232, an NTSC composite signal processing section 233 and a switching control section 234.

The RGB component signal processing section 231 comprises input terminals 236, 237, a connecting switching circuit 238 connected to each of these input terminals 236, 237 through a signal line, and an output terminal 239 and a signal converting section 224 respectively connected to this connecting switching circuit 238.

The input terminal 236 is connected to the processor device 212 through the signal line 212a shown in FIG. 28. The RGB composite signal (called an "RGB signal A") showing a moving image of the object photographed by the video endoscope 211 are inputted to this input terminal 236. On the other hand, the input terminal 237 is connected to the processor device 214 through the signal line 214a. The RGB ocmponent signal (called an "RGB signal B") showing a moving image of the object photographed by the video endoscope 213 are inputted to this input terminal 237.

The connecting switching circuit 238 has the same construction as the connecting switching circuit 16 in the first embodiment. More specifically, the connecting switching circuit 238 is constructed of buffer amplifiers 241, 242 each having functions of an amplifier and a buffer, and video change-over switches 243, 244. An input terminal of the buffer amplifier 241 is connected to the above input terminal 236, and an output terminal of the buffer amplifier 241 is connected to one end of the video change-over switch 243. Similarly, an input terminal of the buffer amplifier 242 is connected to the above input terminal 237 and an output terminal of the buffer amplifier 242 is connected to one end of the video change-over switch 244. The other end of each of the video change-over switches 243, 244 is connected to the above output terminal 239 and the signal converting section 240. The video change-over switch 243 comprises a relay or a FET. A switching signal a outputted from the switching control section 234 is applied to a control terminal (that is, a gate in the case of the FET) of this video change-over switch 243. Similarly, the video change-over switch 244 also comprises a relay or a FET. A switching signal b outputted from the switching control section 234 is applied to a control terminal of this video change-over switch 244.

Each of the video change-over switches 243, 244 is closed when the switching signal inputted thereto has high potential and opened when the switching signal inputted thereto has low potential. When one of these switching signals a, b has high potential, the other has low potential. Therefore, when one of the video change-over switches 243, 244 is closed, the other is opened. Accordingly, the connecting switching circuit 238 selects one of the RGB component signals A and B inputted to this connecting switching circuits 238 in accordance with the switching signals a, b applied by the switching control section 234, and outputs the selected signal to the output terminal 239 and the signal converting section 240.

The output terminal 239 is connected to the RGB monitor 215 through the signal line 210a shown in FIG. 28 and the RGB component signal outputted from the connecting switching circuit 238 is supplied to the RGB monitor 215 through the terminal 239. Thus, a moving image of the object photographed by the video endoscope 211 or 213 is displayed on the RGB monitor 215 on the basis of the RGB component signal.

The signal converting section 240 includes an RGB-Y/C converting circuit 245, an RGB-NTSC encoder 246, an output terminal 247 connected to the RGB-Y/C converting circuit 245, and an output terminal 248 connected to the RGB-NTSC encoder 246. The RGB component signal outputted from the connecting switching circuit 238 is inputted to each of the RGB-Y/C converting circuit 245 and the RGB-NTSC encoder 246.

The RGB-Y/C converting circuit 245 converts the RGB component signal inputted thereto to a Y/C signal and outputs this converted Y/C signal to the output terminal 247. On the other hand, the RGB-NTSC encoder 246 converts the RGB component signal inputted thereto to an NTSC composite signal and outputs this converted NTSC composite signal to the output terminal 248. For example, the RGB-NTSC encoder 246 can be constructed by using an IC "V70400", "CXA1145M", "CXA1145P" manufactured by SONY corporation.

The output terminal 247 is not used in this embodiment, but can be used to supply the Y/C signal outputted from the RGB-Y/C converting circuit 245 to another monitor capable of displaying a moving image based on the Y/C signal. In contrast to this, the output terminal 248 is connected to the TV monitor 216 through the signal line 210b shown in FIG. 28 and supplies the NTSC composite signal to the TV monitor 216. A moving image photographed by the video endoscope 211 or 213 is displayed on the TV monitor 216 on the basis of this NTSC composite signal.

In FIG. 29, the RGB component signal processing section 231 is shown such that the RGB component signal is transmitted through one signal transmitting path. However, the RGB component signal consists of a R (red) signal, a G (green) signal a B (blue) signal and a synchronous signal. Accordingly, the RGB component signal processing section 231 has four signal transmitting paths each corresponding to respective signal included in the RGB component signal. Therefore, four sets of buffer amplifiers 241, 242 and the video change-over switches 243, 244 are prepared for four signals included in the RGB component signal, respectively. The output terminal 239 comprises four BNC terminals and the output terminal 247 comprises two BNC terminals. The output terminal 248 comprises one BNC terminal.

The above input terminals 236, 237 correspond to an input section of the present invention. The connecting switching circuit 238 corresponds to a selecting section of the present invention. The signal converting section 240 corresponds to a signal generating section of the present invention. Further, the output terminals 249, 247, 248 correspond to an output section of the present invention.

The Y/C signal processing section 232 comprises input terminals 250, 251, a connecting switching circuit 252 connected to each of these input terminals 250, 251 through a signal line, an output terminal 253 and a signal converting section 254 connected to the connecting switching circuit 252.

The input terminal 250 is connected to the processor device 218 through the signal line 218a shown in FIG. 28. Through the input terminal 250, the Y/C signal (called "Y/C signal A") showing the moving image of an object photographed by the video endoscope 217 is inputted. On the other hand, the input terminal 251 is connected to the processor device 220 through the signal line 220a shown in FIG. 28. Through the input terminal 251, a Y/C signal (called "Y/C signal B") showing a moving image of the object photographed by the video endoscope 219 is inputted.

The connecting switching circuit 252 has a construction similar to that of the above-mentioned connecting switching circuit 238. The connecting switching circuit 252 closes one of video change-over switches 257, 258 and opens the other in accordance with respective switching signals a, b inputted from the switching control section 234. Thus, one of the Y/C signals A and B is selected and outputted to the output terminal 253 and the signal converting section 254.

The output terminal 253 is connected to the Y/C monitor 229 through the signal line 210g shown in FIG. 28 and the Y/C signal outputted from the connecting switching circuit 252 is supplied to the Y/C monitor 221 through the terminal 253. The moving image photographed by the video endoscope 217 or 219 is displayed on the Y/C monitor 229 on the basis of this Y/C signal.

The signal converting section 254 includes a Y/C-RGB converting circuit 259, a Y/C-NTSC encoder 260, an output terminal 261 connected to the Y/C-RGB converting circuit 259, and an output terminal 262 connected to the Y/C-NTSC encoder 260. The Y/C signal outputted from the connecting switching circuit 252 is inputted to the Y/C-RGB converting circuit 259 and the Y/C-NTSC encoder 260.

The Y/C-RGB converting circuit 259 converts the Y/C signal inputted thereto to an RGB component signal and outputs this RGB component signal to the output terminal 261. On the other hand, the Y/C-NTSC encoder 260 converts the Y/C signal inputted thereto to an NTSC composite signal and outputs this NTSC composite signal to the output terminal 262. For example, this Y/C-NTSC encoder 260 can be constructed by using an IC "CXA1229M/P" manufactured by SONY corporation.

The output terminal 261 is connected to the RGB monitor 222 through the signal line 210d shown in FIG. 28 and the RGB signal outputted from the Y/C-RGB converting circuit 259 is supplied to the RGB monitor 222 through the terminal 261. The moving image photographed by the video endoscope 217 or 219 is displayed on the RGB monitor 222 on the basis of this RGB signal.

The output terminal 262 is connected to the video recorder 227 through the signal line 210e shown in FIG. 28 and the NTSC composite signal outputted form the Y/C-NTSC encoder 260 is supplied to the video recorder 227 through the terminal 262. The video recorder 227 records the moving image photographed by the video endoscope 217 or 219 on the basis of this NTSC composite signal.

In FIG. 29, the Y/C signal processing section 232 is constructed such that the Y/C signal is transmitted through one signal transmitting path. However, the Y/C signal consists of a Y-signal (luminance signal) and a C-signal (color-difference signal or carrier chrominance signal). Accordingly, the Y/C signal processing section 232 has two signal transmitting paths. Therefore, two sets of the buffer amplifiers 255, 256 and the video change-over switches 257, 258 are prepared for two signals included in the Y/C signal, respectively. The output terminal 253 comprises two BNC terminals. The output terminal 261 comprises four BNC terminals. The output terminal 262 comprises one BNC terminal.

The above input terminals 250, 251 correspond to an input section of the present invention. The connecting switching circuit 252 corresponds to a selecting section of the present invention. The signal converting section 254 corresponds to a signal generating section of the present invention. The output terminals 253, 261, 262 correspond to an output section of the present invention.

The NTSC composite signal processing section 233 comprises input terminals 264, 265, a connecting switching circuit 266 connected to each of these input terminals 264, 265 through a signal line, and an output terminal 267 and a signal converting section 268 connected to the connecting switching circuit 266.

The input terminal 264 is connected to the processor device 224 through the signal line 224a shown in FIG. 28, through which the NTSC composite signal (called "NTSC-COMP signal A") showing the moving image of an object photographed by the video endoscope 223 is inputted. On the other hand, the input terminal 265 is connected to the processor device 226 through the signal line 226a shown in FIG. 28. Through the inpur terminal 265, an NTSC composite signal (called "NTSC-COMP signal B") showing a moving image of the object photographed by the video endoscope 225 is inputted.

The connecting switching circuit 266 has a construction similar to that of the above-mentioned connecting switching circuit 238. The connecting switching circuit 266 closes one of video change-over switches 271 and 272 and opens the other in accordance respective switching signals a, b inputted from the switching control section 234. Thus, one of the NTSC-COMP signals A and B is selected and outputted to the output terminal 267 and the signal converting section 268.

The output terminal 267 is connected to the video recorder 228 through the signal line 210f shown in FIG. 28 and the video signal outputted from the connecting switching circuit 266 is supplied to the video recorder 228 through the output terminal 267. Thus, a picture image photographed by the video endoscope 223 or 225 is recorded by the video recorder 228.

The signal converting section 268 includes an NTSC-RGB decoder 273, an NTSC-Y/C decoder 274, an output terminal 275 connected to the NTSC-RGB decoder 273, and an output terminal 276 connected to the NTSC-Y/C decoder 274. The NTSC composite signal outputted from the connecting switching circuit 266 is inputted to the NTSC-RGB decoder 273 and the NTSC-Y/C decoder 274.

The NTSC-RGB decoder 273 converts the NTSC composite signal inputted thereto to RGB component signal and outputs this RGB component signal to the output terminal 275. For example, this NTSC-RGB decoder 273 can be constructed by using an IC "V7021" manufactured by SONY corporation. On the other hand, the NTSC-Y/C decoder 274 converts the NTSC composite signal inputted thereto to Y/C signal and outputs this Y/C signal to the output terminal 276. For example, the NTSC-Y/C decoder 274 can be constructed by using an IC "CXA1228S" manufactured by SONY corporation.

The output terminal 275 is not used in this embodiment, but can be used to supply the RGB signal outputted from the NTSC-RGB decoder 273 to another monitor capable of displaying a moving image based on the RGB signal. In contrast to this, the output terminal 276 is connected to the Y/C monitor 229 through the signal line 210g shown in FIG. 28 and supplies the Y/C signal outputted from the NTSC-Y/C decoder 274 to the Y/C monitor 229. The moving image photographed by the video endoscope 223 or 225 is displayed on the Y/C monitor 229 on the basis of the Y/C signal.

The output terminal 267 comprises one BNC terminal. The output terminal 275 comprises four BNC terminals. The output terminal 276 comprises two BNC terminals. The above input terminals 264, 265 correspond to an input section of the present invention. The connecting switching circuit 266 corresponds to a selecting section of the present invention. The signal converting section 268 corresponds to a signal generating section of the present invention. The output terminals 267, 275, 276 correspond to an output section of the present invention.

Figure 30:
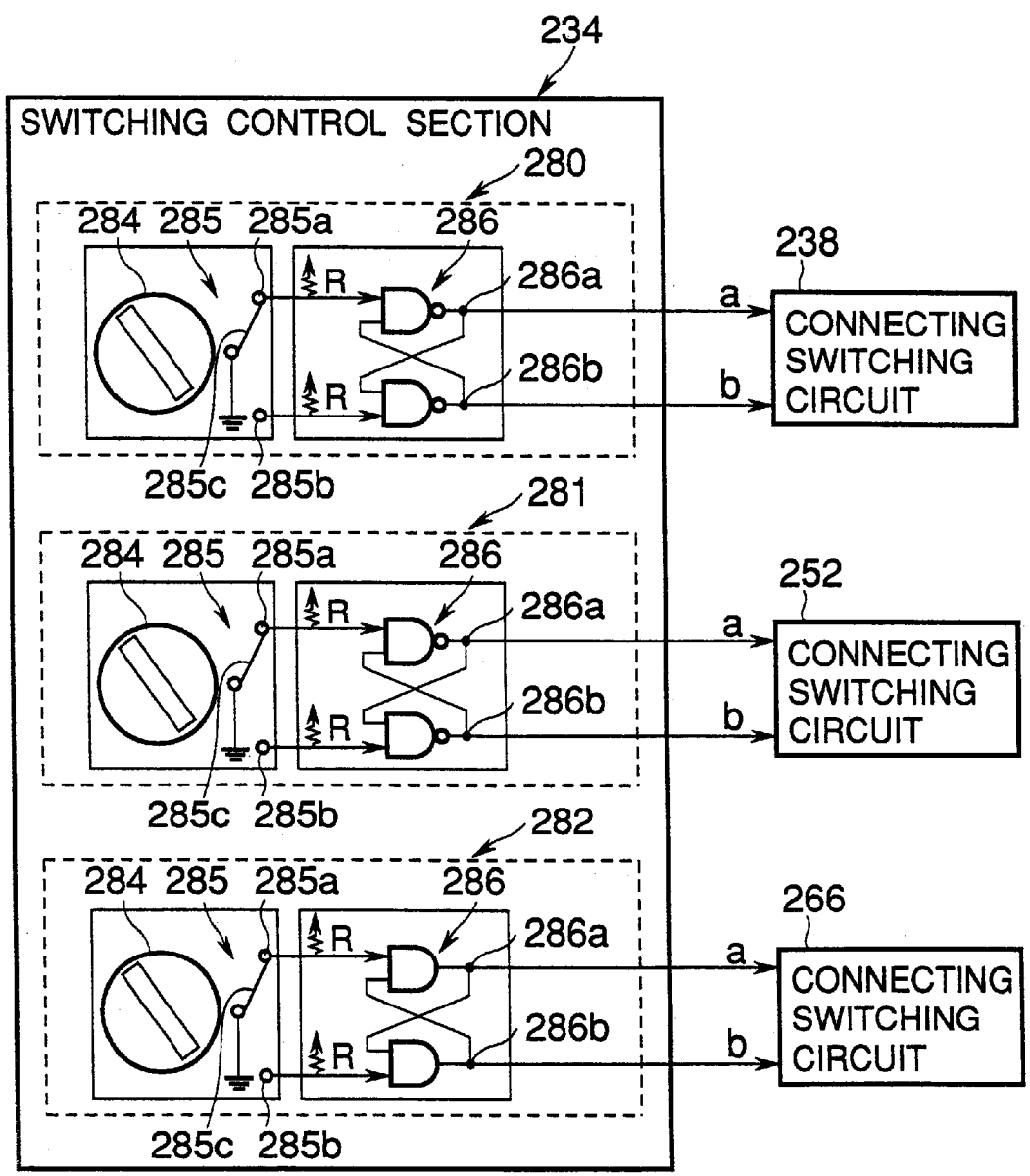
FIG. 30 is a circuit diagram of a switching control section shown in FIG. 29.

The switching control section 234 applies the switching signals a and b to each of the connecting switching circuits 238, 252, 266 in accordance with the condition of the video signal switching device 200 set by an operator. FIG. 30 is a circuit diagram showing the construction of the switching control section 234. As shown in FIG. 30, the switching control section 234 comprises a switching circuit control section 280 for controlling an operation of the connecting switching circuit 238 shown in FIG. 29, a switching circuit control section 281 for controlling an operation of the connecting switching circuit 252, and a switching circuit control section 282 for controlling an operation of the connecting switching circuit 266. The respective switching circuit control sections 280 through 282 have the same construction. Accordingly, the switching circuit control section 280 will next be explained as a representation.

The switching circuit control section 280 is constructed of a switching dial 284, a manual change-over switch 285 for performing a switching operation according to rotational position of the switching dial 284, and a flip flop 286 connected to each of contacts 285a, 285b of the manual change-over switch 285. Each of output terminals 286a, 286b of the flip flop 286 is connected to the connecting switching circuit 238.

Rotatable range of the switching dial 284 is divided into a first range in which the RGB signal (the RGB signal A) inputted through the input terminal 236 shown in FIG. 29 is selected and a second range in which the RGB signal (the RGB signal B) inputted through the input terminal 237 is selected. The rotational position of the switching dial 284 is set within the first or second ranges by the operator of the video signal switching device 200.

The manual change-over switch 285 has contacts 285a, 285b and a switching brush 285c selectively coming in contact with the terminals 285a, 285b and connected to the ground. This switching brush 285c is switched to come in contact with the contact 285a when the rotational position of the switching dial 284 is set to the above first range. The switching brush 285c is switched to come in contact with the contact 285b when the rotational position of the switching dial 284 is set to the second range.

One input terminal of the flip flop 286 is connected to the contact 285a and pulled up through a resistor R and the other input terminal is connected to the contact 285b and pulled up through a resistor R. On the other hand, one output terminal 286a of the flip flop 286 is connected to a control terminal of the video change-over switch 243 of the connecting switching circuit 238 and a switching signal a for controlling opening and closing of the video change-over switch 243 is applied through the terminal 286a to the control terminal. The other output terminal 286b of the flip flop 286 is connected to a control terminal of the video change-over switch 244 of the connecting switching circuit 238 and switching signal b for controlling opening and closing of the video change-over switch 244 is applied through the terminal 286b to the control terminal. Potential levels of the respective control signals a, b are changed in accordance with the rotational position of the switching dial 284. More specifically, when the rotational position of the switching dial 284 is set to the first range, the switching brush 285c comes in contact with the contact 285a so that the terminal 285a is connected to the ground. Therefore, potential level inputted to the flip flop 286 becomes low on a side of the contact 285a and becomes high on a side of the contact 285b. Accordingly, the potential level of the switching signal a outputted through the output terminal 286a of the flip flop 286 becomes high and the potential level of the switching signal b outputted through the output terminal 286b becomes low. On the contrary, when the rotational position of the switching dial 284 is set to the second range, the switching brush 285c comes in contact with the contact 285b, so that the contact 285b is connected to the ground. Accordingly, potential level of the switching signals a, b outputted from the flip flop 286 is inverted. More specifically, the potential level of the switching signal a outputted through the output terminal 286a becomes low and the potential level of the switching signal b outputted through the output terminal 286b becomes high.

The following table 7 shows the relation of the potential level of each of the respective switching signals a, b outputted from the switching circuit control section 280 shown in FIG. 30 and each of the video signal outputted from the connecting switching circuit 238.

TABLE 7

| Switching signal a | Switching signal b | R G B component signal | Y/C signal | NTSC-COMP signal |
|---|---|---|---|---|
| High | Low | RGB signal A | Y/C signal A | NTSC-COMP signal A |
| Low | High | RGB signal B | Y/C signal B | NTSC-COMP signal B |

As shown in this table 7, when the switching signal a has high potential and the switching signal b has a low potential, only the video change-over switch 243 is closed and the RGB signal A is outputted from the connecting switching circuit 238. In contrast to this, when the switching signal a has low potential and the switching signal b has high potential, only the video change-over switch 244 is closed and the RGB signal B is outputted from the connecting switching circuit 238.

The output terminals 286a, 286b of the flip flop 286 of the switching circuit control section 281 respectively transmit the switching signals a, b to the control terminals of the video change-over switches 257, 258 of the connecting switching circuit 252. Similarly, the output terminals 286a, 286b of the flip flop 286 of the switching circuit control section 282 respectively transmit the switching signals a, b to the control terminals of the video change-over switches 271, 272 of the connecting switching circuit 266. Thus, the respective connecting switching circuits 252, 266 output video signals according to the table 7.

The switching control section 234 may be constructed to control the respective connecting switching circuits 238, 252, 266 so that they approximately simultaneously perform in same way. Further, the switching control section 234 in this ninth embodiment comprises a logic circuit, but may comprises a processor device mainly composed of a CPU and a memory.

<Operation of Video Signal Switching Device>

An operation of the video signal switching device 200 in the ninth embodiment will next be explained. The RGB signal processing section 231, the Y/C signal processing section 232 and the NTSC signal processing section 233 in the video signal switching device 200 perform approximately similar operations. Accordingly, an operating example of the RGB signal processing section 231 will be explained here as a representation.

The RGB signal A is inputted from the processor device 212 to the input terminal 236 of the RGB signal processing section 231. The RGB signal B is inputted from the processor device 214 to the input terminal 237. These RGB signals A and B are transmitted to the connecting switching circuit 238.

The respective video change-over switches 243, 244 of the connecting switching circuit 238 perform opening and closing according to the switching signals a, b outputted from the switching control section 234 (the switching circuit control section 280). At this time, if the rotational position of the switching dial 284 of the switching circuit control section 280 is set to the first range, the switching signal a of high potential applied to the video change-over switch 243 and the switching signal b of low potential is applied to the video change-over switch 244. Therefore, the video change-over switch 243 is closed and the video change-over switch 244 is opened. Accordingly, the RGB signal A is outputted from the connecting switching circuit 238.

Thereafter, if the rotational position of the switching dial 284 of the switching circuit control section 280 is set to the second range, the switching signal a of low potential is applied to the video change-over switch 243 and the switching signal b of high potential is applied to the video change-over switch 244. Therefore, the video change-over switch 244 is closed and the video change-over switch 243 is opened. Accordingly, an output signal of the connecting switching circuit 238 is switched over from the RGB signal A to the RGB signal B. Thus, the connecting switching circuit 238 selects an RGB component signal to be outputted from the RGB signals A and B in accordance with potential levels of the respective switching signals a, b (namely, rotational position of the switching dial 284).

The RGB component signal (the RGB signal A or B) outputted from the connecting switching circuit 238 is transmitted to the output terminal 239 and the signal converting section 240. The RGB component signal transmitted to the output terminal 239 is supplied to the RGB monitor 215 (see FIG. 28) through the signal line 210a. On the other hand, the RGB component signal transmitted to the signal converting section 240 is inputted to the RGB-Y/C converting circuit 245 and the RGB-video encoder 246.

The RGB-Y/C converting circuit 245 converts the RGB signal inputted thereto to Y/C signal and outputs this Y/C signal. On the other hand, the RGB-NTSC encoder 246 converts the RGB component signal inputted thereto to NTSC composite signal and outputs this NTSC composite signal. The NTSC composite signal outputted from the RGB-NTSC encoder 246 is transmitted from the output terminal 248 to the TV monitor 216 through the signal line 210b.

<Operation in Ninth Embodiment>

The video signal switching device 200 in the ninth embodiment selects one of two video signals inputted from the two video processors for an endoscope in accordance with the setting by an operator and converts the selected video signal in a form adapted to an output device and supplies this converted video signal to the output device. More specifically, the video signal switching device 200 selects one of the RGB signals A and B inputted thereto in accordance with setting of the switching circuit control section 280 and converts the selected RGB component signal to an NTSC composite signal and supplies this NTSC composite signal to the TV monitor 216. The video signal. switching device 200 also selects one of the Y/C signals A and B inputted thereto in accordance with setting of the switching circuit control section 281 and converts the selected Y/C signal to an RGB component signal and supplies this converted RGB component signal to the RGB monitor 222. The video signal switching device 200 also converts the selected Y/C signal to an NTSC composite signal and supplies this converted NTSC composite signal to the video recorder 227. Further, the video signal switching device 200 selects one of the NTSC composite signals A and B inputted thereto in accordance with setting of the switching circuit control section 282 and converts the selected NTSC composite signal to a Y/C signal and supplies this Y/C signal to the Y/C monitor 229.

Thus, in accordance with the video signal switching device 200 in the ninth embodiment, even if formats of the video signals inputted to this video signal switching device 200 are different from the those of video signals able to be displayed on a monitor (able to be recorded by a video recorder), the video signal switching device 200 can be connected to the monitor (or the video recorder), and formats of the video signals to be supplied to the monitor (the video device) can be converted into that adapted to the monitor (or video recorder) in accordance with setting.

Therefore, an endoscope system can be assembled from the monitor and the video recorder, irrespective of the format of the video signal treatable by the monitor and the video recorder. Accordingly, it is not necessary to prepare monitors and video recorders according to video signals outputted from processors, so that a space can be effectively utilized.

Further, whichever the video signals inputted to the video signal switching device 200 is the RGB component signal, the Y/C signal or the NTSC composite signal, the video signal switching device 200 can supply a video signal of any format among signals of thse formats to the monitor and the video recorder. Therefore, wiring of the endoscope system and its work can be simplified.

Figure 31:
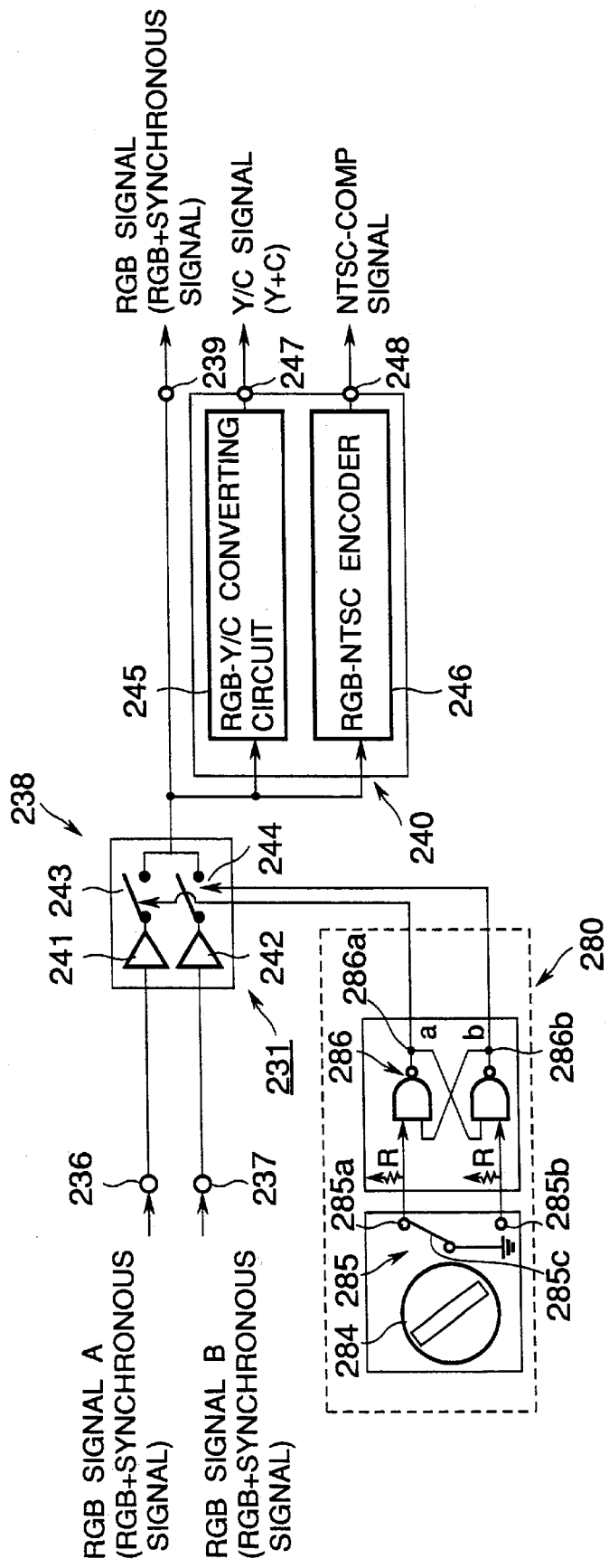
FIG. 31 is a circuit diagram showing a variation of a main portion of the video signal switching device in the ninth embodiment of the present invention.
Figure 32:
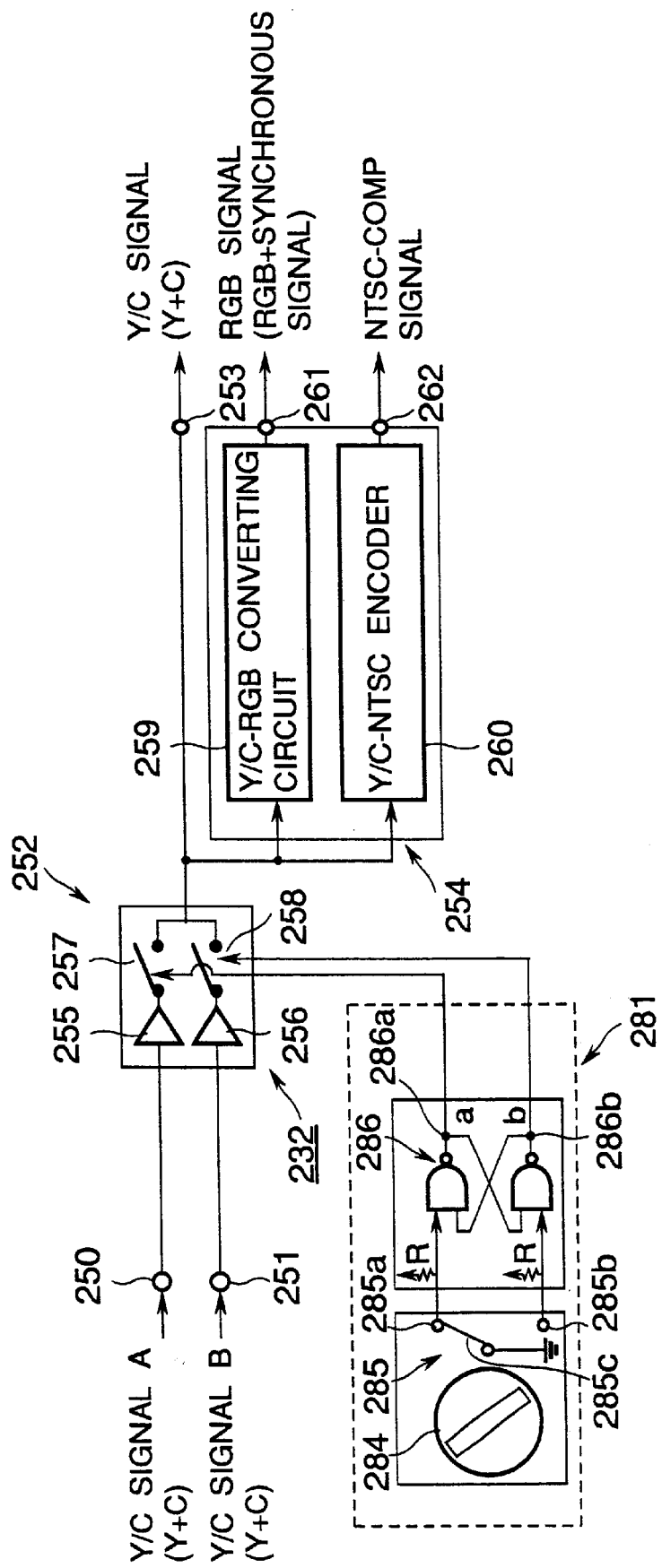
FIG. 32 is a circuit diagram showing a variation of a main portion of the video signal switching device in the ninth embodiment of the present invention.
Figure 33:
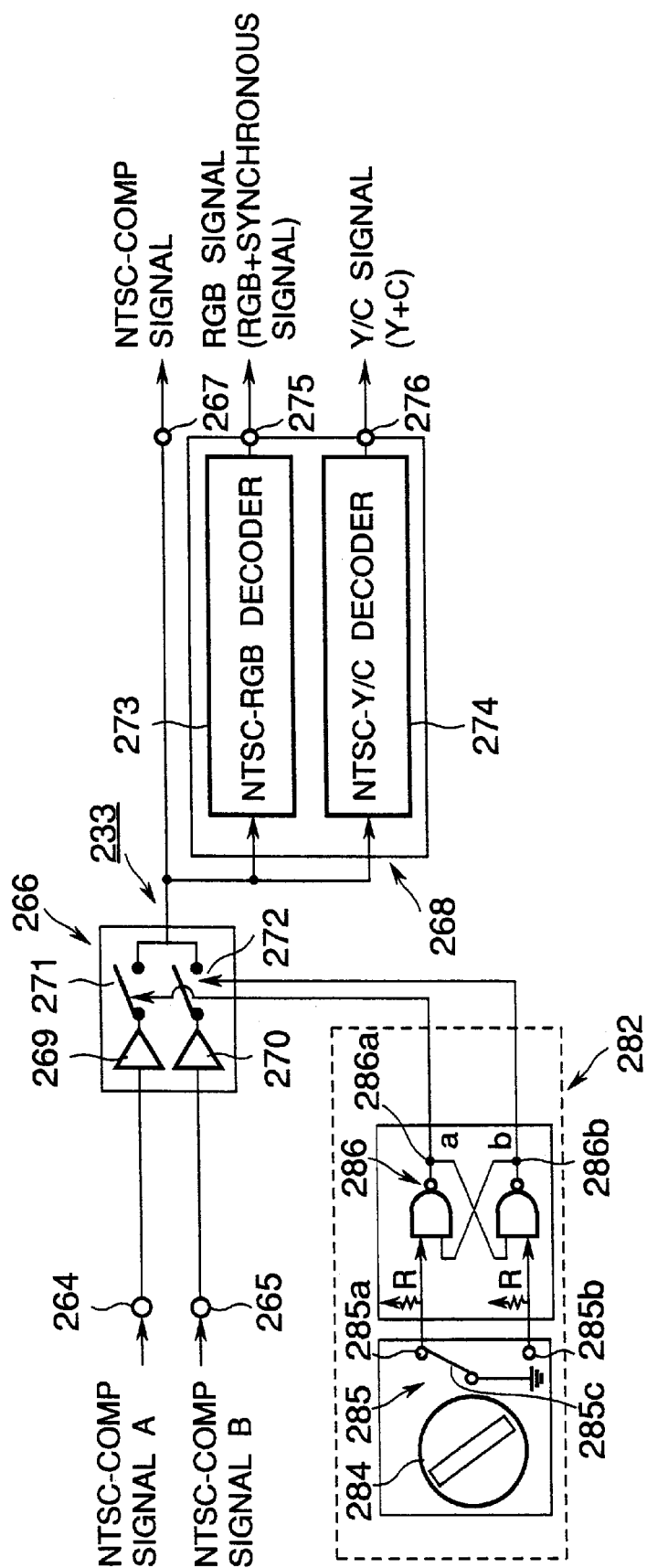
FIG. 33 is a circuit diagram showing a variation of a main portion of the video signal switching device in the ninth embodiment of the present invention.

As shown in FIG. 31, the video signal switching device may comprise only the RGB component signal processing section 231 (see FIG. 29) and the switching circuit control section 280 (see FIG. 30). As shown in FIG. 32, the video signal switching device may also comprise only a Y/C signal processing section 232 and a switching circuit control section 281. Further, as shown in FIG. 33, the video signal switching device may comprises only an NTSC component signal processing section 232 and a switching circuit control section 282.

TENTH EMBODIMENT

Figure 34:
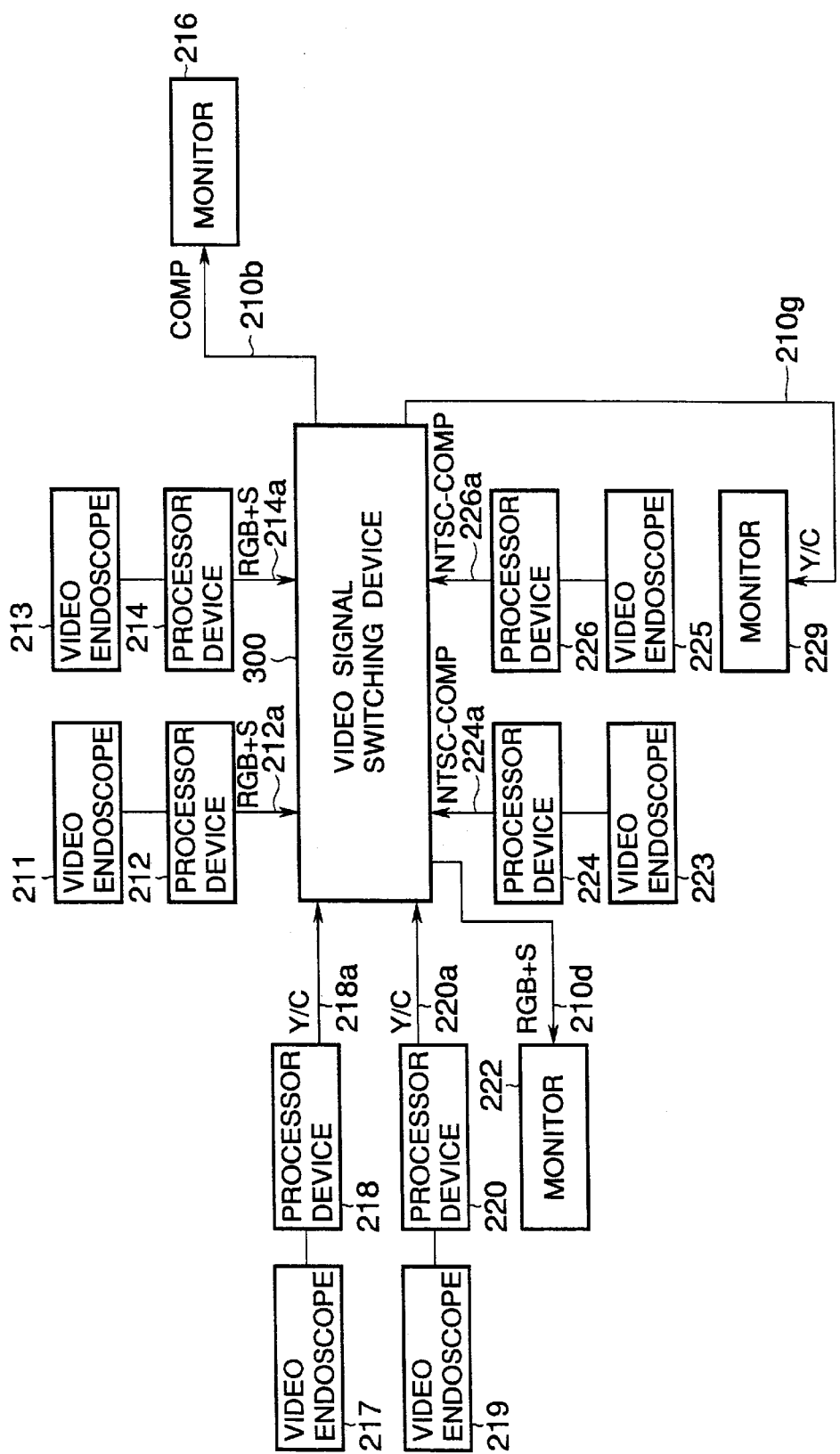
FIG. 34 is a schematic view of an endoscope system in a tenth embodiment of the present invention.

FIG. 34 is a schematic view showing the endoscope system in a tenth embodiment of the present invention. The endoscope system shown in FIG. 34 differs from the endoscope system shown in FIG. 28 in the point that monitors 215, 221 and video recorders 227, 228 are omitted.

Figure 35:
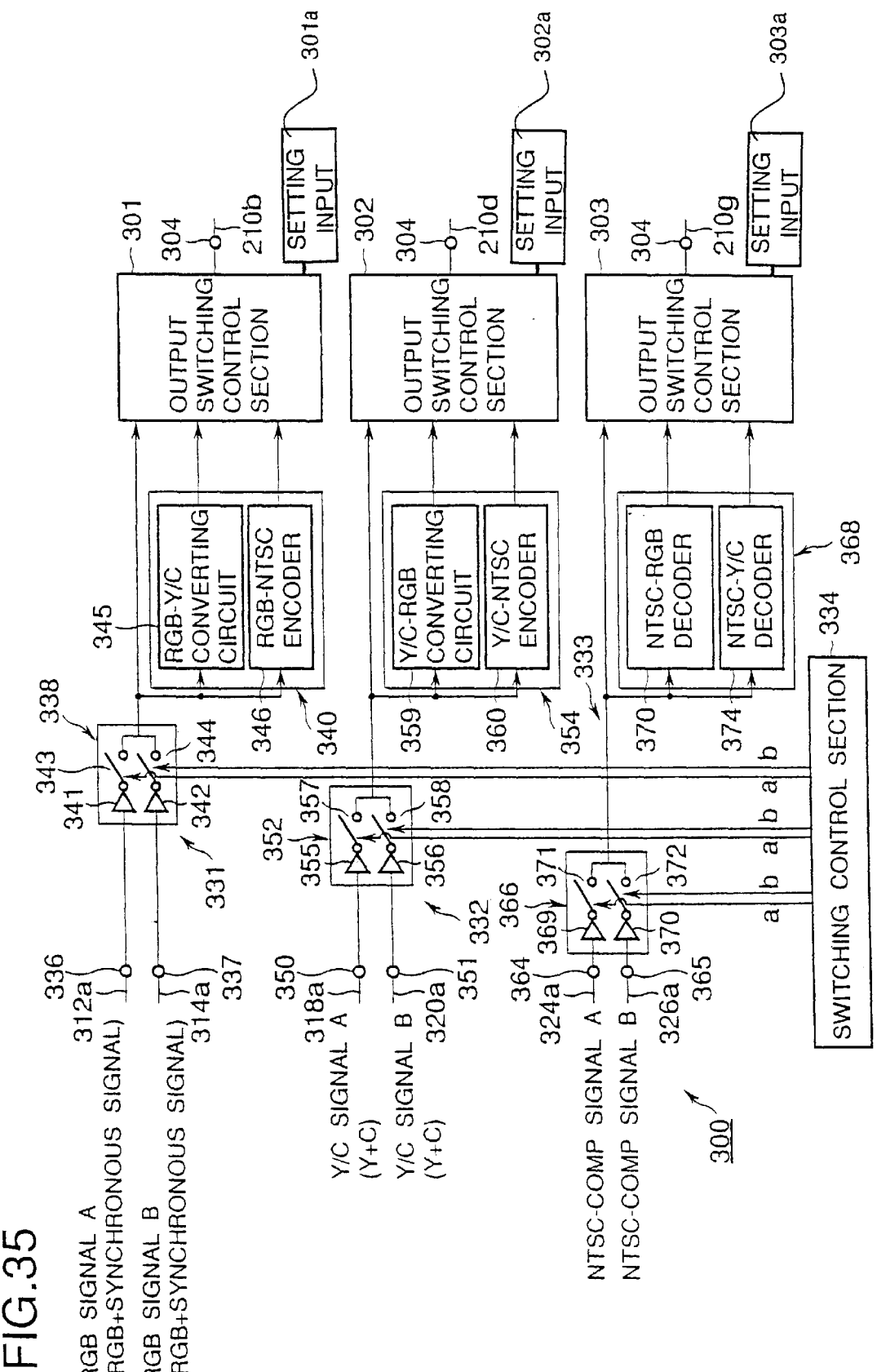
FIG. 35 is a circuit diagram of a main portion of a video signal switching device shown in FIG. 34.

FIG. 35 is a circuit diagram showing the construction of the video signal switching device 300 shown in FIG. 34. The video signal switching device 300 differs from the video signal switching device 200 in the ninth embodiment in same points. More specifically, as shown in FIG. 35, an RGB signal processing section 331 has an output switching control section 301 instead of output terminals 239, 247, 248 (see FIG. 29). A Y/C signal processing section 332 has an output switching control section 302 instead of output terminals 253, 261, 262 (see FIG. 29). An NTSC composite signal processing section 333 has an output switching control section 303 instead of output terminals 267, 275, 276 (see FIG. 29).

Each of the output switching control sections 301 through 303 may comprises an analog switch (a multiplexer IC). An RGB component signal outputted from the connecting switching circuit 338 and a Y/C signal and an NTSC composite signal outputted from the signal converting section 340 are inputted to the output switching control section 301. A Y/C signal outputted from the connecting switching circuit 352 and an RGB component signal and an NTSC composite signal outputted from the signal converting section 354 are inputted to the output switching control section 302. An NTSC composite signal outputted from the connecting switching circuit 366 and an RGB component signal and a Y/C signal outputted from the signal converting section 368 are inputted to the output switching control section 303.

Each of the output switching control sections 301 through 303 has an output terminal 304. Each output terminal 304 comprises four BNC terminals. Each of the output switching control sections 301 through 303 selects one of the RGB component signal, the Y/C signal and the NTSC composite signal inputted thereto and outputs the selected video signal through the output terminal 304 in accordance with setting thereof.

In this tenth embodiment, the output switching control section is set such that the NTSC composite signal is outputted. The output terminal 304 of this output switching control section is connected to the monitor 216 through the signal line 210b shown in FIG. 34. The output switching control section 302 is set such that the RGB component signal is outputted. The output terminal 304 of this output switching control section 302 is connected to the monitor 222 through the signal line 210d. The output switching control section 303 is set such that the Y/C signal is outputted. The output terminal 304 of the output switching control section is connected to the monitor 229 through the signal line 210g.

The above output switching control sections 301 to 303 correspond to an output selecting section of the present invention and the output terminals 304 correspond to an output section of the present invention. Each of the output switching control sections 301 through 393 may be set with any setting method (e.g., vie setting inputs 301a through 303a, shown in FIG. 35). For example, each of the output switching control sections 301 through 303 may be set manually (e.g., where the setting inputs 301a–303a include a multi-value switch) or automatically (e.g., where the setting inputs 301a–303a include, or are connected to, a detector responsive to the type of output monitor).

The video signal switching device 300 in the tenth embodiment has effects approximately similar to those of the video signal switching device 200 in the ninth embodiment. Further, the number of output terminals of the video signal switching device 300 is small in comparison with the video signal switching device 200. More specifically, twenty-one BNC terminals (constructed by 4×3 for the RGB component signal, 2×3 for the Y/C signal and 1×3 for the NTSC composite signal) are required in the video signal switching device 200. In contrast to this, it is sufficient to arrange twelve BNC terminals in the video signal switching device 300.

The video signal switching device 300 in the tenth embodiment is constructed such that only one video signal is outputted through the output terminal 304 of the output switching control section 301. However, since the remaining three BNC terminals of this output terminal 304 are not used, a Y/C signal outputted from an RGB-Y/C converting section 345 may be supplied to other output devices through the remaining these three BNC terminals. Similarly, since two BNC terminals of the output terminal 304 of the output switching control section 303 are not used, an NTSC composite signal outputted from the switching circuit 366 may be supplied to other output devices through one of the remaining BNC terminals.

ELEVENTH EMBODIMENT

FIG. 36 is a circuit diagram showing the construction of the video signal switching device 400 in an eleventh embodiment of the present invention. As shown in FIG. 36, the video signal switching device 400 differs from the video signal switching device 300 in the tenth embodiment only in the point that the video signal switching device 400 has only one output switching control section 405 instead of the three output switching control sections 301 through 303 of the video signal switching device 300.

The output switching control section 405 receives an RGB component signal, a Y/C signal and an NTSC composite signal from each of connecting switching circuits 438, 452, 466 and each of signal converting sections 440, 454, 468 and selects one of these signals and outputs the selected signal through an output terminal 404 in accordance with setting thereof. The output terminal 404 comprises four BNC terminals. The following table 8 shows a setting example of signals outputted from the respective BNC terminals of the output switching control section 405.

TABLE 8

| Setting | BNC terminal 1 | BNC terminal 2 | BNC terminal 3 | BNC terminal 4 |
|---|---|---|---|---|
| 1 | R-signal | G-signal | B-signal | Synchronous signal |
| 2 | Y-signal 1 | C-signal 1 | Y-signal 2 | C-signal 2 |
| 3 | Y-signal 1 | C-signal 1 | NTSC-COMP signal 1 | NTSC-COMP signal 2 |
| 4 | NTSC-COMP signal 1 | NTSC-COMP signal 2 | NTSC-COMP signal 3 | NTSC-COMP signal 4 |

As shown in the table 8, the output switching control section 405 can set signals to be outputted through the four BNC terminals constituting the output terminal 404 in four pattern. This output switching control section 405 corresponds to an output selection of the present invention, and may be set manually (e.g., where a setting input 405a includes a multi-value switch) or automatically (e.g., where the setting input 405a includes, or is connected to, a detector responsive to the type of output monitor). It should be noted that the setting examples of the eleventh embodiment can be applied to the tenth embodiment.

In addition to effects of the video signal switching device 300 in the tenth embodiment, the video signal switching device 400 in the eleventh embodiment has an effect that the number of BNC terminals can be further reduced.

We claim:

1. A video signal switching device which selectively outputs video signals received from plural video processor devices for endoscopes and which is separated from said video processor devices, comprising:

plural video signal input terminals to be connected to respective video signal output terminals of said video processors;

a video signal output terminal through which a video signal is outputted;

a connecting change-over switch to select one of said plural video signal input terminals to connect the selected input terminal to said video signal output terminal in accordance with a control signal; and a control signal generator for generating said control signal in accordance with a manual operation of an operator, said control signal generator having a keyboard including a key pushed down by the operator, and a control signal generating circuit for generating said control signal making said connecting change-over switch change the video signal input terminal to be selected, every time said key is pushed down.

2. A video signal switching device which selectively outputs video signals received from plural video processor devices for endoscopes and which is separated from said video processor devices, comprising:

plural video signal input terminals to be connected to respective video signal output terminals of said video processors;

a video signal output terminal through which a video signal is outputted;

a connecting change-over switch to select one of said plural video signal input terminals to connect the selected input terminal to said video signal output terminal in accordance with a control signal; and a control signal generator for generating said control signal in accordance with a manual operation of an operator, said control signal generator having;

a wireless remote controller for transmitting a wireless remote control signal according to the operation of the operator, a signal receiving section for receiving the wireless remote control signal transmitted from the wireless remote controller, and a control signal generating circuit for generating said control signal making said connecting change-over switch change the video signal input terminal to be selected, every time said signal receiving section receives said wireless remote control signal.

3. A video signal switching device which selectively outputs video signals received from plural video processor devices for endoscopes and which is separated from said video processor devices, comprising:

plural video signal input terminals to be connected to respective video signal output terminals of said video processors;

a video signal output terminal through which a video signal is outputted;

a connecting change-over switch to select one of said plural video signal input terminals to connect the selected input terminal to said video signal output terminal in accordance with a control signal; and an indicator showing the video signal input terminal connected to said video signal output terminal by said connecting change-over switch.

4. A video signal switching device which selectively outputs video signals received from plural video processor devices for endoscopes and which is separated from said video processor devices, comprising:

plural video signal input terminals to be connected to respective video signal output terminals of said video processors;

a video signal output terminal through which a video signal is outputted;

a connecting change-over switch to select one of said plural video signal input terminals to connect the selected input terminal to said video signal output terminal in accordance with a control signal;

a control signal generator for generating said control signal in accordance with a manual operation of an operator;

a video signal detecting circuit for detecting whether a video signal is inputted to each of said video input terminals or not; and a switching control circuit for generating a control signal making said connecting change-over switch select the video input terminal to which the video signal is inputted in precedence to that generated by said control signal generator, when said video signal detecting circuit detects that a video signal is inputted to only one of said video input terminals.

5. A video signal switching device which selectively outputs video signals received from plural video processor devices for endoscopes and which is separated from said video processor devices, comprising:

plural video signal input terminals to be connected to respective video signal output terminals of said video processors;

a video signal output terminal through which a video signal is outputted;

a connecting change-over switch to select one of said plural video signal input terminals to connect the selected input terminal to said video signal output terminal in accordance with a control signal;

a control signal generator for generating said control signal in accordance with a manual operation of an operator;

a power input terminal to be connected to a commercial power source;

a power output terminal for supplying power from the commercial power source to an external device;

a video signal detecting circuit for detecting whether a video signal is inputted to each of said video input terminals or not;

a power source section connected to said power input terminal and supplying power to said connecting change-over switch only when said video signal detecting circuit detects that a video signal is inputted to at least one of said video input terminals; and a power supplying switch section for electrically connecting said power input terminal and said power output terminal to each other only when said video signal detecting circuit detects that a video signal is inputted to at least one of said video input terminals.

6. The video signal switching device according to claim 5, further comprising:

a battery supplying power to each video signal detecting circuit.

7. The video signal switching device according to claim 6, wherein said battery is a secondary battery, and wherein said power source section charges said battery while said video signal detecting circuit detects that a video signal is inputted to at least one of said video input terminals.

8. A video signal switching device for selecting video signals received from plural video processor devices for endoscopes and outputs the selected video signals to first and second types of output devices processing the video signals, comprising:

plural first input sections for respectively receiving video signals in a first format outputted from any one of said video processors;

plural second input sections for respectively receiving video signals in a second format outputted from any one of said video processors;

a selecting section for selecting a video signal in the first format inputted to any one of said first input sections and selecting a video signal in the second format inputted to any one of said second input sections;

an output section for outputting the video signal in the first format selected by said selecting section to said first type of the output device, and outputting the video signal in the second format selected by said selecting section to said second type of the output device; and a control section for controlling a selecting operation of said selecting section in accordance with a condition set thereto.

9. The video signal switching device according to claim 8, wherein said control section controls said selecting section such that a selecting operation for the video signal in the first format is performed simultaneously with a selecting operation for the video signal in the second format.

10. The video signal switching device according to claim 8, wherein said control section controls said selecting section such that the selecting operation for the video signal in the first format is performed simultaneously with the selecting operation for the video signal in the second format corresponding to the video signal in the first format selected by the selecting operation.

11. The video signal switching device according to claim 8, wherein said video signal in the first format is any one of an RGB component signal, a brightness/color carrier signal and an NTSC composite signal, and said video signal in the second format is other one of the RGB composite signal, the brightness/color carrier signal and the NTSC composite signal.

12. The video signal switching device according to claim 8, wherein said selecting section has a first switch for transmitting only the video signal in the first format to be selected shown by a control signal received from said control section from said first input section to said output section, and a second switch for transmitting only the video signal in the second format to be selected shown by the control signal received from said control section from said second input section to said output section.

13. The video signal switching device according to claim 8, further comprising plural third input section constructed for receiving a video signals in a third format outputted from the plural video processor devices for endoscopes, wherein said selecting section selects a video signal in the third format inputted to any one of said third input section, and wherein said output section outputs the video signal in the third format selected by said selecting section to a third type of an output device.

14. The video signal switching device according to claim 13, wherein said control section controls said selecting section such that the selecting operation for the video signals in the first format is performed simultaneously with the selecting operation for the video signals in the second and third formats.

15. A video signal switching device for selecting video signals received from plural video processor devices for endoscopes and outputs the selected video signals to first and second types of output devices processing the video signals, comprising:

plural first input terminals to which video signals in a first format outputted from any one of said video processor devices are respectively inputted;

a first output terminal connected to said first type of the output device;

a first switching section for connecting said first output terminal and any one of said first input terminals to each other in accordance with a control signal;

plural second input terminals to which video signals in a second format different from the first format outputted from any one of said video processor devices are respectively inputted;

a second output terminal connected to said second type of the output device; and a second switching section for connecting said second output terminal and any one of said second input terminals to each other in accordance with the control signal.

16. A video signal switching device which selects video signals received from plural video processor devices for endoscopes and outputs the selected video signals to first type of an output device processing the video signals, comprising:

an input section to which the video signals outputted from said plural video processors are inputted;

a selecting section for selecting a video signal to be outputted among the video signals inputted to said input section in accordance with a control signal;

a signal generating section for generating a first converted video signal by converting format of the video signal selected by said selecting section to another one able to be processed by said first type of the output device; and an output section for outputting the converted video signal generated by said signal generating section to said first type of the output device, wherein said signal generating section generates a second converted video signal by converting the format of the video signal selected by said selecting section to another one able to be processed by second type of the output device, said output section outputs said second converted video signal to said second type of the output device, and said output section outputs the video signal selected by said selecting section to third-type of the output device.

17. The video signal switching device according to claim 16, further comprising an output selecting section for selecting one of the video signal selected by said selecting section, said first converted video signal and said second converted video signal in accordance with a control signal and applying the selected signal to said output section, and wherein said output section outputs only the video signal received from said output selecting section to an output device corresponding to the video signal to be outputted.

18. The video signal switching device according to claim 17, wherein said output selecting section selects one of said first and second converted video signals in accordance with the control signal and applies the selected signal to said output section, and wherein said output section outputs only the video signal received from said output selecting section to an output device corresponding to the converted video signal to be outputted.

19. A video signal switching device which selects video signals received from plural video processor devices for endoscopes and outputs the selected video signals to an output device processing the video signals, comprising:

an input section to which the video signals outputted from the plural video processor devices are inputted;

a selecting section for selecting a video signal to be outputted among the video signals inputted to said input section, for every format of the video signals;

a signal generating section for generating a converted video signal by converting the format of the video signal selected by said selecting section to another one able to be processed by an output device corresponding to the video signal, for every video signal selected by said selecting section;

an output section for outputting each converting video signal generated by said signal generating section to an output device corresponding to the converted video signal; and an output selecting section for selecting one of said plural converted video signals in accordance with a control signal, wherein said output section outputs only the converted video signal selected by said output selecting section to an output device corresponding to this converted video signal.

20. A video signal switching device which selects video signals received from plural video processor devices for endoscopes and outputs the selected video signals to an output device processing the video signals, comprising:

an input section to which the video signals outputted from the plural video processor devices are inputted;

a selecting section for selecting a video signal to be outputted among the video signals inputted to said input section, for every format of the video signals;

a signal generating section for generating a converted video signal by converting the format of the video signal selected by said selecting section to another one able to be processed by an output device corresponding to the video signal, for every video signal selected by said selecting section;

an output selecting section for selecting one of said plural converted video signals in accordance with a control signal; and an output section for outputting only the converted video signal selected by said output selecting section to said output device.

* * * * *